(12) United States Patent
Tsuruta et al.

(10) Patent No.: US 11,725,225 B2
(45) Date of Patent: Aug. 15, 2023

(54) PRODUCTION OF ISOPRENOIDS

(75) Inventors: Hiroko Tsuruta, Oakland, CA (US);
Jacob R. Lenihan, Emeryville, CA (US); Rika Regentin, Hayward, CA (US)

(73) Assignee: AMYRIS, INC., Emeryville, CA (US)

( * ) Notice: Subject to any disclaimer, the term of this patent is extended or adjusted under 35 U.S.C. 154(b) by 1187 days.

(21) Appl. No.: 12/234,589

(22) Filed: Sep. 19, 2008

(65) Prior Publication Data

US 2009/0137014 A1 May 28, 2009

Related U.S. Application Data

(60) Provisional application No. 60/994,790, filed on Sep. 20, 2007, provisional application No. 61/049,350, filed on Apr. 30, 2008.

(51) Int. Cl.
| | | |
|---|---|---|
| *C12P 23/00* | (2006.01) | |
| *C12N 1/32* | (2006.01) | |
| *C12P 5/00* | (2006.01) | |

(52) U.S. Cl.
CPC .............. *C12P 23/00* (2013.01); *C12N 1/32* (2013.01); *C12P 5/007* (2013.01); *Y02E 50/10* (2013.01)

(58) Field of Classification Search
CPC . C12P 5/007; C12P 23/00; C12N 1/32; Y02E 50/10
See application file for complete search history.

(56) References Cited

U.S. PATENT DOCUMENTS

| | | | | |
|---|---|---|---|---|
| 6,825,002 | B2 * | 11/2004 | Tsubokura et al. | 435/67 |
| 7,399,323 | B2 | 7/2008 | Renninger et al. | |
| 7,501,268 | B2 * | 3/2009 | Ohto et al. | 435/155 |
| 2005/0181490 | A1 | 8/2005 | Cheong et al. | |
| 2008/0083158 | A1 | 4/2008 | Renninger et al. | |
| 2008/0092829 | A1 | 4/2008 | Renninger et al. | |
| 2008/0274523 | A1 * | 11/2008 | Renninger et al. | 435/157 |
| 2009/0020089 | A1 | 1/2009 | Ryder et al. | |
| 2009/0020090 | A1 | 1/2009 | Ryder et al. | |
| 2011/0039299 | A1 * | 2/2011 | Bailey et al. | 435/67 |

FOREIGN PATENT DOCUMENTS

| | | |
|---|---|---|
| CA | 2 831 321 A1 | 1/2000 |
| JP | 2005-080625 | 3/2005 |
| WO | WO 2001/042476 A1 | 6/2001 |
| WO | 02/053746 * | 7/2002 |
| WO | WO 2003/102200 A2 | 12/2003 |
| WO | WO 2005/047486 A2 | 5/2005 |
| WO | WO 2008/042338 A2 | 4/2008 |

OTHER PUBLICATIONS

Y. Yamane et al. "Astaxanthin Production by Phaffia rhodozyma Enhanced in Fed=Batch Culture With Glucose and Ethanol Feeding", Biotechnology Letters 19(11): 1109-1111 (1997).*
L.M.D. Santopietro et al. "Fed-Batch and Continuous Culture of Phaffia rhodozyma" Folia Microbiologica 43(2): 169-172 (1998).*
Nature Lipidomics Gateway Database C15 and C20 ispreniods web pages. http://www.lipidmaps.org/data/structure/LMSDSearch.php retrieved on Nov. 3, 2011.*
D. Ro et al. "Production of the Antimalarial Drug Precursor Artemisinic Acid in Engineered Yeast", Nature, 440:940-943 (Apr. 2006).*
M.C.Y. Chang et al. Production of Isoprenoid Pharmaceuticals by Engineered Microbes, Nature Chemical Biology 2(12):674-681 (Nov. 2006).*
Barberel et al., The Effect of Aeration upon the Secondary Metabolism of Microorganisms. Biotechnol Genet. Eng. Rev., 2000, vol. 1: 281-323. (Year: 2000).*
Choi et al., Restricted electron flux increases coenzyme Q10 production in Agrobacterium tumefaciens ATCC4452. Process Biochem., 2005, vol. 40: 3225-3229. (Year: 2005).*
Maury et al., Microbial Isoprenoid Production: An Example of Green Chemistry through Metabolic Engineering. Adv Biochem Engin/Biotechnol., 2005, vol. 100: 19-51. (Year: 2005).*
Rosenfeld et al., Role of the non-respiratory pathways in the utilization of molecular oxygen by *Saccharomyces cerevisiae*. Yeast, 2003, vol. 20: 1115-1114. (Year: 2003).*
PCT International Search Report dated Jun. 25, 2009, for International Application No. PCT/US2008/010886, filed Sep. 19, 2008.
Carrau et al., "De novo synthesis of monoterpenes by *Saccharomyces cerevisiae* wine yeasts," Fems Microbiology Letters, Feb. 2005, vol. 243, No. 1, pp. 107-115.
Gu et al., Ethanol increases caratenoid production in Phaffia rhodozyma, Journal of Industrial Microbiology and Biotechnology, Jan. 1997, vol. 19, No. 2, pp. 114-117.
Lenihan et al., "Developing an industrial artemisinic acid fermentation process to support the cost-effective production of antimalarial artemisinin-based combination therapies," Biotechnology Progress, Sep. 2008, vol. 24, No. 5, pp. 1026-1032.
Ro et al., "Production of the antimalarial drug precursor artemisinic acid in engineered yeast," Nature, Apr. 2006, vol. 440, No. 7086, pp. 940-943.
Veen et al, "Combined overexpression of genes of the ergosterol biosynthetic pathway leads to accumulation of sterols in *Saccharomyces cerevisiae*," Fems Yeast Research, Oct. 2003, vol. 4, No. 1 pp. 87-95.
PCT International Search Report dated Dec. 12, 2007, for International Application No. PCT/US2007/012467, filed May 25, 2007.
U.S.P.T.O. Non-Final Office Action dated Oct. 2, 2008, for U.S. Appl. No. 11/807,048, filed May 25, 2007.

(Continued)

*Primary Examiner* — Ganapathirama Raghu
(74) *Attorney, Agent, or Firm* — Squire Patton Boggs LLP

(57) ABSTRACT

Provided herein are methods for a robust production of isoprenoids via one or more biosynthetic pathways. Also provided herein are nucleic acids, enzymes, expression vectors, and genetically modified host cells for carrying out the subject methods. Also provided herein are fermentation methods for high productivity of isoprenoids from genetically modified host cells.

15 Claims, 30 Drawing Sheets

Specification includes a Sequence Listing.

(56) References Cited

OTHER PUBLICATIONS

U.S.P.T.O. Non-Final Office Action dated Dec. 5, 2008, for U.S. Appl. No. 11/807,048, filed May 25, 2007.
"Maximum Dissolved Oxygen Concentration Saturation Table" taken from: http://dnr.mo.govienviesp/wqm/DOSaturationTable.htm, 1 page.
Choi et al. "Restricted electron flux increases coenzyme $Q_{10}$ production in *Agrobacterium tumefaciens* ATCC4452," *Process Biochemistry*, 2005, vol. 40, pp. 3225-3229.
Gupta et al. "A Study of Oxygen Transfer in Shake Flasks Using a Non-Invasive Oxygen Sensor," *Biotechnology and Bioengineering*, Nov. 5, 2003, vol. 84, No. 3, pp. 351-358.
Kaplan et al. "Effect of Oxygen on Ubiquinone-10 Production by *Paracoccus denitrificans*," *Biotechnology Letters*, Oct. 1993, vol. 15, No. 10, pp. 1001-1002.
Martin et al. "Engineering a mevalonate pathway in *Escherichia coli* for production of terpenoids," *Nature Biotechnology*, Jul. 2003, vol. 21, No. 7, pp. 796-802.
Newman et al. "High-level production of amorpha-4,11-diene in a two-phase partitioning bioreactor of metabolically engineered *Escherichia coli*," *Biotechnology and Bioengineering*, Nov. 2006, vol. 95, No. 4, pp. 684-691.
Vasala et al. "A new wireless system for decentralised measurement of physiological parameters from shake flasks," *Microbial Cell Factories*, 2006, vol. 5, No. 8 (6 pages).
"Facts and Evidence and Arguments in support of Opposition" filed by Ajinomoto Co., Inc. against EP Patent No. 2217711, dated May 25, 2016, 61 pages.
Letter to the European Patent Office dated Nov. 22, 2017 by Ajinomoto, Co., for Opposition to European Patent No. 2217711 for submission of further documents, 8 pages.
Operating instructions for Hamilton OxyFerm™ DO sensors, 2016, 7 pages.
A guide to conductivity and dissolved oxygen, Mettler-Toledo (Rev. D2/97), 4 pages.
Response to the Summons to the European Patent Office dated Nov. 7, 2017 by Ajinomoto, Co., along with the facts and evidence and arguments in support of Opposition, to European Patent No. 2217711, 63 pages.
Luttik, M. et al. 1998. "The *Saccharomyces cerevisiae* NDE1 and NDE2 Genes Encode Separate Mitochondrial NADH Dehydrogenases Catalyzing the Oxidation of Cytosolic NADH." *The Journal of Biological Chemistry* 273(38):24529-24534.
Sonderegger, M. and U. Sauer. 2003. "Evolutionary Engineering of *Saccharomyces cerevisiae* for Anaerobic Growth on Xylose." *Applied and Environmental Microbiology* 69(4):1990-1998.
Song, "A Soluble Form of Phosphatase in *Saccharomyces cerevisiae* Capable of Converting Farnesyl Diphosphate Into E,E-Farnesol", Applied Biochemistry and Biotechnology, vol. 128, 2006, pp. 149-157.
Stanbury, P.F. et al. 1995. *Principles of Fermentation Technology*. Elsevier Science Ltd. (Burlington, Massachusetts), pp. 222-223.

\* cited by examiner

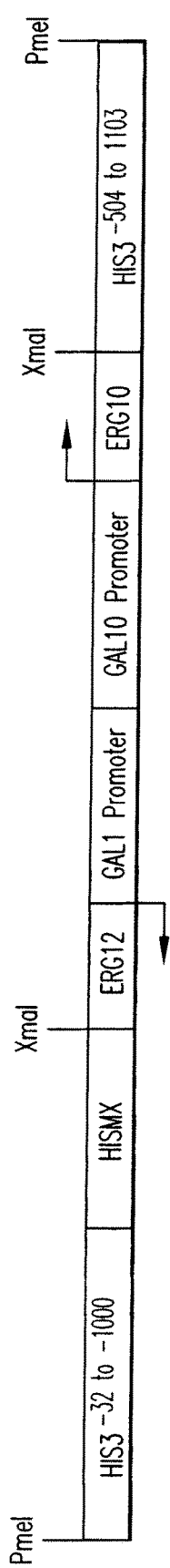
FIG.4D
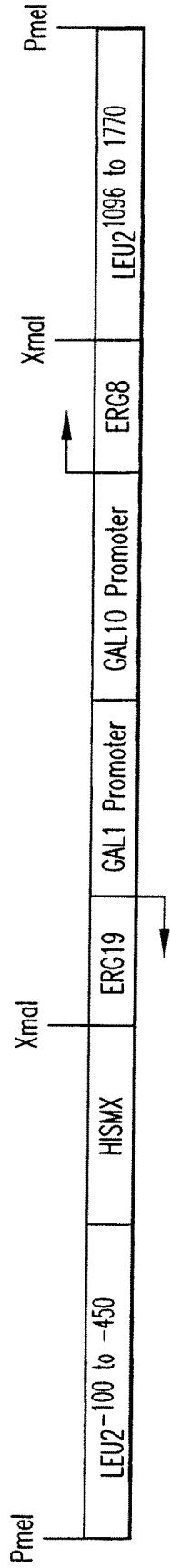
FIG.4E
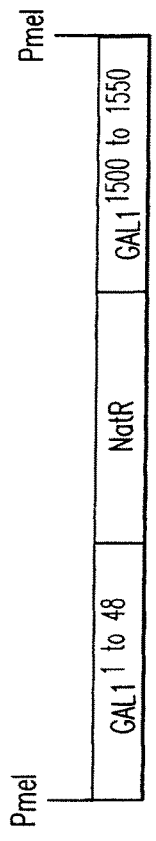
FIG.4F
FIG.4G

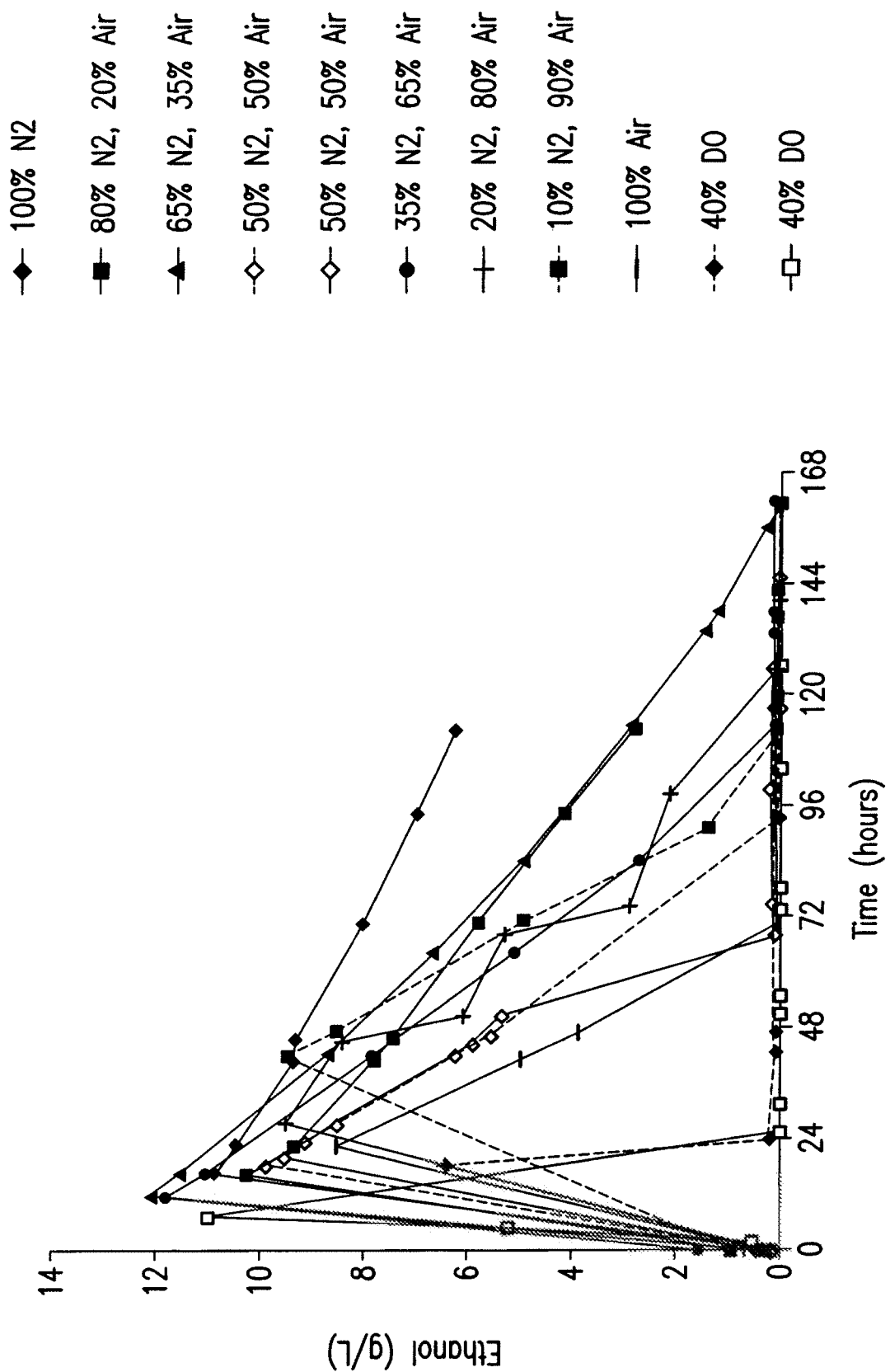

SEQUENCE LISTING

<160> NUMBER OF SEQ ID NOS: 73

<210> SEQ ID NO 1
<211> LENGTH: 5050
<212> TYPE: DNA
<213> ORGANISM: Artificial Sequence
<220> FEATURE:
<223> OTHER INFORMATION: ERG20-PGAL-tHMGR insert of pAM489

<400> SEQUENCE: 1

```
gtttaaacta ctattagctg aattgccact gctatcgttg ttagtggcgt tagtgcttgc      60
attcaaagac atggagggcg ttattacgcc ggagctcctc gacagcagat ctgatgactg     120
gtcaatatat ttttgcattg aggctctgtt tggaattata ttttgagatg acccatctaa     180
tgtactggta tcaccagatt tcatgtcgtt ttttaaagcg gctgcttgag tcttagcaat     240
agcgtcacca tctggtgaat cctttgaagg aaccactgac gaaggtttgg acagtgacga     300
agaggatctt tcctgctttg aattagtcgc gctgggagca gatgacgagt tggtggagct     360
gggggcagga ttgctggccg tcgtgggtcc tgaatgggtc cttggctggt ccatctctat     420
tctgaaaacg gaagaggagt agggaatatt actggctgaa ataagtctt gaatgaacgt      480 atacgcgtat atttctacca atctctcaac actgagtaat ggtagttata agaaagagac     540
cgagttaggg acagttagag gcggtggaga tattccttat ggcatgtctg gcgatgataa     600 aactttttcaa acggcagccc cgatctaaaa gagctgacac ccgggttaaa aaaaatcctt    660
ggactagtca cgtggaacgg tagatcgaga gatactatct taaagcttat actatattat     720
attggaagta tatagttctt atacatggtc cttatctagt ttgaaatcta atgttttatc     780
gattagcgtt agttctattt gcttctcttg taaactttgt tcaagaacgc agttaagaca     840
tcagctttga agccacgaga ctcatcgacc tgagaaattt tggccttcaa atccttggca    900
atagactctt catattcgtg gtatagctgt tcaattttca agtcattgaa aatcttttg      960 catttggctt ctgcgactga gtccttctta ccgtaatttt cgtctaaagt ctttctttgt    1020
tctgcggaag caagttccaa tgccttgttg attacccaag aacatttgtt atcttggata    1080
tctgtaccga tcttaccgat ctgttctggg gtaccgaagc agtctaagta gtcatcttga    1140
atttggaagt attcacccaa tggaatcaag acatctctgg cttgtttcaa atccttttca    1200
tccgtgatac cggcaacgta catggccaat gcgacaggca agtagaaaga atagtaagca    1260
gtcttgaaag taactatgaa ggagtgcttc tttagggaga acttactcaa gtcgactttg    1320
tcttcaggtg cagtgattaa gtccatcaat tggcccaatt cggtttggaa ggtgacctca    1380
tggaacaatt cggtgatatc tatgtagtat ttttcgtttc tgaagtgaga tttcaaaagc    1440
ttgtagatag cagcctctaa catgaatgcg tcattgatgg caatttcccc aacttcagga    1500
```

```
accttgtacc aacatggttg gcctcttctg gtaatggact tgtccatcat atcatcggcg   1560
accaagaagt aagcctgcaa caactcaatg caccaaccta gaatggcaac cttttcgtat   1620
tcttcttgcc ccaattgttc aacggtcttg ttggagagaa tagcatacgt gtccacaacg   1680
gacaaacctc tatttagctt accgcctgga gtgttgtagt tcaatgagtg ggcataccag   1740
tcacatgctt ccttaggcat accgtaagcc aaaagcgatg cgttcaattc ctctactaat   1800
ttagggaaaa cgttcaagaa tctctctctc ctaatttctt tttctgaagc catttatatt   1860
gaattttcaa aaattcttac ttttttttg gatggacgca aagaagttta ataatcatat   1920
tacatggcaa taccaccata tacatatcca tatctaatct tacttatatg ttgtggaaat   1980
gtaaagagcc ccattatctt agcctaaaaa aaccttctct ttggaactttt cagtaatacg   2040 cttaactgct cattgctata ttgaagtacg gattagaagc cgccgagcgg gcgacagccc   2100
tccgacggaa gactctcctc cgtgcgtcct ggtcttcacc ggtcgcgttc ctgaaacgca   2160
gatgtgcctc gcgccgcact gctccgaaca ataaagattc tacaatacta gcttttatgg   2220
ttatgaagag gaaaaattgg cagtaacctg gccccacaaa ccttcaaatc aacgaatcaa   2280
attaacaacc ataggataat aatgcgatta gttttttagc cttatttctg gggtaattaa   2340
tcagcgaagc gatgattttt gatctattaa cagatatata aatgcaaaag ctgcataacc   2400
actttaacta atactttcaa cattttcggt ttgtattact tcttattcaa atgtcataaa   2460
agtatcaaca aaaaattgtt aatatacctc tatactttaa cgtcaaggag aaaaaactat   2520
aatggctgca gaccaattgg tgaagactga agtcaccaag aagtctttta ctgctcctgt   2580
acaaaaggct tctacaccag ttttaaccaa taaaacagtc atttctggat cgaaagtcaa   2640
aagtttatca tctgcgcaat cgagctcatc aggaccttca tcatctagtg aggaagatga   2700
ttcccgcgat attgaaagct tggataagaa atacgtcct ttagaagaat tagaagcatt   2760
attaagtagt ggaaatacaa acaattgaa gaacaaagag gtcgctgcct tggttattca   2820
cggtaagtta cctttgtacg ctttggagaa aaaattaggt gatactacga gagcggttgc   2880
ggtacgtagg aaggctcttt caattttggc agaagctcct gtattagcat ctgatcgttt   2940
accatataaa aattatgact acgaccgcgt atttggcgct tgttgtgaaa atgttatagg   3000
ttacatgcct ttgcccgttg gtgttatagg ccccttggtt atcgatggta catcttatca   3060
tataccaatg gcaactacag agggttgttt ggtagcttct gccatgcgtg gctgtaaggc   3120
aatcaatgct ggcggtggtg caacaactgt tttaactaag gatggtatga caagaggccc   3180
agtagtccgt ttcccaactt tgaaaagatc tggtgcctgt aagatatggt tagactcaga   3240
agagggacaa aacgcaatta aaaaagcttt taactctaca tcaagatttg cacgtctgca   3300
acatattcaa acttgtctag caggagattt actcttcatg agatttagaa caactactgg   3360
tgacgcaatg ggtatgaata tgatttctaa gggtgtcgaa tactcattaa agcaaatggt   3420
agaagagtat ggctgggaag atatggaggt tgtctccgtt tctggtaact actgtaccga   3480
caaaaaacca gctgccatca actggatcga aggtcgtggt aagagtgtcg tcgcagaagc   3540
tactattcct ggtgatgttg tcagaaaagt gttaaaaagt gatgtttccg cattggttga   3600
gttgaacatt gctaagaatt tggttggatc tgcaatggct gggtctgttg gtggatttaa   3660
cgcacatgca gctaatttag tgacagctgt tttcttggca ttaggacaag atcctgcaca   3720
aaatgtcgaa agttccaact gtataacatt gatgaaagaa gtggacggtg atttgagaat   3780
ttccgtatcc atgccatcca tcgaagtagg taccatcggt ggtggtactg ttctagaacc   3840
acaaggtgcc atgttggact tattaggtgt aagaggccca catgctaccg ctcctggtac   3900
```

```
caacgcacgt caattagcaa gaatagttgc ctgtgccgtc ttggcaggtg aattatcctt    3960
atgtgctgcc ctagcagccg gccatttggt tcaaagtcat atgacccaca acaggaaacc    4020
tgctgaacca acaaaaccta acaatttgga cgccactgat ataaatcgtt gaaagatgg     4080 gtccgtcacc tgcattaaat cctaaactta gtcatacgtc attggtattc tcttgaaaaa    4140
gaagcacaac agcaccatgt gttacgtaaa atatttactt tatagtttgt acgtcataat    4200
ttcttccata ttacaagttc gtgcatatat agaaagaatt ctgttgttgt aattgtcata    4260
actcccggga tatatgtgta ctttgcagtt atgacgccag atggcagtag tggaagatat    4320
tctttattga aaaatagctt gtcaccttac gtacaatctt gatccggagc ttttcttttt    4380
ttgccgatta agaattcggt cgaaaaaaga aaaggagagg gccaagaggg agggcattgg    4440
tgactattga gcacgtgagt atacgtgatt aagcacacaa aggcagcttg gagtatgtct    4500
gttattaatt tcacaggtag ttctggtcca ttggtgaaag tttgcggctt gcagagcaca    4560
gaggccgcag aatgtgctct agattccgat gctgacttgc tgggtattat atgtgtgccc    4620
aatagaaaga gaacaattga cccggttatt gcaaggaaaa tttcaagtct tgtaaaagca    4680
tataaaaata gttcaggcac tccgaaatac ttggttggcg tgtttcgtaa tcaacctaag    4740
gaggatgttt tggctctggt caatgattac ggcattgata tcgtccaact gcatggagat    4800
gagtcgtggc aagaatacca agagttcctc ggtttgccag ttattaaaag actcgtattt    4860
ccaaaagact gcaacatact actcagtgca gcttcacaga aacctcattc gtttattccc    4920
ttgtttgatt cagaagcagg tgggacaggt gaacttttgg attggaactc gatttctgac    4980
tgggttggaa ggcaagagag ccccgaaagc ttacatttta tgttagctgg tggactgacg    5040
ccgtttaaac                                                           5050
```

<210> SEQ ID NO 2
<211> LENGTH: 5488
<212> TYPE: DNA
<213> ORGANISM: Artificial Sequence
<220> FEATURE:
<223> OTHER INFORMATION: ERG13-PGAL-tHMGR insert of pAM491

<400> SEQUENCE: 2

```
gtttaaactt gctaaattcg agtgaaacac aggaagacca gaaaatcctc atttcatcca      60
tattaacaat aatttcaaat gtttatttgc attatttgaa actagggaag acaagcaacg     120
aaacgttttt gaaatttttg agtattttca ataaatttgt agaggactca gatattgaaa     180
aaaagctaca gcaattaata cttgataaga agagtattga gaagggcaac ggttcatcat     240
ctcatggatc tgcacatgaa caaacaccag agtcaaacga cgttgaaatt gaggctactg     300
cgccaattga tgcacaataca gacgatgata acaaaccgaa gttatctgat gtagaaaagg     360
attaaagatg ctaagagata gtgatgatat tcataaaata atgtaattct atatatgtta     420 attaccttt ttgcgaggca tatttatggt gaaggataag ttttgaccat caaagaaggt     480
taatgtggct gtggtttcag ggtccatacc cgggtatata tatcattg ttattaaata     540 aagagtttc ctagtatata gattaaaaaa ctactctatt aaatgagagc taaaaaaagc     600
aggctgccaa aaaataaag catttatgaa gggggttcag caagatgcaa tcgatggggg     660
aagattattt tttaacatcg taagatcttc taaatttgtc atcgatgttg gtcaagtagt     720
aaacaccact ttgcaaatgc tcaatggaac cttgaggttt gaagttcttc ttcaaatggg     780
cattttctct caattcgatg gcagcttcgt aatcctttgg agtttcggtg attctcttgg     840
```

```
ctaatttgtt agtaatatct aattccttga taatatgttg gacgtcacca acaatttgc    900
aagaatatag agatgcagct aaaccggaac cgtaagaaaa taaaccaaca cgcttgcctt    960
gtaagtcgtc agatccaaca tagtttaata gagatgcaaa ggcggcataa acagatgcgg   1020
tgtacatgtt acctgtgttt gttggaacaa tcaaagattg ggcaactctc tctttgtgga   1080
atggcttagc aacattaaca aaagtttttt caatgttctt atcggttaaa gattcgtcat   1140
aatcgcgagt agctaattcg gcgtcaactt ctgggaacaa ttgaggattg gctctgaaat   1200
cgttatatag taatctaccg tatgattttg tgaccaattt acaggttgga acatggaaaa   1260
cgttgtagtc gaaatatttc aaaacgttca aagcatccga accagcggga tcgctaacca   1320
accctttaga aatagccttc ttggaataac tcttgtaaac ttgatcaaga gccttgacgt   1380
aacaagttaa tgaaaaatga ccatcgacgt aaggatattc gctggtgaaa tctggcttgt   1440
aaaaatcgta ggcgtgttcc atgtaagaag ctcttacaga gtcaaataca attggagcat   1500
caggaccgat ccacatagca acagtaccgg caccaccggt tggtcttgcg gcacccttat   1560
cgtagatggc aatatcaccg caaactacaa tggcgtctct accatcccat gcgttagatt   1620
caatccagtt caaagagttg aacaacgcgt tggtaccacc gtaacaggca ttaagcgtgt   1680
caataccttc gacgtcagtg ttttcaccaa acaattgcat caagacagac ttgacagact   1740
tggacttgtc aatcagagtt tcagtaccga cttctaatct accaattttg ttggtgtcga   1800
tgttgtaact cttgatcaac ttagacaaaa cagttaggga catcgagtag atatcttctc   1860
tgtcattgac aaaagacatg ttggtttggc ccagaccaat tgtgtattta ccttgagaaa   1920
cgccatcaaa tttctctagc tcagattggt tgacacattg agttgggatg taaatttgga   1980
tacctttaat accgacattt tgaggtctgg ttttttgttc agcggtcttt tgttttttta   2040
gttcagtcat ttgcaagttt gtattgtgta attgttgttg cttttgcggc ctaagtcttc   2100
ctttaatacc acaccaacaa agtttagttg agagtttcat ttatattgaa ttttcaaaaa   2160
ttcttacttt ttttttggat ggacgcaaag aagtttaata atcatattac atggcaaatac  2220
caccatatac atatccatat ctaatcttac ttatatgttg tggaaatgta aagagcccca   2280
ttatcttagc ctaaaaaaac cttctctttg gaactttcag taatacgctt aactgctcat   2340
tgctatattg aagtacggat tagaagccgc cgagcgggcg acagccctcc gacggaagac   2400
tctcctccgt gcgtcctggt cttcaccggt cgcgttcctg aaacgcagat gtgcctcgcg   2460
ccgcactgct ccgaacaata aagattctac aatactagct tttatggtta tgaagaggaa   2520
aaattggcag taacctggcc ccacaaacct tcaaatcaac gaatcaaatt aacaaccata   2580
ggataataat gcgattagtt ttttagcctt atttctgggg taattaatca gcgaagcgat   2640
gatttttgat ctattaacag atatataaat gcaaaagctg cataaccact ttaactaata   2700
ctttcaacat tttcggtttg tattacttct tattcaaatg tcataaaagt atcaacaaaa   2760
aattgttaat atacctctat actttaacgt caaggagaaa aaactataat ggctgcagac   2820
caattggtga agactgaagt caccaagaag tcttttactg ctcctgtaca aaaggcttct   2880
acaccagttt taaccaataa aacagtcatt tctggatcga agtcaaaag tttatcatct    2940
gcgcaatcga gctcatcagg accttcatca tctagtgagg aagatgattc ccgcgatatt   3000
gaaagcttgg ataagaaaat acgtccttta gaagaattag aagcattatt aagtagtgga   3060
aatacaaaac aattgaagaa caaagaggtc gctgccttgg ttattcacgg taagttacct   3120
ttgtacgctt tggagaaaaa attaggtgat actacgagag cggttgcggt acgtaggaag   3180
gctctttcaa ttttggcaga agctcctgta ttagcatctg atcgtttacc atataaaaat   3240
```

```
tatgactacg accgcgtatt tggcgcttgt tgtgaaaatg ttataggtta catgcctttg    3300
cccgttggtg ttataggccc cttggttatc gatggtacat cttatcatat accaatggca    3360
actacagagg gttgtttggt agcttctgcc atgcgtggct gtaaggcaat caatgctggc    3420
ggtggtgcaa caactgtttt aactaaggat ggtatgacaa gaggcccagt agtccgtttc    3480
ccaactttga aaagatctgg tgcctgtaag atatggttag actcagaaga gggacaaaac    3540
gcaattaaaa aagcttttaa ctctacatca agatttgcac gtctgcaaca tattcaaact    3600
tgtctagcag gagatttact cttcatgaga tttagaacaa ctactggtga cgcaatgggt    3660
atgaatatga tttctaaggg tgtcgaatac tcattaaagc aaatggtaga agagtatggc    3720
tgggaagata tggaggttgt ctccgtttct ggtaactact gtaccgacaa aaaaccagct    3780
gccatcaact ggatcgaagg tcgtggtaag agtgtcgtcg cagaagctac tattcctggt    3840
gatgttgtca gaaaagtgtt aaaaagtgat gtttccgcat tggttgagtt gaacattgct    3900
aagaatttgg ttggatctgc aatggctggg tctgttggtg gatttaacgc acatgcagct    3960
aatttagtga cagctgtttt cttggcatta ggacaagatc ctgcacaaaa tgtcgaaagt    4020
tccaactgta taacattgat gaaagaagtg gacggtgatt tgagaatttc cgtatccatg    4080
ccatccatcg aagtaggtac catcggtggt ggtactgttc tagaaccaca aggtgccatg    4140
ttggacttat taggtgtaag aggcccacat gctaccgctc ctggtaccaa cgcacgtcaa    4200
ttagcaagaa tagttgcctg tgccgtcttg gcaggtgaat tatccttatg tgctgcccta    4260
gcagccggcc atttggttca aagtcatatg acccacaaca ggaaacctgc tgaaccaaca    4320
aaacctaaca atttggacgc cactgatata aatcgtttga aagatgggtc cgtcacctgc    4380
attaaatcct aaacttagtc atacgtcatt ggtattctct tgaaaaagaa gcacaacagc    4440
accatgtgtt acgtaaaata tttactttat agtttgtacg tcataatttc ttccatatta    4500
caagttcgtg catatataga aagaattctg ttgttgtaat tgtcataact cccgggaagc    4560
ttttcaattc atcttttttt ttttttgttct ttttttttgat tccggtttct ttgaaatttt    4620
tttgattcgg taatctccga gcagaaggaa gaacgaagga aggagcacag acttagattg    4680
gtatatatac gcatatgtgg tgttgaagaa acatgaaatt gcccagtatt cttaacccaa    4740
ctgcacagaa caaaacctg caggaaacga agataaatca tgtcgaaagc tacatataag    4800
gaacgtgctg ctactcatcc tagtcctgtt gctgccaagc tatttaatat catgcacgaa    4860
aagcaaacaa acttgtgtgc ttcattggat gttcgtacca ccaaggaatt actggagtta    4920
gttgaagcat taggtcccaa aatttgttta ctaaaaacac atgtggatat cttgactgat    4980
ttttccatgg agggcacagt taagccgcta aaggcattat ccgccaagta caatttttta    5040
ctcttcgaag acagaaaatt tgctgacatt ggtaatacag tcaaattgca gtactctgcg    5100
ggtgtataca gaatagcaga atgggcagac attacgaatg cacacggtgt ggtgggccca    5160
ggtattgtta gcggtttgaa gcaggcggcg gaagaagtaa caaaggaacc tagaggcctt    5220
ttgatgttag cagaattgtc atgcaagggc tccctagcta ctggagaata tactaagggt    5280
actgttgaca ttgcgaagag cgacaaagat tttgttatcg gctttattgc tcaaagagac    5340
atgggtggaa gagatgaagg ttacgattgg ttgattatga cacccggtgt gggtttagat    5400
gacaagggag acgcattggg tcaacagtat agaaccgtgg atgatgtggt ctctacagga    5460
tctgacatta ttattgttgg gtttaaac                                        5488
```

<210> SEQ ID NO 3
<211> LENGTH: 4933
<212> TYPE: DNA
<213> ORGANISM: Artificial Sequence
<220> FEATURE:
<223> OTHER INFORMATION: IDI1-PGAL-tHMGR insert of pAM493

<400> SEQUENCE: 3

```
gtttaaacta ctcagtatat taagtttcga attgaagggc gaactcttat tcgaagtcgg      60
agtcaccaca acacttccgc ccatactctc cgaatcctcg tttcctaaag taagtttact     120
tccacttgta ggcctattat taatgatatc tgaataatcc tctattaggg ttggatcatt     180
cagtagcgcg tgcgattgaa aggagtccat gcccgacgtc gacgtgatta gcgaaggcgc     240
gtaaccattg tcatgtctag cagctataga actaacctcc ttgacaccac ttgcggaagt     300
ctcatcaaca tgctcttcct tattactcat tctcttacca agcagagaat gttatctaaa     360
aactacgtgt atttcacctc tttctcgact tgaacacgtc caactcctta agtactacca     420
cagccaggaa agaatggatc cagttctaca cgatagcaaa gcagaaaaca caaccagcgt     480
acccctgtag aagcttcttt gtttacagca cttgatccat gtagccatac tcgaaatttc     540
aactcatctg aaacttttcc tgaaggttga aaaagaatgc cataagggtc acccgaagct     600
tattcacgcc cggtaaaata agaaaaataa agtttacata ttactaagga tttttgtcgc     660
ctatttttac tattttttcag gtgaaatgaa acgttttata tcacattttg ctatgataac     720
aaagttatta tgattttat gtagcctata ttattgacgc gttgttatag cattctatga     780
atttgcctgt cattttccac ttcagaaagg tcatctaatt gctcccacca gttgaataag     840
taattctcgc aaataatctt aaaccaaggc gtaaacttgt aacttgggtc agcaaacata     900
gttttcaaat catttggtga aacccatttg aagtctctaa cttcattgac gtttgggttg     960
acagtcaagt tttctttagc gttgatctta taaatagga tgtaatcaat ttcatgttca    1020
ccccatggtt cattgcttgg tgccatgtaa tggattctgt ttaaaaagtg aaacttaccc    1080
cttgtcttag tttcatcttc tggaatacct aattcatgat ctagttttct caccgccgca    1140
gtaatagcgc ccttaatctt atcgtctagc ttacccttca aacctaattc gtcatcaata    1200
catagtggat gagagcagca tgtgttagtc caaagatcag ggaaagttat tttttcagtg    1260
gctctttgtt gtaaaagtaa ttcacccttgt tcattgaaaa taaagacgga gaatgcacga    1320
tgtagtaaac ccttttcaat attttccatt aaatgacaaa cttcttggt accggcacca    1380
atagcattat cgtcccaatc caaaacaata caatttcat tcattaactt aatttgctcc    1440
tcatcatgac cagaaaaaca tgtttctccg ctttcgtcat ttgacgtctc actagatcgg    1500
gtattaggtc tttgttgtaa tggaataatt tcaggaaact cttccaaaat gtcttcaggt    1560
gtttggtttt gcactaattt ggcgtaacta gatactgcac catggggcat actattgttg    1620
tcggcagtca tttatattga attttcaaaa attcttactt tttttttgga tggacgcaaa    1680
gaagtttaat aatcatatta catggcatta ccaccatata catatccata tctaatctta    1740
cttatatgtt gtggaaatgt aaagagcccc attatcttag cctaaaaaaa ccttctcttt    1800
ggaactttca gtaatacgct taactgctca ttgctatatt gaagtacgga ttagaagccg    1860
ccgagcgggc gacagccctc cgacggaaga ctctcctccg tgcgtcctcg tcttcaccgg    1920
tcgcgttcct gaaacgcaga gtgcctcgc gccgcactgc tccgaacaat aaagattcta    1980
caatactagc ttttatggtt atgaagagga aaaattggca gtaacctggc cccacaaacc    2040
```

```
ttcaaattaa cgaatcaaat taacaaccat aggatgataa tgcgattagt ttttagcct    2100 tatttctggg gtaattaatc agcgaagcga tgattttga tctattaaca gatatataaa    2160
tggaaaagct gcataaccac tttaactaat actttcaaca ttttcagttt gtattacttc    2220
ttattcaaat gtcataaaag tatcaacaaa aaattgttaa tacctctta tactttaacg    2280 tcaaggagaa aaactataa tggctgcaga ccaattggtg aagactgaag tcaccaagaa     2340
gtcttttact gctcctgtac aaaaggcttc tacaccagtt ttaaccaata aaacagtcat    2400
ttctggatcg aaagtcaaaa gtttatcatc tgcgcaatcg agctcatcag gaccttcatc    2460
atctagtgag gaagatgatt cccgcgatat tgaaagcttg gataagaaaa tacgtccttt    2520
agaagaatta gaagcattat taagtagtgg aaatacaaaa caattgaaga acaaagaggt    2580
cgctgccttg gttattcacg gtaagttacc tttgtacgct ttggagaaaa aattaggtga    2640
tactacgaga gcggttgcgg tacgtaggaa ggctctttca attttggcag aagctcctgt    2700
attagcatct gatcgtttac catataaaaa ttatgactac gaccgcgtat ttggcgcttg    2760
ttgtgaaaat gttataggtt acatgccttt gcccgttggt gttataggcc ccttggttat    2820
cgatggtaca tcttatcata taccaatggc aactacagag ggttgtttgg tagcttctgc    2880
catgcgtggc tgtaaggcaa tcaatgctgg cggtggtgca acaactgttt taactaagga    2940
tggtatgaca agaggcccag tagtccgttt cccaactttg aaaagatctg gtgcctgtaa    3000
gatatggtta gactcagaag agggacaaaa cgcaattaaa aaagctttta actctacatc    3060
aagatttgca cgtctgcaac atattcaaac ttgtctagca ggagatttac tcttcatgag    3120
atttagaaca actactggtg acgcaatggg tatgaatatg atttctaagg gtgtcgaata    3180
ctcattaaag caaatggtag aagagtatgg ctgggaagat atggaggttg tctccgtttc    3240
tggtaactac tgtaccgaca aaaaccagc tgccatcaac tggatcgaag gtcgtggtaa     3300
gagtgtcgtc gcagaagcta ctattcctgg tgatgttgtc agaaaagtgt taaaaagtga    3360
tgtttccgca ttggttgagt tgaacattgc taagaatttg gttggatctg caatggctgg    3420
gtctgttggt ggatttaacg cacatgcagc taatttagtg acagctgttt tcttggcatt    3480
aggacaagat cctgcacaaa atgtcgaaag ttccaactgt ataacattga tgaaagaagt    3540
ggacggtgat ttgagaattt ccgtatccat gccatccatc gaagtaggta ccatcggtgg    3600
tggtactgtt ctagaaccac aaggtgccat gttggactta ttaggtgtaa gaggcccaca    3660
tgctaccgct cctggtacca acgcacgtca attagcaaga atagttgcct gtgccgtctt    3720
ggcaggtgaa ttatccttat gtgctgccct agcagccggc catttggttc aaagtctat    3780 gacccacaac aggaaacctg ctgaaccaac aaaacctaac aatttggacg ccactgatat    3840
aaatcgtttg aaagatgggt ccgtcacctg cattaaatcc taaacttagt catacgtcat    3900
tggtattctc ttgaaaaaga agcacaacag caccatgtgt tacgtaaaat atttacttta    3960
tagtttgtac gtcataattt cttccatatt acaagttcgt gcatatatag aaagaattct    4020
gttgttgtaa ttgtcataac tcccgggagt cagtctgact cttgcgagag atgaggatgt    4080
aataatacta atctcgaaga tgccatctaa tacatataga catacatata tatatatata    4140
cattctatat attcttaccc agattctttg aggtaagacg gttgggtttt atcttttgca    4200
gttggtacta ttaagaacaa tcgaatcata agcattgctt acaaagaata cacatacgaa    4260
atattaacga taatgtcaat tacgaagact gaactggacg gtatattgcc attggtggcc    4320
agaggtaaag ttagagacat atatgaggta gacgctggta cgttgctgtt tgttgctacg    4380
gatcgtatct ctgcatatga cgttattatg gaaaacagca ttcctgaaaa ggggatccta    4440
```

```
ttgaccaaac tgtcagagtt ctggttcaag ttcctgtcca acgatgttcg taatcatttg    4500
gtcgacatcg ccccaggtaa gactattttc gattatctac ctgcaaaatt gagcgaacca    4560
aagtacaaaa cgcaactaga agaccgctct ctattggttc acaaacataa actaattcca    4620
ttggaagtaa ttgtcagagg ctacatcacc ggatctgctt ggaaagagta cgtaaaaaca    4680
ggtactgtgc atggtttgaa acaacctcaa ggacttaaag aatctcaaga gttcccagaa    4740
ccaatcttca ccccatcgac caaggctgaa caaggtgaac atgacgaaaa catctctcct    4800
gcccaggccg ctgagctggt gggtgaagat ttgtcacgta gagtggcaga actggctgta    4860
aaactgtact ccaagtgcaa agattatgct aaggagaagg gcatcatcat cgcagacact    4920
aaattgttta aac                                                       4933
```

<210> SEQ ID NO 4
<211> LENGTH: 6408
<212> TYPE: DNA
<213> ORGANISM: Artificial Sequence
<220> FEATURE:
<223> OTHER INFORMATION: ERG10-PGAL-ERG12 insert of pAM495

<400> SEQUENCE: 4

```
gtttaaacta ttgtgagggt cagttatttc atccagatat aacccgagag gaaacttctt      60
agcgtctgtt ttcgtaccat aaggcagttc atgaggtata ttttcgttat tgaagcccag     120
ctcgtgaatg cttaatgctg ctgaactggt gtccatgtcg cctaggtacg caatctccac     180
aggctgcaaa ggttttgtct caagagcaat gttattgtgc accccgtaat tggtcaacaa     240
gtttaatctg tgcttgtcca ccagctctgt cgtaaccttc agttcatcga ctatctgaag     300
aaatttacta ggaatagtgc catggtacag caaccgagaa tggcaatttc tactcgggtt     360
cagcaacgct gcataaacgc tgttggtgcc gtagacatat tcgaagatag gattatcatt     420
cataagtttc agagcaatgt ccttattctg gaacttggat ttatggctct tttggtttaa     480
tttcgcctga ttcttgatct cctttagctt ctcgacgtgg gcctttttct tgccatatgg     540
atccgctgca cggtcctgtt ccctagcatg tacgtgagcg tatttccttt taaaccacga     600
cgctttgtct tcattcaacg tttcccattg tttttttcta ctattgcttt gctgtgggaa     660
aaacttatcg aaagatgacg acttttttctt aattctcgtt ttaagagctt ggtgagcgct     720
aggagtcact gccaggtatc gtttgaacac ggcattagtc agggaagtca taacacagtc     780
ctttcccgca attttctttt tctattactc ttggcctcct ctagtacact ctatattttt     840
ttatgcctcg gtaatgattt tcatttttt ttttccacc tagcggatga ctctttttt     900 ttcttagcga ttggcattat cacataatga attatacatt atataaagta atgtgatttc     960
ttcgaagaat atactaaagt ttagcttgcc tcgtccccgc cgggtcaccc ggccagcgac    1020
atggaggccc agaataccct ccttgacagt cttgacgtgc gcagctcagg ggcatgatgt    1080
gactgtcgcc cgtacattta gcccatacat ccccatgtat aatcatttgc atccatacat    1140
tttgatggcc gcacggcgcg aagcaaaaat tacggctcct cgctgcagac ctgcgagcag    1200
ggaaacgctc ccctcacaga cgcgttgaat tgtccccacg ccgcgcccct gtagagaaat    1260
ataaaaggtt aggatttgcc actgaggttc ttctttcata tacttccttt taaaatcttg    1320
ctaggataca gttctcacat cacatccgaa cataaacaac catggcagaa ccagcccaaa    1380
aaaagcaaaa acaaactgtt caggagcgca aggcgtttat ctcccgtatc actaatgaaa    1440
ctaaaattca aatcgctatt cgctgaatg gtggttatat tcaaataaaa gattcgattc    1500
```

```
ttcctgcaaa gaaggatgac gatgtagctt cccaagctac tcagtcacag gtcatcgata    1560
ttcacacagg tgttggcttt ttggatcata tgatccatgc gttggcaaaa cactctggtt    1620
ggtctcttat tgttgaatgt attggtgacc tgcacattga cgatcaccat actaccgaag    1680
attgcggtat cgcattaggg caagcgttca agaagcaat  gggtgctgtc cgtggtgtaa    1740
aaagattcgg tactgggttc gcaccattgg atgaggcgct atcacgtgcc gtagtcgatt    1800
tatctagtag accatttgct gtaatcgacc ttggattgaa gagagagatg attggtgatt    1860
tatccactga aatgattcca cacttttggg aaagtttcgc ggaggcggcc agaattactt    1920
tgcatgttga ttgtctgaga ggtttcaacg atcaccacag aagtgagagt gcgttcaagg    1980
ctttggctgt tgccataaga gaagctattt ctagcaatgg caccaatgac gttccctcaa    2040
ccaaggtgt  tttgatgtga agtactgaca ataaaaagat tcttgttttc aagaacttgt    2100
catttgtata gttttttat  attgtagttg ttctatttta atcaaatgtt agcgtgattt    2160
atattttttt tcgcctcgac atcatctgcc cagatgcgaa gttaagtgcg cagaaagtaa    2220
tatcatgcgt caatcgtatg tgaatgctgg tcgctatact gctgtcgatt cgatactaac    2280
gccgccatcc acccgggaaa agtaagtcaa aaggcacacc tcagcgtttg agtacctgaa    2340
aaacgatgaa tcgcaaataa aactttaaat tatgcctgtt atacataaag ccatttatat    2400
atttatgtat tttatgaaaa agatcatgag aaaatcgcag aacgtaatca tatcttttca    2460
atgacaatag aggaagcacc accaccacca ttacaaatgg cggcaacacc gatcttacct    2520
ccttcttgct gtaagatgga tagcagtgta caaccactc  tagcaccaga acaacccaat    2580
gggtgaccta gagcaacagc accaccatat acattaacct tagatgggtc tagcttcaaa    2640
atcttagtgt tcaccaaacc gacaaccgaa aaggcttcat tgaattcaaa gtaatcaaca    2700
gaattgatgt cttcgatgcc agcatgtttc aaagcctttg gaactgcaag agatggagcc    2760
catgtaaaat cagctggttg atgagcggcc tcaccccaac ctttgataat agccaaaggc    2820
ttcaaattct tttccttcaa aacttttcg  gaaaccaaga tgacggctgc agcaccatcg    2880
ttgattggag aagcgttagc ggcagtaaca gtaccgtttt ctttttggaa aacagtcctt    2940
gcagatctca attttcaac  gtgtaatcta gcaggttcct cgtccttcgt gacttgagta    3000
tcaggcttac ctctaaatcc cttaatggta acaggtacaa tttcattgtc gaatttacct    3060
tccttttgag attttggaga ttttggtag  gattcgatgg caaaattgtc ttgttgttct    3120
ctagtaatat cccaatcacg ggcacacttt tctgcgtgta cacccatggc tagaccatcg    3180
tacgcatcgt tcaacccatc tctttcgaca ccatcaacaa gaacagtttg gccaaatttg    3240
gcacccgcac gggctgctgg catgtagtat ggtgcgttag tcatagattc acaaccacca    3300
gctacgacaa catcagcatt accacatttg atggattgag cacccaaaat gattgccttc    3360
atagcggatg cacagacctt gttaactgtg cttgcaacga tatgattact caaaccggca    3420
gccaaagcaa cttgtctggc cggagcttgg cccaaattgg cagaaagaac gttaccaaaa    3480
ataatttcgt caaaatcctt ggatgcatcc aattctggaa ccttagccaa ggcgcctttt    3540
aaagcaacag cacccaattc cactgctgtc ttggaggata gagaaccctg aatgaaccca    3600
attggggttc tggcagtcga tacaatgtaa acgttctgag acatttatat tgaattttca    3660
aaaattctta cttttttttt ggatggacgc aaagaagttt aataatcata ttacatggca    3720
ataccaccat atacatatcc atatctaatc ttacttatat gttgtggaaa tgtaaagagc    3780
cccattatct tagcctaaaa aaaccttctc tttggaactt tcagtaatac gcttaactgc    3840
tcattgctat attgaagtac ggattagaag ccgccgagcg ggcgacagcc ctccgacgga    3900
```

```
agactctcct ccgtgcgtcc tggtcttcac cggtcgcgtt cctgaaacgc agatgtgcct    3960
cgcgccgcac tgctccgaac aataaagatt ctacaatact agcttttatg gttatgaaga    4020
ggaaaaattg gcagtaacct ggccccacaa accttcaaat caacgaatca aattaacaac    4080
cataggataa taatgcgatt agttttttag ccttatttct ggggtaatta atcagcgaag    4140
cgatgatttt tgatctatta acagatatat aaatgcaaaa gctgcataac cactttaact    4200
aatactttca acattttcgg tttgtattac ttcttattca aatgtcataa aagtatcaac    4260
aaaaaattgt taatataccct ctatacttta acgtcaagga gaaaaaacta taatgtcatt    4320
accgttctta acttctgcac cgggaaaggt tattattttt ggtgaacact ctgctgtgta    4380
caacaagcct gccgtcgctg ctagtgtgtc tgcgttgaga acctacctgc taataagcga    4440
gtcatctgca ccagatacta ttgaattgga cttcccggac attagcttta atcataagtg    4500
gtccatcaat gatttcaatg ccatcaccga ggatcaagta aactcccaaa aattggccaa    4560
ggctcaacaa gccaccgatg gcttgtctca ggaactcgtt agtctttttgg atccgttgtt    4620 agctcaacta tccgaatcct tccactacca tgcagcgttt tgtttcctgt atatgtttgt    4680
ttgcctatgc ccccatgcca agaatattaa gttttcttta aagtctactt tacccatcgg    4740
tgctgggttg ggctcaagcg cctctatttc tgtatcactg gccttagcta tggcctactt    4800 ggggggggtta ataggatcta atgacttgga aaagctgtca gaaaacgata agcatatagt    4860
gaatcaatgg gccttcatag gtgaaaagtg tattcacggt accccttcag gaatagataa    4920
cgctgtggcc acttatggta atgccctgct atttgaaaaa gactcacata atggaacaat    4980
aaacacaaac aattttaagt tcttagatga tttcccagcc attccaatga tcctaaccta    5040
tactagaatt ccaaggtcta caaaagatct tgttgctcgc gttcgtgtgt tggtcaccga    5100
gaaatttcct gaagttatga agccaattct agatgccatg ggtgaatgtg ccctacaagg    5160
cttagagatc atgactaagt taagtaaatg taaaggcacc gatgacgagg ctgtagaaac    5220
taataatgaa ctgtatgaac aactattgga attgataaga ataaatcatg gactgcttgt    5280
ctcaatcggt gtttctcatc ctggattaga acttattaaa aatctgagcg atgatttgag    5340
aattggctcc acaaaactta ccggtgctgg tggcggcggt tgctctttga cttttgttacg    5400 aagagacatt actcaagagc aaattgacag cttcaaaaag aaattgcaag atgattttag    5460
ttacgagaca tttgaaacag acttgggtgg gactggctgc tgtttgttaa gcgcaaaaaa    5520
tttgaataaa gatcttaaaa tcaaatcccct agtattccaa ttatttgaaa ataaaactac    5580
cacaaagcaa caaattgacg atctattatt gccaggaaac acgaatttac catggacttc    5640
ataagctaat ttgcgatagg cattatttat tagttgtttt taatcttaac tgtgtatgaa    5700
gttttatgta ataagatag aaagagaaac aaaaaaaaat ttttcgtagt atcaattcag    5760
ctttcgaaga cagaatgaaa tttaagcaga ccatcccggg agaggctagc agaattaccc    5820
tccacgttga ttgtctgcga ggcaagaatg atcatcaccg tagtgagagt gcgttcaagg    5880
ctcttgcggt tgccataaga gaagccacct cgcccaatgg taccaacgat gttccctcca    5940
ccaaaggtgt tcttatgtag tgacaccgat tatttaaagc tgcagcatac gatatatata    6000
catgtgtata tatgtatacc tatgaatgtc agtaagtatg tatacgaaca gtatgatact    6060
gaagatgaca aggtaatgca tcattctata cgtgtcattc tgaacgaggc gcgctttcct    6120 ttttttctttt tgcttttttct tttttttttct cttgaactcg agaaaaaaaa tataaaagag    6180
atggaggaac gggaaaaagt tagttgtggt gataggtggc aagtggtatt ccgtaagaac    6240
```

| | |
|---|---|
| aacaagaaaa gcatttcata ttatggctga actgagcgaa caagtgcaaa atttaagcat | 6300 |
| caacgcacaac aacgagaatg gttatgttcc tcctcactta agaggaaaac caagaagtgc | 6360 |
| cagaaataac agtagcaact acaataacaa caacggcggc gtttaaac | 6408 |

<210> SEQ ID NO 5
<211> LENGTH: 2357
<212> TYPE: DNA
<213> ORGANISM: Artificial Sequence
<220> FEATURE:
<223> OTHER INFORMATION: ERG8-PGAL-ERG19 insert of pAM497

<400> SEQUENCE: 5

| | |
|---|---|
| agattctaca atactagctt ttatggttat gaagaggaaa aattggcagt aacctggccc | 60 |
| cacaaacctt caaatcaacg aatcaaatta acaaccatag gataataatg cgattagttt | 120 |
| tttagcctta tttctggggt aattaatcag cgaagcgatg atttttgatc tattaacaga | 180 |
| tatataaatg caaaagctgc ataaccactt taactaatac tttcaacatt ttcggtttgt | 240 |
| attacttctt attcaaatgt cataaaagta tcaacaaaaa attgttaata tacctctata | 300 |
| ctttaacgtc aaggagaaaa aactataatg accgtttaca cagcatccgt taccgcaccc | 360 |
| gtcaacatcg caacccttaa gtattggggg aaaagggaca cgaagttgaa tctgcccacc | 420 |
| aattcgtcca tatcagtgac tttatcgcaa gatgacctca gaacgttgac ctctgcggct | 480 |
| actgcacctg agtttgaacg cgacactttg tggttaaatg gagaaccaca cagcatcgac | 540 |
| aatgaaagaa ctcaaaattg tctgcgcgac ctacgccaat taagaaagga atggaatcg | 600 |
| aaggacgcct cattgcccac attatctcaa tggaaactcc acattgtctc cgaaaataac | 660 |
| tttcctacag cagctggttt agcttcctcc gctgctggct ttgctgcatt ggtctctgca | 720 |
| attgctaagt ataccaatt accacagtca acttcagaaa tatctagaat agcaagaaag | 780 |
| gggtctggtt cagcttgtag atcgttgttt ggcggatacg tggcctggga atgggaaaa | 840 |
| gctgaagatg gtcatgattc catggcagta caaatcgcag acagtctga ctggcctcag | 900 |
| atgaaagctt gtgtcctagt tgtcagcgat attaaaaagg atgtgagttc cactcagggt | 960 |
| atgcaattga ccgtggcaac ctccgaacta tttaaagaaa gaattgaaca tgtcgtacca | 1020 |
| aagagatttg aagtcatgcg taaagccatt gttgaaaaag atttcgccac cttttgcaaag | 1080 |
| gaaacaatga tggattccaa ctcttttcca tgccacatgtt tggactcttt ccctccaata | 1140 |
| ttctacatga atgacacttc caagcgtatc atcagttggt gccacaccat taatcagttt | 1200 |
| tacggagaaa caatcgttgc atacacgttt gatgcaggtc aaatgctgt gttgtactac | 1260 |
| ttagctgaaa atgagtcgaa actctttgca tttatctata aattgtttgg ctctgttcct | 1320 |
| ggatgggaca agaaatttac tactgagcag cttgaggctt tcaaccatca atttgaatca | 1380 |
| tctaacttta ctgcacgtga attggatctt gagttgcaaa aggatgttgc cagagtgatt | 1440 |
| ttaactcaag tcggttcagg cccacaagaa acaaacgaat ctttgattga cgcaaagact | 1500 |
| ggtctaccaa aggaataaga tcaattcgat atgtaacatt tttcttttct tttctttcc | 1560 |
| tttttttaca atagctaatt tacgtttccc tacggtattg gtcggaacga ccaagcttca | 1620 |
| atttataaat atcttaattt taacagcagt taccacttga atgagaaacc cgggaaagat | 1680 |
| tctcttttt tatgatattt gtacataaac tttataaatg aaattcataa tagaaacgac | 1740 |
| acgaaattac aaaatggaat atgttcatag ggtagacgaa actatatacg caatctacat | 1800 |
| acatttatca agaggagaa aaggaggat gtaaggaat acaggtaagc aaattgatac | 1860 |
| taatggctca acgtgataag gaaaaagaat tgcacttta cattaatatt gacaaggagg | 1920 |

```
agggcaccac acaaaaagtt aggtgtaaca gaaaatcatg aaactatgat tcctaattta    1980
tatattggag gattttctct aaaaaaaaaa aaatacaaca aataaaaaac actcaatgac    2040
ctgaccattt gatggagttt aagtcaatac cttcttgaac catttcccat aatggtgaaa    2100
gttccctcaa gaattttact ctgtcagaaa cggcctaaac gacgtagtcg acctcctctt    2160
cagtactaaa tctaccaata ccaaatctga tggaagaatg ggctaatgca tcatccttac    2220
ccagcgcatg taaaacataa gaaggttcta gggaagcaga tgtacaggct gaacccgagg    2280
ataatgcgat atcccttagt gccatcaata aagattctcc ttccacgtag gcgaaagaaa    2340
cgttaacacg tttaaac                                                  2357

<210> SEQ ID NO 6
<211> LENGTH: 2121
<212> TYPE: DNA
<213> ORGANISM: Artificial Sequence
<220> FEATURE:
<223> OTHER INFORMATION: KanMX-PMET3 region from pAM328
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (2109)..(2109)
<223> OTHER INFORMATION: n is a, c, g, or t

<400> SEQUENCE: 6
gaattcgccc ttntggatgg cggcgttagt atcgaatcga cagcagtata gcgaccagca      60
ttcacatacg attgacgcat gatattactt tctgcgcact taacttcgca tctgggcaga     120
tgatgtcgag gcgaaaaaaa atataaatca cgctaacatt tgattaaaat agaacaacta     180
caatataaaa aaactataca aatgacaagt tcttgaaaac aagaatcttt ttattgtcag     240
tactgattag aaaaactcat cgagcatcaa atgaaactgc aatttattca tatcaggatt     300
atcaatacca tattttgaa aaagccgttt ctgtaatgaa ggagaaaact caccgaggca     360
gttccatagg atggcaagat cctggtatcg gtctgcgatt ccgactcgtc aacatcaat     420 acaacctatt aatttcccct cgtcaaaaat aaggttatca agtgagaaat caccatgagt     480
gacgactgaa tccggtgaga atggcaaaag cttatgcatt tctttccaga cttgttcaac     540
aggccagcca ttacgctcgt catcaaaatc actcgcatca accaaccgt tattcattcg     600 tgattgcgcc tgagcgagac gaaatacgcg atcgctgtta aaggacaat tacaaacagg     660 aatcgaatgc aaccggcgca ggaacactgc cagcgcatca acaatatttt cacctgaatc     720
aggatattct tctaatacct ggaatgctgt tttgccgggg atcgcagtgg tgagtaacca     780
tgcatcatca ggagtacgga taaaatgctt gatggtcgga agaggcataa attccgtcag     840
ccagtttagt ctgaccatct catctgtaac atcattggca acgctacctt tgccatgttt     900
cagaaacaac tctggcgcat cgggcttccc atacaatcga tagattgtcg cacctgattg     960
cccgacatta tcgcgagccc atttataccc atataaatca gcatccatgt tggaatttaa    1020
tcgcggcctc gaaacgtgag tctttttcctt acccatggtt gtttatgttc ggatgtgatg    1080
tgagaactgt atcctagcaa gatttttaaaa ggaagtatat gaaagaagaa cctcagtggc    1140
aaatcctaac cttttatatt tctctacagg ggcgcggcgt ggggacaatt caacgcgtct    1200
gtgaggggag cgtttccctg ctcgcaggtc tgcagcgagg agccgtaatt tttgcttcgc    1260
gccgtgcggc catcaaaatg tatggatgca aatgattata catggggatg tatgggctaa    1320
```

| | |
|---|---:|
| atgtacgggc gacagtcaca tcatgccct gagctgcgca cgtcaagact gtcaaggagg | 1380 |
| gtattctggg cctccatgtc gctggccggg tgacccggcg gggacgaggc aagctaaaca | 1440 |
| gatctgatct tgaaactgag taagatgctc agaatacccg tcaagataag agtataatgt | 1500 |
| agagtaaatat accaagtatt cagcatattc tcctcttctt ttgtataaat cacgaaggg | 1560 |
| atgatttata agaaaaatga atactattac acttcattta ccaccctctg atctagattt | 1620 |
| tccaacgata tgtacgtagt ggtataaggt gagggggtcc acagatataa catcgtttaa | 1680 |
| tttagtacta acagagactt ttgtcacaac tacatataag tgtacaaata tagtacagat | 1740 |
| atgacacact tgtagcgcca acgcgcatcc tacggattgc tgacagaaaa aaaggtcacg | 1800 |
| tgaccagaaa agtcacgtgt aattttgtaa ctcaccgcat tctagcggtc cctgtcgtgc | 1860 |
| acactgcact caacaccata aaccttagca acctccaaag gaaatcaccg tataacaaag | 1920 |
| ccacagtttt acaacttagt ctcttatgaa gttacttacc aatgagaaat agaggctctt | 1980 |
| tctcgagaaa tatgaaatatg gatatatata tatatatata tatatatata tatatatgta | 2040 |
| aacttggttc ttttttagct tgtgatctct agcttgggtc tctctctgtc gtaacagttg | 2100 |
| tgatatcgna agggcgaatt c | 2121 |

<210> SEQ ID NO 7
<211> LENGTH: 8425
<212> TYPE: DNA
<213> ORGANISM: Artificial Sequence
<220> FEATURE:
<223> OTHER INFORMATION: Plasmid pAM426

<400> SEQUENCE: 7

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatcga ctacgtcgta aggccgtttc tgacagagta aaattcttga gggaactttc | 240 |
| accattatgg gaaatgcttc aagaaggtat tgacttaaac tccatcaaat ggtcaggtca | 300 |
| ttgagtgttt tttatttgtt gtattttttt tttttagag aaaatcctcc aatatcaaat | 360 |
| taggaatcgt agtttcatga ttttctgtta cacctaactt tttgtgtggt gccctcctcc | 420 |
| ttgtcaatat taatgttaaa gtgcaattct ttttccttat cacgttgagc cattagtatc | 480 |
| aatttgctta cctgtattcc tttactatcc tcctttttct ccttcttgat aaatgtatgt | 540 |
| agattgcgta tatagtttcg tctaccctat gaacatattc cattttgtaa tttcgtgtcg | 600 |
| tttctattat gaatttcatt tataaagttt atgtacaaat atcataaaaa aagagaatct | 660 |
| ttttaagcaa ggattttctt aacttcttcg gcgacagcat caccgacttc ggtggtactg | 720 |
| ttggaaccac ctaaatcacc agttctgata cctgcatcca aaccttttt aactgcatct | 780 |
| tcaatggcct taccttcttc aggcaagttc aatgacaatt tcaacatcat tgcagcagac | 840 |
| aagatagtgg cgatagggtc aaccttattc tttggcaaat ctggagcaga accgtggcat | 900 |
| ggttcgtaca aaccaaatgc ggtgttcttg tctggcaaag aggccaagga cgcagatggc | 960 |
| aacaaaccca aggaacctgg gataacggag gcttcatcgg agatgatatc accaaacatg | 1020 |
| ttgctggtga ttataatacc atttaggtgg gttgggttct aactaggat catggcggca | 1080 |
| gaatcaatca attgatgttg aaccttcaat gtagggaatt cgttcttgat ggtttcctcc | 1140 |
| acagtttttc tccataatct tgaagaggcc aaaagattag cttatccaa ggaccaaata | 1200 |
| ggcaatggtg ctcatgttg tagggccatg aaagcggcca ttcttgtgat tctttgcact | 1260 |

```
tctggaacgg tgtattgttc actatcccaa gcgacaccat caccatcgtc ttcctttctc    1320
ttaccaaagt aaatacctcc cactaattct ctgacaacaa cgaagtcagt acctttagca    1380
aattgtggct tgattggaga taagtctaaa agagagtcgg atgcaaagtt acatggtctt    1440
aagttggcgt acaattgaag ttcttacgg attttagta aaccttgttc aggtctaaca    1500
ctaccggtac cccatttagg accagccaca gcacctaaca aaacggcatc aaccttcttg    1560
gaggcttcca gcgcctcatc tggaagtggg acacctgtag catcgatagc agcaccacca    1620
attaaatgat tttcgaaatc gaacttgaca ttggaacgaa catcagaaat agctttaaga    1680
accttaatgg cttcggctgt gatttcttga ccaacgtggt cacctggcaa aacgacgatc    1740
ttcttagggg cagacattac aatggtatat ccttgaaata tatataaaaa aaggcgcctt    1800
agaccgctcg gccaaacaac caattacttg ttgagaaata gagtataatt atcctataaa    1860
tataacgttt ttgaacacac atgaacaagg aagtacagga caattgattt tgaagagaat    1920
gtggattttg atgtaattgt tgggattcca ttttaataa ggcaataata ttaggtatgt    1980
ggatatacta gaagttctcc tcgaccgtcg atatgcggtg tgaaataccg cacagatgcg    2040
taaggagaaa ataccgcatc aggaaattgt aaacgttaat attttgttaa aattcgcgtt    2100 aaattttgt taaatcagct cattttttaa ccaataggcc gaaatcggca aaatccctta    2160
taaatcaaaa gaatagaccg ataggggtt gagtgttgtt ccagtttgga acaagagtcc    2220
actattaaag aacgtggact ccaacgtcaa agggcgaaaa accgtctatc agggcgatgg    2280
cccactacgt ggaagatccg aggcctagct ttaacgaacg cagaattttc gagttattaa    2340
acttaaaata cgctgaaccc gaacatagaa atatcgaatg ggaaaaaaaa actgcataaa    2400
ggcattaaaa gaggagcgaa ttttttttta ataaaaatct taataatcat taaaagataa    2460
ataatagtct atatatacgt atataaataa aaaatattca aaaaataaaa taaactatta    2520
ttttagcgta aaggatgggg aaagagaaaa gaaaaaaatt gatctatcga tttcaattca    2580
attcaattta tttcttttcg gataagaaag caacacctgg caattcctta ccttccaata    2640
attccaaaga agcaccacca ccagtagaga catgggagac ccgggccatg gttagataga    2700
catagggtaa actagcaatg atttgatcaa atgcttgtat tcatctccca ttctcgtaaa    2760
attgtcttta cctgcatatt ggacctctaa aaattggcaa agatatataa cagccataag    2820
taaaggtctt gggatattct ttgttgttaa atactctctg tttatgtctt tccaaacgtc    2880
ctccacttcc ttataaatca gtgtctgagc atattcttcg ttgacattgt attccttcat    2940
gtaagattct aaagagcttg aactatgttt tctctcctgt tccgctttat gagtcatcag    3000
gtcatttaat ctcctaccca gaataccact gtaacggaat aaaggcggag cagatacagc    3060
ccactcaact gattccttag tgaaaatatc gctcattcct agataacagg tagttgttag    3120
caagtttgca ccaccagtga taataactac gggatcgtgc tcttcagttg tcggtatgtg    3180
tccttcatta gcccatttcg cttctaccat tagattcctt acgaattctt taacgaactc    3240
cttcccacag ttgaataaat cagttctacc ttctttggcc agaaactcct ccatttctgt    3300
gtaggtatcc atgaataatt tgtaaatagg cttcatgtat tccggcaacg tgtctaagca    3360
ggtgatcgac catctttcca cggcttcagt gaaaatcttt aactcctcgt aagttccata    3420
tgcgtcatac gtgtcatcaa taagtgttat cacagcaact gccttagtga aaaaaactct    3480
agctcttgaa tactgggtt cgtaaccaga acctaaaccc caaaaatagc attcaacgat    3540
acgatctctc agacatgggg catttttctt aaatatcaaat gccttccacc acttgcatac    3600
```

```
gtgactcaac tcttccttat gtaggctctg caatagattg aactccagtt tagctaactt   3660
tagcagagtt ttattatggg agtcttgttg ctgatagaag ggtatgtact gggcggcctc   3720
gatccttggc aatctcttcc acaatggttg ctttaaagct ctctggattt cagtgaataa   3780
agcggggttt gtactaaacg cgtcctttgt cataatcgat agccttgatc ttgtgaatcc   3840
cagggcatct tcaagaatta tttcgcccgg aactctcatg gacgtagcct catataattc   3900
caacaatcct tcaacatcat tcgctaacga ttgtttaaaa gcaccattct tgtctttata   3960
gttattaaac acatcacacg tgacatagta tccttgttta cgcatcagcc taaaccataa   4020
gctagacctg tcgccattcc aattatcacc ataggtctcg taaatacatt gcaatgcatg   4080
atcaatttca cgttcaaaat gatacggaat acctaaacgt tgaatctcgt caatcagctt   4140
caacaaattt gcatgtttca taggaatatc caatgcttcc tttaacaact gtcttacttc   4200
cttctttaga tcgtttacta tttgctccac accctgttca acttgtttct cataaatcaa   4260
aaattgatcg ccccaaatag aaggtgggaa atttgcaatt ggccttatag gtttctcttc   4320
agtcaaggcc attgttttct gcagatccgg ggttttttct ccttgacgtt aaagtataga   4380
ggtatattaa caatttttg ttgatacttt tattacattt gaataagaag taatacaaac   4440
cgaaaatgtt gaaagtatta gttaaagtgg ttatgcagtt tttgcattta tatatctgtt   4500
aatagatcaa aaatcatcgc ttcgctgatt aattacccca gaaataaggc taaaaaacta   4560
atcgcattat catcctatgg ttgttaattt gattcgttca tttgaaggtt tgtggggcca   4620
ggttactgcc aattttttcct cttcataacc ataaaagcta gtattgtaga atctttattg   4680
ttcggagcag tgcggcgcga ggcacatctg cgtttcagga acgcgaccgg tgaagacgag   4740
gacgcacgga ggagagtctt ccttcggagg gctgtcaccc gctcggcggc ttctaatccg   4800
tactaagatc tgctttaatt tggccggcga acgtggcgag aaaggaaggg aagaaagcga   4860
aaggagcggg cgctagggcg ctggcaagtg tagcggtcac gctgcgcgta accaccacac   4920
ccgccgcgct taatgcgccg ctacaggcg cgtcgcgcca ttcgccattc aggctgcgca   4980
actgttggga agggcgatcg gtgcgggcct cttcgctatt acgccagctg cattaatgaa   5040
tcggccaacg cgcggggaga ggcggttttgc gtattgggcg ctcttccgct tcctcgctca   5100
ctgactcgct gcgctcggtc gttcggctgc ggcgagcggt atcagctcac tcaaaggcgg   5160
taatacggtt atccacagaa tcaggggata acgcaggaaa gaacatgtga gcaaaaggcc   5220
agcaaaaggc caggaaccgt aaaaaggccg cgttgctggc gtttttccat aggctccgcc   5280
cccctgacga gcatcacaaa aatcgacgct caagtcagag gtggcgaaac ccgacaggac   5340
tataaagata ccaggcgttt ccccctggaa gctccctcgt gcgctctcct gttccgaccc   5400
tgccgcttac cggatacctg tccgcctttc tcccttcggg aagcgtggcg ctttctcata   5460
gctcacgctg taggtatctc agttcggtgt aggtcgttcg ctccaagctg ggctgtgtgc   5520
acgaaccccc cgttcagccc gaccgctgcg ccttatccgg taactatcgt cttgagtcca   5580
acccggtaag acacgactta tcgccactgg cagcagccac tggtaacagg attagcagag   5640
cgaggtatgt aggcggtgct acagagttct tgaagtggtg gcctaactac ggctacacta   5700
gaaggacagt atttggtatc tgcgctctgc tgaagccagt taccttcgga aaaagagttg   5760
gtagctcttg atccggcaaa caaaccaccg ctggtagcgg tggtttttttt gtttgcaagc   5820
agcagattac gcgcagaaaa aaaggatctc aagaagatcc tttgatcttt tctacggggt   5880
ctgacgctca gtggaacgaa aactcacgtt aagggatttt ggtcatgaga ttatcaaaaa   5940
ggatcttcac ctagatcctt ttaaattaaa aatgaagttt taaatcaatc taaagtatat   6000
```

```
atgagtaaac ttggtctgac agttaccaat gcttaatcag tgaggcacct atctcagcga   6060
tctgtctatt tcgttcatcc atagttgcct gactcccgt  cgtgtagata actacgatac   6120
gggagggctt accatctggc cccagtgctg caatgatacc gcgagaccca cgctcaccgg   6180
ctccagattt atcagcaata aaccagccag ccggaagggc cgagcgcaga agtggtcctg   6240
caactttatc cgcctccatc cagtctatta attgttgccg ggaagctaga gtaagtagtt   6300
cgccagttaa tagtttgcgc aacgttgttg ccattgctac aggcatcgtg gtgtcacgct   6360
cgtcgtttgg tatggcttca ttcagctccg gttcccaacg atcaaggcga gttacatgat   6420
cccccatgtt gtgcaaaaaa gcggttagct ccttcggtcc tccgatcgtt gtcagaagta   6480
agttggccgc agtgttatca ctcatggtta tggcagcact gcataattct cttactgtca   6540
tgccatccgt aagatgcttt tctgtgactg gtgagtactc aaccaagtca ttctgagaat   6600
agtgtatgcg gcgaccgagt tgctcttgcc cggcgtcaat acgggataat accgcgccac   6660
atagcagaac tttaaaagtg ctcatcattg gaaaacgttc ttcggggcga aaactctcaa   6720
ggatcttacc gctgttgaga tccagttcga tgtaacccac tcgtgcaccc aactgatctt   6780
cagcatcttt tactttcacc agcgtttctg ggtgagcaaa aacaggaagg caaaatgccg   6840
caaaaaaggg aataagggcg acacggaaat gttgaatact catactcttc ctttttcaat   6900
attattgaag catttatcag ggttattgtc tcatgagcgg atacatattt gaatgtattt   6960
agaaaaataa acaaataggg gttccgcgca catttccccg aaaagtgcca cctgaacgaa   7020
gcatctgtgc ttcattttgt agaacaaaaa tgcaacgcga gagcgctaat ttttcaaaca   7080
aagaatctga gctgcatttt tacagaacag aaatgcaacg cgaaagcgct attttaccaa   7140
cgaagaatct gtgcttcatt tttgtaaaac aaaaatgcaa cgcgagagcg ctaattttc   7200 aaacaaagaa tctgagctgc attttacag  aacagaaatg caacgcgaga gcgctatttt   7260
accaacaaag aatctatact cttttttgt  tctacaaaaa tgcatcccga gagcgctatt   7320
tttctaacaa agcatcttag attactttt  ttctcctttg tgcgctctat aatgcagtct   7380
cttgataact ttttgcactg taggtccgtt aaggttagaa gaaggctact ttggtgtcta   7440
ttttctcttc cataaaaaaa gcctgactcc acttcccgcg tttactgatt actagcgaag   7500
ctgcgggtgc atttttcaa  gataaaggca tccccgatta tattctatac cgatgtggat   7560
tgcgcatact ttgtgaacag aaagtgatag cgttgatgat tcttcattgg tcagaaaatt   7620
atgaacggtt tcttctattt tgtctctata tactacgtat aggaaatgtt tacattttcg   7680
tattgttttc gattcactct atgaatagtt cttactacaa ttttttttgtc taaagagtaa   7740 tactagagat aaacataaaa aatgtagagg tcgagtttag atgcaagttc aaggagcgaa   7800
aggtggatgg gtaggttata tagggatata gcacagagat atatagcaaa gagatacttt   7860
tgagcaatgt ttgtggaagc ggtattcgca atatttagt  agctcgttac agtccggtgc   7920
gtttttggtt tttgaaagt  gcgtcttcag agcgcttttg gttttcaaaa gcgctctgaa   7980
gttcctatac tttctagaga ataggaactt cggaatagga acttcaaagc gtttccgaaa   8040
acgagcgctt ccgaaaatgc aacgcgagct gcgcacatac agctcactgt tcacgtcgca   8100
cctatatctg cgtgttgcct gtatatatat atacatgaga agaacggcat agtgcgtgtt   8160
tatgcttaaa tgcgtactta tatgcgtcta tttatgtagg atgaaaggta gtctagtacc   8220
tcctgtgata ttatcccatt ccatgcgggg tatcgtatgc ttccttcagc actacccttt   8280
agctgttcta tatgctgcca ctcctcaatt ggattagtct catccttcaa tgctatcatt   8340
```

```
tcctttgata ttggatcata ctaagaaacc attattatca tgacattaac ctataaaaat    8400
aggcgtatca cgaggccctt tcgtc                                          8425

<210> SEQ ID NO 8
<211> LENGTH: 1763
<212> TYPE: DNA
<213> ORGANISM: Artificial Sequence
<220> FEATURE:
<223> OTHER INFORMATION: DNA fragment GAL80-50 to -1-NatR- GAL801309 to
      1358

<400> SEQUENCE: 8
ccagcgtata caatctcgat agttggtttc ccgttctttc cactcccgtc cacaggaaac      60
agctatgacc atgattacgc caagcttggt accgagctcg gatccactag taacggccgc     120
cagtgtgctg gaattcgccc ttgtcgacac tagtaataca catcatcgtc ctacaagttc     180
atcaaagtgt tggacagaca actataccag catggatctc ttgtatcggt tcttttctcc     240
cgctctctcg caataacaat gaacactggg tcaatcatag cctacacagg tgaacagagt     300
agcgtttata cagggtttat acggtgattc ctacggcaaa aatttttcat ttctaaaaaa     360 aaaagaaaa attttctttt ccaacgctag aaggaaaaga aaatctaat taaattgatt     420 tggtgatttt ctgagagttc cctttttcat atatcgaatt tgaatataaa aaggagatcg     480
aaaaaatttt tctattcaat ctgttttctg gttttatttg atagtttttt tgtgtattat     540
tattatggat tagtactggt ttatatgggt ttttctgtat aacttctttt tattttagtt     600
tgtttaatct tattttgagt tacattatag ttccctaact gcaagagaag taacattaaa     660
aatgaccact cttgacgaca cggcttaccg gtaccgcacc agtgtcccgg gggacgccga     720
ggccatcgag gcactggatg gtccttcac caccgacacc gtcttccgcg tcaccgccac     780
cggggacggc ttcacccctg cggaggtgcc ggtggacccg cccctgacca aggtgttccc     840
cgacgacgaa tcggacgacg aatcggacgc cggggaggac ggcgacccgg actcccggac     900
gttcgtcgcg tacggggacg acggcgacct ggcgggcttc gtggtcgtct cgtactccgg     960
ctggaaccgc cggctgaccg tcgaggacat cgaggtcgcc ccggagcacc ggggcacgg    1020 ggtcgggcgc gcgttgatgg ggctcgcgac ggagttcgcc cgcgagcggg gcgccgggca    1080
cctctggctg gaggtcacca acgtcaacgc accggcgatc cacgcgtacc ggcggatggg    1140
gttcacccct gcggcctgg acaccgccct gtacgacggc accgcctcgg acggcgagca    1200
ggcgctctac atgagcatgc cctgcccctg agtttaactt gatactacta gattttttct    1260
cttcatttat aaaattttg gttataattg aagctttaga agtatgaaaa aatccttttt    1320
tttcattctt tgcaaccaaa ataagaagct tcttttattc attgaaatga tgaatataaa    1380
cctaacaaaa gaaaaagact cgaatatcaa acattaaaaa aaaataaaag aggttatctg    1440
ttttcccatt tagttggagt ttgcattttc taatagatag aactctcaat taatgtggat    1500
ttagtttctc tgttcgtttt tttttgtttt gttctcactg tatttacatt tctatttagt    1560
atttagttat tcatataatc ttaacttctc gaggagctca agggcaattc tgcagatatc    1620
catcacactg gcggccgctc gagcatgcat ctagagggcc caattcgccc tatagtgagt    1680
cgtattacaa ttcactggcc gtcgttttac aacaagcatc ttgccctgtg cttggccccc    1740
agtgcagcga acgttataaa aac                                           1763
```

<210> SEQ ID NO 9
<211> LENGTH: 3901
<212> TYPE: DNA
<213> ORGANISM: Artificial Sequence
<220> FEATURE:
<223> OTHER INFORMATION: GAL74 to 1021-HPH- GAL11637 to 2587 insert of pAM584

<400> SEQUENCE: 9

```
gtttaaacga ggctcaccta acaattcaaa accaaccaag aatttccgaa cagtagctga      60
tctcagtaaa ggtgggtaga aatgcatgtg aaaccaacta ttactcaatt catcaccagt     120
cgcattcaaa ggagcctgat ggatacccat tgagtatggg aaactcgttt caaataaatt     180
atcatactta atagttagtt gcttttaaaat cgaggcgagg tcctccttca ccatttggtt    240
aaattggcta attgaggcaa gcttcttctt tgaaatgacc aaggtctcaa atggccagat    300
ggcccagtat ggaacaacaa caataaagga ttcattctcc actacgactc ttgacttctc     360
tcttgattct aatttgacgt aatcggcaaa caaatcagta ttgtgttcac gtttatattt    420
atcaaaagat ttcaattctt gcgaaacttc actagggatg gattctaagc accaagcttg    480
gccatgtgga tgtaagttgg aacaacccat ggctgtacct ttgttttcaa atatttggac    540
atatttgaaa ggcttatgat tttctcttgc ttctctggag agatcgtcag tcaatgcttg    600
ccaagaatta acaatatgaa ccagatctga ttgtttcatt tgtggaatgg ttagattatg    660
attgggcta aacatatga cgaaacaatt gcctctcaca gattgcactt taagcagcct     720
atttttaaga ttatcctcat tggaatcatt ctgtggtaaa ataggttgat cgagcctaac    780
ggcagcataa tcattgggga aaatatacgt tgattcatat cttgggttta ggttaccagt    840
agctcttttg ttaccaggac atagatagca ttttggatca tacaatggag ctgtgggctt    900
gtaagcagcc tcctgttgac ctaaccaagg tcttttagct ctgtgtggag aaactaagat    960
ccatgaatcg gttagtggat tgtaacgtct atgggaatgg ctagaaaaat caaattcttc   1020
agcagtgtcg acactagtaa tacacatcat cgtcctacaa gttcatcaaa gtgttggaca   1080
gacaactata ccagcatgga tctcttgtat cggttctttt ctcccgctct ctcgcaataa   1140
caatgaacac tgggtcaatc atagcctaca caggtgaaca gagtagcgtt tatacagggt   1200
ttatacggtg attcctacgg caaaaatttt tcatttctaa aaaaaaaaag aaaaattttt   1260
ctttccaacg ctagaaggaa agaaaaaatc taattaaatt gatttggtga ttttctgaga   1320
gttcccttt tcatatatcg aattttgaat ataaaaggag atcgaaaaaa tttttctatt    1380
caatctgttt tctggtttta tttgatagtt tttttgtgta ttattattat ggattagtac   1440
tggtttatat gggttttttct gtataacttc tttttatttt agtttgttta atcttatttt   1500
gagttacatt atagttccct aactgcaaga gaagtaacat taaaaatgaa aaagcctgaa   1560
ctcaccgcga cgtctgtcga agtttctctg atcgaaaagt tcgacagcgt ctccgacctg   1620
atgcagctct cggagggcga agaatctcgt gctttcagct tcgatgtagg agggcgtgga   1680
tatgtcctgc gggtaaatag ctgcgccgat ggtttctaca agatcgtta tgtttatcgg   1740
cactttgcat cggccgcgct cccgattccg gaagtgcttg acattgggga attcagcgag   1800
agcctgacct attgcatctc ccgccgtgca cagggtgtca cgttgcaaga cctgcctgaa   1860
accgaactgc ccgctgttct gcagccggtc gcggaggcca tggatgcgat cgctgcggcc   1920
gatcttagcc agacgagcgg gttcggccca ttcggaccgc aaggaatcgg tcaatacact   1980
acatggcgtg atttcatatg cgcgattgct gatccccatg tgtatcactg gcaaactgtg   2040
```

```
atggacgaca ccgtcagtgc gtccgtcgcg caggctctcg atgagctgat gctttgggcc      2100
gaggactgcc ccgaagtccg gcacctcgtg cacgcggatt tcggctccaa caatgtcctg      2160
acggacaatg ccgcataaca gcggtcatt gactggagcg aggcgatgtt cggggattcc       2220
caatacgagg tcgccaacat cttcttctgg aggccgtggt tggcttgtat ggagcagcag      2280
acgcgctact tcgagcggag gcatccggag cttgcaggat cgccgcggct ccgggcgtat      2340
atgctccgca ttggtcttga ccaactctat cagagcttgg ttgacggcaa tttcgatgat      2400
gcagcttggg cgcagggtcg atgcgacgca atcgtccgat ccggagccgg gactgtcggg      2460
cgtacacaaa tcgcccgcag aagcgcggcc gtctggaccg atggctgtgt agaagtactc      2520
gccgatagtg gaaaccgacg ccccagcact cgtccgaggg caaggaata ggtttaactt       2580 gatactacta gatttttct cttcatttat aaaattttg gttataattg aagctttaga        2640
agtatgaaaa atcctttt tttcattctt tgcaaccaaa ataagaagct tcttttattc        2700
attgaaatga tgaatataaa cctaacaaaa gaaaagact cgaatatcaa acattaaaaa       2760
aaaataaaag aggttatctg ttttcccatt tagttggagt ttgcattttc taatagatag      2820
aactctcaat taatgtggat ttagtttctc tgttcgtttt ttttttgtttt gttctcactg    2880 tatttacatt tctatttagt atttagttat tcatataatc ttaacttctc gagactcata     2940
actttagcat cacaaaatac gcaataataa cgagtagtaa cacttttata gttcatacat     3000
gcttcaacta cttaataaat gattgtatga taatgttttc aatgtaagag atttcgatta    3060
tccacaaact ttaaaacaca gggacaaaat tcttgatatg ctttcaaccg ctgcgttttg     3120
gatacctatt cttgacatga tatgactacc attttgttat tgtacgtggg gcagttgacg     3180
tcttatcata tgtcaaagtc atttgcgaag ttcttggcaa gttgccaact gacgagatgc     3240
agtaaaaaga gattgccgtc ttgaaacttt ttgtcctttt tttttccgg ggactctacg      3300 agaaccctttt gtcctactga ttaattttgt actgaatttg gacaattcag attttagtag    3360
acaagcgcga ggaggaaaag aaatgacaga aaaattccga tggacaagaa gataggaaaa    3420
aaaaaaagct ttcaccgatt tcctagaccg gaaaaaagtc gtatgacatc agaatgaaaa    3480
attttcaagt tagacaagga caaaatcagg acaaattgta aagatataat aaactatttg    3540
attcagcgcc aatttgccct tttccatttt ccattaaatc tctgttctct cttacttata     3600
tgatgattag gtatcatctg tataaaactc ctttcttaat ttcactctaa agcataccc     3660 atagagaaga tctttcggtt cgaagacatt cctacgcata ataagaatag gagggaataa   3720
tgccagacaa tctatcatta catttaagcg gctcttcaaa aagattgaac tctcgccaac   3780
ttatggaatc ttccaatgag acctttgcgc caaataatgt ggatttggaa aaagagtata   3840
agtcatctca gagtaatata actaccgaag tttatgaggc atcgagcttt gaagtttaaa   3900
c                                                                     3901
```

<210> SEQ ID NO 10
<211> LENGTH: 66
<212> TYPE: DNA
<213> ORGANISM: Artificial Sequence
<220> FEATURE:
<223> OTHER INFORMATION: Primer 50-56-pw100-G

<400> SEQUENCE: 10

```
gagtgaacct gctgcctggc gtgctctgac tcagtacatt tcatagtgga tggcggcgtt     60
agtatc                                                                66
```

<210> SEQ ID NO 11
<211> LENGTH: 65
<212> TYPE: DNA
<213> ORGANISM: Artificial Sequence
<220> FEATURE:
<223> OTHER INFORMATION: Primer 50-56-pw101-G

<400> SEQUENCE: 11
cgtgtatacg ttttccgctt ctgctcttcg tcttttctct tcttccgata tcacaactgt    60
tacga                                                                65

<210> SEQ ID NO 12
<211> LENGTH: 30
<212> TYPE: DNA
<213> ORGANISM: Artificial Sequence
<220> FEATURE:
<223> OTHER INFORMATION: Primer 61-67-CPK001-G

<400> SEQUENCE: 12
gtttaaacta ctattagctg aattgccact                                      30

<210> SEQ ID NO 13
<211> LENGTH: 46
<212> TYPE: DNA
<213> ORGANISM: Artificial Sequence
<220> FEATURE:
<223> OTHER INFORMATION: Primer 61-67-CPK002-G

<400> SEQUENCE: 13
actgcaaagt acacatatat cccgggtgtc agctcttta gatcgg                     46

<210> SEQ ID NO 14
<211> LENGTH: 46
<212> TYPE: DNA
<213> ORGANISM: Artificial Sequence
<220> FEATURE:
<223> OTHER INFORMATION: Primer 61-67-CPK003-G

<400> SEQUENCE: 14
ccgatctaaa agagctgaca cccgggatat atgtgtactt tgcagt                    46

<210> SEQ ID NO 15
<211> LENGTH: 30
<212> TYPE: DNA
<213> ORGANISM: Artificial Sequence
<220> FEATURE:
<223> OTHER INFORMATION: Primer 61-67-CPK004-G

<400> SEQUENCE: 15
gtttaaacgg cgtcagtcca ccagctaaca                                      30

<210> SEQ ID NO 16
<211> LENGTH: 30
<212> TYPE: DNA
<213> ORGANISM: Artificial Sequence
<220> FEATURE:
<223> OTHER INFORMATION: Primer 61-67-CPK005-G

<400> SEQUENCE: 16
gtttaaactt gctaaattcg agtgaaacac                                      30

<210> SEQ ID NO 17
<211> LENGTH: 46
<212> TYPE: DNA
<213> ORGANISM: Artificial Sequence

```
<220> FEATURE:
<223> OTHER INFORMATION: Primer 61-67-CPK006-G

<400> SEQUENCE: 17
aaagatgaat tgaaaagctt cccgggtatg gaccctgaaa ccacag        46

<210> SEQ ID NO 18
<211> LENGTH: 46
<212> TYPE: DNA
<213> ORGANISM: Artificial Sequence
<220> FEATURE:
<223> OTHER INFORMATION: Primer 61-67-CPK007-

<400> SEQUENCE: 18
ctgtggtttc agggtccata cccgggaagc ttttcaattc atcttt        46

<210> SEQ ID NO 19
<211> LENGTH: 30
<212> TYPE: DNA
<213> ORGANISM: Artificial Sequence
<220> FEATURE:
<223> OTHER INFORMATION: Primer 61-67-CPK008-G

<400> SEQUENCE: 19
gtttaaaccc aacaataata atgtcagatc                          30

<210> SEQ ID NO 20
<211> LENGTH: 30
<212> TYPE: DNA
<213> ORGANISM: Artificial Sequence
<220> FEATURE:
<223> OTHER INFORMATION: Primer 61-67-CPK009-G

<400> SEQUENCE: 20
gtttaaacta ctcagtatat taagtttcga                          30

<210> SEQ ID NO 21
<211> LENGTH: 70
<212> TYPE: DNA
<213> ORGANISM: Artificial Sequence
<220> FEATURE:
<223> OTHER INFORMATION: Primer 61-67-CPK010-G

<400> SEQUENCE: 21
atctctcgca agagtcagac tgactcccgg gcgtgaataa gcttcgggtg acccttatgg    60
cattcttttt                                                          70

<210> SEQ ID NO 22
<211> LENGTH: 70
<212> TYPE: DNA
<213> ORGANISM: Artificial Sequence
<220> FEATURE:
<223> OTHER INFORMATION: Primer 61-67-CPK011-G

<400> SEQUENCE: 22
aaaaagaatg ccataagggt cacccgaagc ttattcacgc ccgggagtca gtctgactct    60
tgcgagagat                                                          70

<210> SEQ ID NO 23
<211> LENGTH: 30
<212> TYPE: DNA
<213> ORGANISM: Artificial Sequence
<220> FEATURE:
<223> OTHER INFORMATION: Primer 61-67-CPK012-G
```

```
<400> SEQUENCE: 23
gtttaaacaa tttagtgtct gcgatgatga                               30

<210> SEQ ID NO 24
<211> LENGTH: 30
<212> TYPE: DNA
<213> ORGANISM: Artificial Sequence
<220> FEATURE:
<223> OTHER INFORMATION: Primer 61-67-CPK013-G

<400> SEQUENCE: 24
gtttaaacta ttgtgagggt cagttatttc                               30

<210> SEQ ID NO 25
<211> LENGTH: 44
<212> TYPE: DNA
<213> ORGANISM: Artificial Sequence
<220> FEATURE:
<223> OTHER INFORMATION: Primer 61-67-CPK014alt-G

<400> SEQUENCE: 25
gcggggacga ggcaagctaa actttagtat attcttcgaa gaaa               44

<210> SEQ ID NO 26
<211> LENGTH: 44
<212> TYPE: DNA
<213> ORGANISM: Artificial Sequence
<220> FEATURE:
<223> OTHER INFORMATION: Primer 61-67-CPK015alt-G

<400> SEQUENCE: 26
tttcttcgaa gaatatacta agtttagct tgcctcgtcc ccgc                44

<210> SEQ ID NO 27
<211> LENGTH: 60
<212> TYPE: DNA
<213> ORGANISM: Artificial Sequence
<220> FEATURE:
<223> OTHER INFORMATION: Primer 61-67-CPK016-G

<400> SEQUENCE: 27
caatcaacgt ggagggtaat tctgctagcc tctcccgggt ggatggcggc gttagtatcg    60

<210> SEQ ID NO 28
<211> LENGTH: 60
<212> TYPE: DNA
<213> ORGANISM: Artificial Sequence
<220> FEATURE:
<223> OTHER INFORMATION: Primer 61-67-CPK017-G

<400> SEQUENCE: 28
cgatactaac gccgccatcc acccgggaga ggctagcaga attaccctcc acgttgattg    60

<210> SEQ ID NO 29
<211> LENGTH: 30
<212> TYPE: DNA
<213> ORGANISM: Artificial Sequence
<220> FEATURE:
<223> OTHER INFORMATION: Primer 61-67-CPK018-G

<400> SEQUENCE: 29
gtttaaacgc cgccgttgtt gttattgtag                               30

<210> SEQ ID NO 30
<211> LENGTH: 30
```

```
<212> TYPE: DNA
<213> ORGANISM: Artificial Sequence
<220> FEATURE:
<223> OTHER INFORMATION: Primer 61-67-CPK019-G

<400> SEQUENCE: 30
gtttaaactt ttccaatagg tggttagcaa                                30

<210> SEQ ID NO 31
<211> LENGTH: 55
<212> TYPE: DNA
<213> ORGANISM: Artificial Sequence
<220> FEATURE:
<223> OTHER INFORMATION: Primer 61-67-CPK020-G

<400> SEQUENCE: 31
gggtgacccg gcggggacga ggcaagctaa acgtcttcct ttctcttacc aaagt    55

<210> SEQ ID NO 32
<211> LENGTH: 55
<212> TYPE: DNA
<213> ORGANISM: Artificial Sequence
<220> FEATURE:
<223> OTHER INFORMATION: Primer 61-67-CPK021-G

<400> SEQUENCE: 32
actttggtaa gagaaaggaa gacgtttagc ttgcctcgtc cccgccgggt caccc    55

<210> SEQ ID NO 33
<211> LENGTH: 62
<212> TYPE: DNA
<213> ORGANISM: Artificial Sequence
<220> FEATURE:
<223> OTHER INFORMATION: Primer 61-67-CPK022-G

<400> SEQUENCE: 33
aatatcataa aaaagagaa tctttcccgg gtggatggcg gcgttagtat cgaatcgaca  60
gc                                                                62

<210> SEQ ID NO 34
<211> LENGTH: 62
<212> TYPE: DNA
<213> ORGANISM: Artificial Sequence
<220> FEATURE:
<223> OTHER INFORMATION: Primer 61-67-CPK023-G

<400> SEQUENCE: 34
gctgtcgatt cgatactaac gccgccatcc acccgggaaa gattctcttt ttttatgata  60
tt                                                                62

<210> SEQ ID NO 35
<211> LENGTH: 45
<212> TYPE: DNA
<213> ORGANISM: Artificial Sequence
<220> FEATURE:
<223> OTHER INFORMATION: Primer 61-67-CPK024-G

<400> SEQUENCE: 35
gtttaaacgt gttaacgttt ctttcgccta cgtggaagga gaatc                45

<210> SEQ ID NO 36
<211> LENGTH: 35
<212> TYPE: DNA
<213> ORGANISM: Artificial Sequence
<220> FEATURE:
```

```
<223> OTHER INFORMATION: Primer 61-67-CPK025-G

<400> SEQUENCE: 36 tcccccggg ttaaaaaaaa tccttggact agtca                          35

<210> SEQ ID NO 37
<211> LENGTH: 35
<212> TYPE: DNA
<213> ORGANISM: Artificial Sequence
<220> FEATURE:
<223> OTHER INFORMATION: Primer 61-67-CPK031-G

<400> SEQUENCE: 37 tcccccggg agttatgaca attacaacaa cagaa                          35

<210> SEQ ID NO 38
<211> LENGTH: 30
<212> TYPE: DNA
<213> ORGANISM: Artificial Sequence
<220> FEATURE:
<223> OTHER INFORMATION: Primer 61-67-CPK032-G

<400> SEQUENCE: 38 tcccccggg tatatatata tcattgttat                                30

<210> SEQ ID NO 39
<211> LENGTH: 30
<212> TYPE: DNA
<213> ORGANISM: Artificial Sequence
<220> FEATURE:
<223> OTHER INFORMATION: Primer 61-67-CPK035-G

<400> SEQUENCE: 39 tcccccggg aaaagtaagt caaaaggcac                                30

<210> SEQ ID NO 40
<211> LENGTH: 30
<212> TYPE: DNA
<213> ORGANISM: Artificial Sequence
<220> FEATURE:
<223> OTHER INFORMATION: Primer 61-67-CPK040-G

<400> SEQUENCE: 40 tcccccggg atggtctgct taaatttcat                                30

<210> SEQ ID NO 41
<211> LENGTH: 45
<212> TYPE: DNA
<213> ORGANISM: Artificial Sequence
<220> FEATURE:
<223> OTHER INFORMATION: Primer 61-67-CPK041-G

<400> SEQUENCE: 41 tcccccggg tagcttgtac ccattaaaag aattttatca tgccg               45

<210> SEQ ID NO 42
<211> LENGTH: 30
<212> TYPE: DNA
<213> ORGANISM: Artificial Sequence
<220> FEATURE:
<223> OTHER INFORMATION: Primer 61-67-CPK046-G

<400> SEQUENCE: 42 tcccccggg tttctcattc aagtggtaac                                30
```

<210> SEQ ID NO 43
<211> LENGTH: 30
<212> TYPE: DNA
<213> ORGANISM: Artificial Sequence
<220> FEATURE:
<223> OTHER INFORMATION: Primer 61-67-CPK047-G

<400> SEQUENCE: 43
tcccccgggg taaataaaga aaataaagtt                                    30

<210> SEQ ID NO 44
<211> LENGTH: 47
<212> TYPE: DNA
<213> ORGANISM: Artificial Sequence
<220> FEATURE:
<223> OTHER INFORMATION: Primer 61-67-CPK050-G

<400> SEQUENCE: 44
aatttttgaa aattcaatat aaatggcttc agaaaaagaa attagga                 47

<210> SEQ ID NO 45
<211> LENGTH: 47
<212> TYPE: DNA
<213> ORGANISM: Artificial Sequence
<220> FEATURE:
<223> OTHER INFORMATION: Primer 61-67-CPK051-G

<400> SEQUENCE: 45
tcctaatttc tttttctgaa gccatttata ttgaattttc aaaaatt                 47

<210> SEQ ID NO 46
<211> LENGTH: 51
<212> TYPE: DNA
<213> ORGANISM: Artificial Sequence
<220> FEATURE:
<223> OTHER INFORMATION: Primer 61-67-CPK052-G

<400> SEQUENCE: 46
agttttcacc aattggtctg cagccattat agttttttct ccttgacgtt a            51

<210> SEQ ID NO 47
<211> LENGTH: 51
<212> TYPE: DNA
<213> ORGANISM: Artificial Sequence
<220> FEATURE:
<223> OTHER INFORMATION: Primer 61-67-CPK053-G

<400> SEQUENCE: 47
taacgtcaag gagaaaaaac tataatggct gcagaccaat tggtgaaaac t            51

<210> SEQ ID NO 48
<211> LENGTH: 47
<212> TYPE: DNA
<213> ORGANISM: Artificial Sequence
<220> FEATURE:
<223> OTHER INFORMATION: Primer 61-67-CPK054-G

<400> SEQUENCE: 48
aatttttgaa aattcaatat aaatgaaact ctcaactaaa ctttgtt                 47

<210> SEQ ID NO 49
<211> LENGTH: 47
<212> TYPE: DNA
<213> ORGANISM: Artificial Sequence
<220> FEATURE:
<223> OTHER INFORMATION: Primer 61-67-CPK055-G

```
<400> SEQUENCE: 49
aacaaagttt agttgagagt ttcatttata ttgaattttc aaaaatt        47

<210> SEQ ID NO 50
<211> LENGTH: 47
<212> TYPE: DNA
<213> ORGANISM: Artificial Sequence
<220> FEATURE:
<223> OTHER INFORMATION: Primer 61-67-CPK056-G

<400> SEQUENCE: 50 aattttgaa aattcaatat aaatgtctca gaacgtttac attgtat         47

<210> SEQ ID NO 51
<211> LENGTH: 47
<212> TYPE: DNA
<213> ORGANISM: Artificial Sequence
<220> FEATURE:
<223> OTHER INFORMATION: Primer 61-67-CPK057-G

<400> SEQUENCE: 51
atacaatgta aacgttctga gacatttata ttgaattttc aaaaatt        47

<210> SEQ ID NO 52
<211> LENGTH: 51
<212> TYPE: DNA
<213> ORGANISM: Artificial Sequence
<220> FEATURE:
<223> OTHER INFORMATION: Primer 61-67-CPK058-G

<400> SEQUENCE: 52
tgcagaagtt aagaacggta atgacattat agttttttct ccttgacgtt a   51

<210> SEQ ID NO 53
<211> LENGTH: 51
<212> TYPE: DNA
<213> ORGANISM: Artificial Sequence
<220> FEATURE:
<223> OTHER INFORMATION: Primer 61-67-CPK059-G

<400> SEQUENCE: 53
taacgtcaag gagaaaaaac tataatgtca ttaccgttct taacttctgc a   51

<210> SEQ ID NO 54
<211> LENGTH: 47
<212> TYPE: DNA
<213> ORGANISM: Artificial Sequence
<220> FEATURE:
<223> OTHER INFORMATION: Primer 61-67-CPK060-G

<400> SEQUENCE: 54 aattttgaa aattcaatat aaatgtcaga gttgagagcc ttcagtg         47

<210> SEQ ID NO 55
<211> LENGTH: 47
<212> TYPE: DNA
<213> ORGANISM: Artificial Sequence
<220> FEATURE:
<223> OTHER INFORMATION: Primer 61-67-CPK061-G

<400> SEQUENCE: 55
cactgaaggc tctcaactct gacatttata ttgaattttc aaaaatt        47

<210> SEQ ID NO 56
<211> LENGTH: 51
```

```
<212> TYPE: DNA
<213> ORGANISM: Artificial Sequence
<220> FEATURE:
<223> OTHER INFORMATION: Primer 61-67-CPK062-G

<400> SEQUENCE: 56
ggtaacggat gctgtgtaaa cggtcattat agttttttct ccttgacgtt a         51

<210> SEQ ID NO 57
<211> LENGTH: 51
<212> TYPE: DNA
<213> ORGANISM: Artificial Sequenc
<220> FEATURE:
<223> OTHER INFORMATION: Primer 61-67-CPK063-G

<400> SEQUENCE: 57
taacgtcaag gagaaaaaac tataatgacc gtttacacag catccgttac c         51

<210> SEQ ID NO 58
<211> LENGTH: 47
<212> TYPE: DNA
<213> ORGANISM: Artificial Sequence
<220> FEATURE:
<223> OTHER INFORMATION: Primer 61-67-CPK064-G

<400> SEQUENCE: 58
aatttttgaa aattcaatat aaatgactgc cgacaacaat agtatgc              47

<210> SEQ ID NO 59
<211> LENGTH: 47
<212> TYPE: DNA
<213> ORGANISM: Artificial Sequence
<220> FEATURE:
<223> OTHER INFORMATION: Primer 61-67-CPK065-G

<400> SEQUENCE: 59
gcatactatt gttgtcggca gtcatttata ttgaattttc aaaaatt              47

<210> SEQ ID NO 60
<211> LENGTH: 70
<212> TYPE: DNA
<213> ORGANISM: Artificial Sequence
<220> FEATURE:
<223> OTHER INFORMATION: Primer 61-67-CPK066-G

<400> SEQUENCE: 60
ggtaagacgg ttgggtttta tcttttgcag ttggtactat taagaacaat cacaggaaac   60
agctatgacc                                                          70

<210> SEQ ID NO 61
<211> LENGTH: 70
<212> TYPE: DNA
<213> ORGANISM: Artificial Sequence
<220> FEATURE:
<223> OTHER INFORMATION: Primer 61-67-CPK067-G

<400> SEQUENCE: 61
ttgcgttttg tactttggtt cgctcaattt tgcaggtaga taatcgaaaa gttgtaaaac   60
gacggccagt                                                          70

<210> SEQ ID NO 62
<211> LENGTH: 44
<212> TYPE: DNA
<213> ORGANISM: Artificial Sequence
<220> FEATURE:
```

<223> OTHER INFORMATION: Primer 91-014-CPK231-G

<400> SEQUENCE: 62
ttgtgatgct aaagttatga gtctcgagaa gttaagatta tatg　　　　　　　　　44

<210> SEQ ID NO 63
<211> LENGTH: 44
<212> TYPE: DNA
<213> ORGANISM: Artificial Sequence
<220> FEATURE:
<223> OTHER INFORMATION: Primer 91-014-CPK232-G

<400> SEQUENCE: 63
catataatct aacttctcg agactcataa ctttagcatc acaa　　　　　　　　　44

<210> SEQ ID NO 64
<211> LENGTH: 28
<212> TYPE: DNA
<213> ORGANISM: Artificial Sequence
<220> FEATURE:
<223> OTHER INFORMATION: Primer 91-014-CPK233-G

<400> SEQUENCE: 64
gtttaaactt caaagctcga tgcctcat　　　　　　　　　　　　　　　　　28

<210> SEQ ID NO 65
<211> LENGTH: 28
<212> TYPE: DNA
<213> ORGANISM: Artificial Sequence
<220> FEATURE:
<223> OTHER INFORMATION: Primer 91-014-CPK236-G

<400> SEQUENCE: 65
gtttaaacga ggctcaccta acaattca　　　　　　　　　　　　　　　　　28

<210> SEQ ID NO 66
<211> LENGTH: 44
<212> TYPE: DNA
<213> ORGANISM: Artificial Sequence
<220> FEATURE:
<223> OTHER INFORMATION: Primer 91-014-CPK237-G

<400> SEQUENCE: 66
gatgtgtatt actagtgtcg acactgctga agaatttgat tttt　　　　　　　　　44

<210> SEQ ID NO 67
<211> LENGTH: 44
<212> TYPE: DNA
<213> ORGANISM: Artificial Sequence
<220> FEATURE:
<223> OTHER INFORMATION: Primer 91-014-CPK238-G

<400> SEQUENCE: 67
aaaaatcaaa ttcttcagca gtgtcgacac tagtaataca catc　　　　　　　　　44

<210> SEQ ID NO 68
<211> LENGTH: 1761
<212> TYPE: DNA
<213> ORGANISM: Artificial Sequence
<220> FEATURE:
<223> OTHER INFORMATION: DNA fragment GAL11 to 48-NatR- GAL11500 to 1550

<400> SEQUENCE: 68
atgactaaat ctcattcaga agaagtgatt gtacctgagt tcaattctca caggaaacag　　60 ctatgaccat gattacgcca agcttggtac cgagctcgga tccactagta acggccgcca　　120

```
gtgtgctgga attcgccctt gtcgacacta gtaatacaca tcatcgtcct acaagttcat    180
caaagtgttg gacagacaac tataccagca tggatctctt gtatcggttc ttttctcccg    240
ctctctcgca ataacaatga acactgggtc aatcatagcc tacacaggtg aacagagtag    300
cgtttataca gggtttatac ggtgattcct acggcaaaaa ttttcatttt ctaaaaaaaa    360
aaagaaaaat ttttctttcc aacgctagaa ggaaaagaaa aatctaatta aattgatttg    420
gtgattttct gagagttccc ttttcatat atcgaatttt gaatataaaa ggagatcgaa    480 aaaattttc tattcaatct gttttctggt tttatttgat agttttttg tgtattatta    540 ttatggatta gtactggttt atatgggttt ttctgtataa cttcttttta ttttagtttg    600
tttaatctta ttttgagtta cattatagtt ccctaactgc aagagaagta acattaaaaa    660
tgaccactct tgacgacacg gcttaccggt accgcaccag tgtcccgggg gacgccgagg    720
ccatcgaggc actggatggg tccttcacca ccgacaccgt cttccgcgtc accgccaccg    780
gggacggctt caccctgcgg gaggtgccgg tggacccgcc cctgaccaag gtgttccccg    840
acgacgaatc ggacgacgaa tcggacgccg gggaggacgg cgacccggac tcccggacgt    900
tcgtcgcgta cggggacgac ggcgacctgg cgggcttcgt ggtcgtctcg tactccggct    960
ggaaccgccg gctgaccgtc gaggacatcg aggtcgcccc ggagcaccgg ggcacggggg    1020
tcgggcgcgc gttgatgggg ctcgcgacgg agttcgcccg cgagcggggc gccgggcacc    1080
tctggctgga ggtcaccaac gtcaacgcac cggcgatcca cgcgtaccgg cggatggggt    1140
tcaccctctg cggcctggac accgcccgt acgacggcac cgcctcggac ggcgagcagg    1200
cgctctacat gagcatgccc tgcccctgag tttaacttga tactactaga ttttttctct    1260
tcatttataa aattttttggt tataattgaa gctttagaag tatgaaaaaa tccttttttt    1320
tcattctttg caaccaaaat aagaagcttc ttttattcat tgaaatgatg aatataaacc    1380
taacaaaaga aaaagactcg aatatcaaac attaaaaaaa aataaaagag gttatctgtt    1440
ttcccattta gttggagttt gcattttcta atagatagaa ctctcaatta atgtggattt    1500
agtttctctg ttcgttttt tttgttttgt tctcactgta tttacatttc tatttagtat    1560
ttagttattc atataatctt aacttctcga ggagctcaag gcaattctg cagatatcca    1620 tcacactggc ggccgctcga gcatgcatct agagggccca attcgcccta tagtgagtcg    1680
tattacaatt cactggccgt cgttttacaa caagtaccct aagatcactg atgctgagct    1740
agaaaatgct atcatcgtct c                                              1761
```

<210> SEQ ID NO 69
<211> LENGTH: 7348
<212> TYPE: DNA
<213> ORGANISM: Artificial Sequence
<220> FEATURE:
<223> OTHER INFORMATION: Vector pAM178

<400> SEQUENCE: 69

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatcga ctacgtcgta aggccgtttc tgacagagta aaattcttga gggaactttc    240
accattatgg gaaatgcttc aagaaggtat tgacttaaac tccatcaaat ggtcaggtca    300
ttgagtgttt tttatttgtt gtatttttttt tttttagag aaaatcctcc aatatcaaat    360
```

```
taggaatcgt agtttcatga ttttctgtta cacctaactt tttgtgtggt gccctcctcc    420
ttgtcaatat taatgttaaa gtgcaattct ttttccttat cacgttgagc cattagtatc    480
aatttgctta cctgtattcc tttactatcc tccttttcct ccttcttgat aaatgtatgt    540
agattgcgta tatagtttcg tctaccctat gaacatattc cattttgtaa tttcgtgtcg    600
tttctattat gaatttcatt tataaagttt atgtacaaat atcataaaaa aagagaatct    660
ttttaagcaa ggattttctt aacttcttcg gcgacagcat caccgacttc ggtggtactg    720
ttggaaccac ctaaatcacc agttctgata cctgcatcca aaaccttttt aactgcatct    780
tcaatggcct taccttcttc aggcaagttc aatgacaatt tcaacatcat tgcagcagac    840
aagatagtgg cgatagggtc aaccttattc tttggcaaat ctggagcaga accgtggcat    900
ggttcgtaca aaccaaatgc ggtgttcttg tctggcaaag aggccaagga cgcagatggc    960
aacaaaccca aggaacctgg gataacggag gcttcatcgg agatgatatc accaaacatg    1020
ttgctggtga ttataatacc atttaggtgg gttgggttct taactaggat catggcggca    1080
gaatcaatca attgatgttg aaccttcaat gtagggaatt cgttcttgat ggtttcctcc    1140
acagtttttc tccataatct tgaagaggcc aaaagattag ctttatccaa ggaccaaata    1200
ggcaatggtg gctcatgttg tagggccatg aaagcggcca ttcttgtgat tctttgcact    1260
tctggaacgg tgtattgttc actatcccaa gcgacaccat caccatcgtc ttcctttctc    1320
ttaccaaagt aaatacctcc cactaattct ctgacaacaa cgaagtcagt acctttagca    1380
aattgtggct tgattggaga taagtctaaa agagagtcgg atgcaaagtt acatggtctt    1440
aagttggcgt acaattgaag ttcttttacgg attttttagta aaccttgttc aggtctaaca    1500
ctaccggtac cccatttagg accagccaca gcacctaaca aaacggcatc aaccttcttg    1560
gaggcttcca gcgcctcatc tggaagtgga acacctgtag catcgatagc agcaccacca    1620
attaaatgat tttcgaaatc gaacttgaca ttggaacgaa catcagaaat agctttaaga    1680 acctaatgg cttcggctgt gatttcttga ccaacgtggt cacctggcaa aacgacgatc    1740
ttcttagggg cagacattac aatggtatat ccttgaaata tatataaaaa aaggcgcctt    1800
agaccgctcg gccaaacaac caattacttg ttgagaaata gagtataatt atcctataaa    1860
tataacgttt ttgaacacac atgaacaagg aagtacagga caattgattt tgaagagaat    1920
gtggattttg atgtaattgt tgggattcca ttttttaataa ggcaataata ttaggtatgt    1980
ggatatacta gaagttctcc tcgaccgtcg atatgcggtg tgaaataccg cacagatgcg    2040
taaggagaaa ataccgcatc aggaaattgt aaacgttaat attttgttaa aattcgcgtt    2100
aaatttttgt taaatcagct cattttttaa ccaataggcc gaaatcggca aaatccctta    2160
taaatcaaaa gaatagaccg agatagggtt gagtgttgtt ccagtttgga acaagagtcc    2220
actattaaag aacgtggact ccaacgtcaa agggcgaaaa accgtctatc agggcgatgg    2280
cccactacgt gaaccatcac cctaatcaag tttttggggg tcgaggtgcc gtaaagcact    2340
aaatcggaac cctaaaggga gcccccgatt tagagcttga cggggaaagc cggcgaacgt    2400
ggcgagaaag gaagggaaga agcgaaaagg agcgggcgct agggcgctgg caagtgtagc    2460
ggtcacgctg cgcgtaacca ccacacccgc cgcgcttaat gcgccgctac agggcgcgtc    2520
gcgccattcg ccattcaggc tgcgcaactg ttgggaaggg cgatcggtgc gggcctcttc    2580
gctattacgc cagctgaatt ggagcgacct catgctatac ctgagaaagc aacctgacct    2640
acaggaaaga gttactcaag aataagaatt ttcgttttaa aacctaagag tcactttaaa    2700
atttgtatac acttattttt tttataactt atttaataat aaaaatcata aatcataaga    2760
```

```
aattcgctta tttagaagtg tcaacaacgt atctaccaac gatttgaccc ttttccatct   2820
tttcgtaaat ttctggcaag gtagacaagc cgacaacctt gattggagac ttgaccaaac   2880
ctctggcgaa gaattgttaa ttaagagctc agatcttatc gtcgtcatcc ttgtaatcca   2940
tcgatactag tgcggccgcc ctttagtgag ggttgaattc gaattttcaa aaattcttac   3000
tttttttttg gatggacgca aagaagttta ataatcatat tacatggcat taccaccata   3060
tacatatcca tatacatatc catatctaat cttacttata tgttgtggaa atgtaaagag   3120
ccccattatc ttagcctaaa aaaaccttct ctttggaact ttcagtaata cgcttaactg   3180
ctcattgcta tattgaagta cggattagaa gccgccgagc gggtgacagc cctccgaagg   3240
aagactctcc tccgtgcgtc ctcgtcttca ccggtcgcgt tcctgaaacg cagatgtgcc   3300
tcgcgccgca ctgctccgaa caataaagat tctacaatac tagcttttat ggttatgaag   3360
aggaaaaatt ggcagtaacc tggccccaca aaccttcaaa tgaacgaatc aaattaacaa   3420
ccataggatg ataatgcgat tagttttttta gccttatttc tggggtaatt aatcagcgaa   3480
gcgatgattt ttgatctatt aacagatata taaatgcaaa aactgcataa ccactttaac   3540
taatactttc aacattttcg gtttgtatta cttcttattc aaatgtaata aaagtatcaa   3600
caaaaaattg ttaatatacc tctatacttt aacgtcaagg agaaaaaacc ccggatccgt   3660
aatacgactc actatagggc ccgggcgtcg acatggaaca gaagttgatt tccgaagaag   3720
acctcgagta agcttggtac cgcggctagc taagatccgc tctaaccgaa aaggaaggag   3780
ttagacaacc tgaagtctag gtccctattt atttttttat agttatgtta gtattaagaa   3840
cgttatttat atttcaaatt tttcttttttt ttctgtacag acgcgtgtac gcatgtaaca   3900
ttatactgaa aaccttgctt gagaaggttt tgggacgctc gaagatccag ctgcattaat   3960
gaatcggcca acgcgcgggg agaggcggtt tgcgtattgg gcgctcttcc gcttcctcgc   4020
tcactgactc gctgcgctcg gtcgttcggc tgcggcgagc ggtatcagct cactcaaagg   4080
cggtaatacg gttatccaca gaatcagggg ataacgcagg aaagaacatg tgagcaaaag   4140
gccagcaaaa ggccaggaac cgtaaaaagg ccgcgttgct ggcgtttttc cataggctcc   4200
gcccccctga cgagcatcac aaaaatcgac gctcaagtca gaggtggcga aacccgacag   4260
gactataaag ataccaggcg tttccccctg gaagctccct cgtgcgctct cctgttccga   4320
ccctgccgct taccggatac ctgtccgcct ttctcccttc gggaagcgtg gcgctttctc   4380
atagctcacg ctgtaggtat ctcagttcgg tgtaggtcgt tcgctccaag ctgggctgtg   4440
tgcacgaacc ccccgttcag cccgaccgct gcgccttatc cggtaactat cgtcttgagt   4500
ccaacccggt aagacacgac ttatcgccac tggcagcagc cactggtaac aggattagca   4560
gagcgaggta tgtaggcggt gctacagagt tcttgaagtg gtggcctaac tacggctaca   4620
ctagaaggac agtatttggt atctgcgctc tgctgaagcc agttaccttc ggaaaaagag   4680
ttggtagctc ttgatccggc aaacaaacca ccgctggtag cggtggtttt tttgtttgca   4740
agcagcagat tacgcgcaga aaaaaggat ctcaagaaga tcctttgatc ttttctacgg   4800
ggtctgacgc tcagtggaac gaaaactcac gttaagggat tttggtcatg agattatcaa   4860
aaaggatctt cacctagatc cttttaaatt aaaaatgaag ttttaaatca atctaaagta   4920
tatatgagta aacttggtct gacagttacc aatgcttaat cagtgaggca cctatctcag   4980
cgatctgtct atttcgttca tccatagttg cctgactccc cgtcgtgtag ataactacga   5040
tacgggaggg cttaccatct ggccccagtg ctgcaatgat accgcgagac ccacgctcac   5100
```

```
cggctccaga tttatcagca ataaaccagc cagccggaag ggccgagcgc agaagtggtc    5160
ctgcaacttt atccgcctcc atccagtcta ttaattgttg ccgggaagct agagtaagta    5220
gttcgccagt taatagtttg cgcaacgttg ttgccattgc tacaggcatc gtggtgtcac    5280
gctcgtcgtt tggtatggct tcattcagct ccggttccca acgatcaagg cgagttacat    5340 gatccccat  gttgtgcaaa aaagcggtta gctccttcgg tcctccgatc gttgtcagaa    5400
gtaagttggc cgcagtgtta tcactcatgg ttatggcagc actgcataat tctcttactg    5460
tcatgccatc cgtaagatgc ttttctgtga ctggtgagta ctcaaccaag tcattctgag    5520
aatagtgtat gcggcgaccg agttgctctt gcccggcgtc aatacgggat aataccgcgc    5580
cacatagcag aactttaaaa gtgctcatca ttggaaaacg ttcttcgggg cgaaaactct    5640
caaggatctt accgctgttg agatccagtt cgatgtaacc cactcgtgca cccaactgat    5700
cttcagcatc ttttactttc accagcgttt ctgggtgagc aaaaacagga aggcaaaatg    5760
ccgcaaaaaa gggaataagg gcgacacgga aatgttgaat actcatactc ttccttttc    5820 aatattattg aagcatttat cagggttatt gtctcatgag cggatacata tttgaatgta    5880
tttagaaaaa taaacaaata ggggttccgc gcacatttcc ccgaaaagtg ccacctgaac    5940
gaagcatctg tgcttcattt tgtagaacaa aaatgcaacg cgagagcgct aattttcaa    6000 acaaagaatc tgagctgcat ttttacagaa cagaaatgca acgcgaaagc gctatttac    6060 caacgaagaa tctgtgcttc attttgtaa  acaaaaatg caacgcgaga gcgctaattt    6120
ttcaaacaaa gaatctgagc tgcattttta cagaacagaa atgcaacgcg agagcgctat    6180
tttaccaaca aagaatctat acttcttttt tgttctacaa aaatgcatcc cgagagcgct    6240 attttctaa  caaagcatct tagattactt ttttctcct tgtgcgctc tataatgcag    6300 tctcttgata acttttgca ctgtaggtcc gttaaggtta aagaaggct actttggtgt    6360 ctattttctc ttccataaaa aaagcctgac tccacttccc gcgtttactg attactagcg    6420
aagctgcggg tgcatttttt caagataaag gcatccccga ttatattcta taccgatgtg    6480
gattgcgcat actttgtgaa cagaaagtga tagcgttgat gattcttcat tggtcagaaa    6540
attatgaacg gtttcttcta ttttgtctct atatactacg tataggaaat gtttacattt    6600
tcgtattgtt ttcgattcac tctatgaata gttcttacta caattttttt gtctaaagag    6660
taatactaga gataaacata aaaaatgtag aggtcgagtt tagatgcaag ttcaaggagc    6720
gaaaggtgga tgggtaggtt atatagggat atagcacaga gatatatagc aaagagatac    6780
ttttgagcaa tgtttgtgga agcggtattc gcaatatttt agtagctcgt tacagtccgg    6840 tgcgttttg gttttttgaa agtgcgtctt cagagcgctt ttggttttca aaagcgctct    6900
gaagttccta tactttctag agaataggaa cttcggaata ggaacttcaa agcgtttccg    6960
aaaacgagcg cttccgaaaa tgcaacgcga gctgcgcaca tacagctcac tgttcacgtc    7020
gcacctatat ctgcgtgttg cctgtatata tatacatg agaagaacgg catagtgcgt    7080
gtttatgctt aaatgcgtac ttatatgcgt ctatttatgt aggatgaaag gtagtctagt    7140
acctcctgtg atattatccc attccatgcg gggtatcgta tgcttccttc agcactaccc    7200
tttagctgtt ctatatgctg ccactcctca attggattag tctcatcctt caatgctatc    7260
atttcctttg atattggatc atactaagaa accattatta tcatgacatt aacctataaa    7320
aataggcgta tcacgaggcc ctttcgtc                                      7348
```

<210> SEQ ID NO 70
<211> LENGTH: 4883
<212> TYPE: DNA
<213> ORGANISM: Artificial Sequence
<220> FEATURE:
<223> OTHER INFORMATION: T7-FS-FRT-Kan-FRT cassette

<400> SEQUENCE: 70

```
gctgggcgat ctgttgcgcg aagtggtatg gccgacagat gtgtccacgc tggatgttga      60
tgcaatggtg gtacgcgaaa ccactcaccg tttcagccgc ttatcctttc accgggcaat     120
ggtcgggcga cgtttgccgc ttctgaaaac cgcctcgggc ctgacctggc tggccttttg     180
cccggaacaa gaccgcaagg aattaatcga aatgttagcc tcccgccccg gtgatgacta     240
tcaactggca cgggaaccgt taaagctgga agccattctg gcgcgcgcgc gcaaagaggg     300
ttacggacag aactaccgcg gctgggatca ggaggagaag atcgcctcta tcgccgtacc     360
gctgcgcagt gaacaacggg tgattggctg tctgaatctg gtgtatatgg cgagcgcaat     420
gaccattgaa caggcagcgg aaaagcatct tccggcgcta caacgggtag caaaacagat     480
cgaagaaggg gttgaatcgc aggctattct ggtggccgga aggcgaagcg gcatgcaagg     540
agatggcgcc caacagtccc ccggccacgg ggcctgccac catacccacg ccgaaacaag     600
cgctcatgag cccgaagtgg cgagcccgat cttccccatc ggtgatgtcg gcgatatagg     660
cgccagcaac cgcacctgtg gcgccggtga tgccggccac gatgcgtccg gcgtagagga     720
tcgagatctc gatcccgcga aattaatacg actcactata ggggaattgt gagcggataa     780
caattcccct ctagaaataa ttttgtttaa ctttaagaag gagatatacc atggacactc     840
tgccgatctc ttccgtaagc ttttcttcct ctacttcccc gctggtagtc gatgacaagg     900
tttctaccaa acctgatgta attcgtcaca ctatgaactt caacgcatct atctggggcg     960
atcagttcct gacttatgat gaaccggaag atctggtaat gaaaaagcaa ctggtagaag    1020
aactgaaaga agaagttaaa aaggaactga tcaccattaa gggtagcaac gaaccgatgc    1080
agcacgtgaa actgattgaa ctgatcgatg cggttcagcg tctgggtatt gcttatcatt    1140
ttgaagagga aatcgaggaa gctctgcaac acatccacgt aacctacggc gaacaatggg    1200
tggataaaga gaatctgcag tctatcagcc tgtggttccg cctgctgcgt cagcaaggtt    1260
tcaatgtctc ttctggcgtt ttcaaagact tcatggatga aaagggcaaa ttcaaggaat    1320
ccctgtgtaa cgatgcgcaa ggtatcctgg cactgtacga agcggccttc atgcgtgtgg    1380
aagacgaaac cattctggac aacgcgctgg aattcactaa agtgcatctg gacatcatcg    1440
cgaaagatcc gtcctgcgac tcctctctgc gtactcagat ccatcaagcg ctgaaacagc    1500
cgctgcgtcg tcgcctggca cgtattgagg ctctgcacta tatgccgatt taccagcagg    1560
aaacctctca cgacgaagtc ctgctgaaac tggctaaact ggacttcagc gttctgcaat    1620
ctatgcacaa gaaagaactg tcccacatct gcaaatggtg gaaagatctg gatctgcaaa    1680
acaaactgcc gtacgttcgt gaccgtgttg ttgagggcta ttttttggatt ctgtccatct    1740
actatgaacc acagcacgcg cgtactcgca tgtttctgat gaaaacctgc atgtggctgg    1800
ttgtcctgga cgacacctttt gacaactatg gtacgtacga agaactggaa atcttcaccc    1860
aggccgtgga acgttggtct atttcctgcc tggatatgct gccggaatac atgaaactga    1920
tctatcaaga actggttaac ctgcacgtgg aaatggaaga gtctctggag aaagaaggta    1980
aaacttacca gatccactac gtcaaggaga tggcgaaaga actggtccgt aactatctgg    2040
```

```
tcgaggcgcg ttggctgaaa gagggctata tgccgactct ggaagaatac atgagcgtat    2100
ccatggttac cggcacctac ggcctgatga ttgcgcgttc ctacgtcggc cgtggtgata    2160
ttgttaccga agatacctttt aagtgggttt cttcctaccc gccgatcatc aaagcgtctt   2220
gtgtcatcgt tcgcctgatg gacgacatcg tttctcacaa agaggagcaa gaacgtggtc    2280
acgtagcatc tagcatcgaa tgctactcca aagaatccgg cgcgtccgaa gaagaagctt    2340
gcgaatacat cagccgtaaa gttgaagatg cctggaaagt tatcaaccgc gaaagcctgc    2400
gtccgacggc ggtcccgttt ccgctgctga tgccggcaat caacctggca cgcatgtgtg    2460
aggttctgta cagcgtgaac gatggtttta ctcacgcgga aggtgacatg aagagctata    2520
tgaagagctt cttcgtacac cctatggtcg tatgagagct cggtacccaa actctatgac    2580
tgagttaatt aagcagttca tacaggcgcg ccgtctgata aaacagaatt tgcctggcgg    2640
cagtagcgcg gtggtcccac ctgaccccat gccgaactca gaagtgaaac gccgtagcgc    2700
cgatggtagt gtggggtctc cccatgcgag agtaggaac tgccaggcat caaataaaac     2760
gaaaggctca gtcgaaagac tgggcctttc gttttatctg ttgttgtcg gtgaacgctc     2820 tcctgagtag gacaaatccg ccgggagcgg atttgaacgt tgcgaagcaa cggcccggag    2880
ggtggcgggc aggacgcccg ccataaactg ccaggcatca aattaagcag aaggccatcc    2940
tgacggatgg ccttttttgcg tttctacaaa ctctttctag agctgcctcg cgcgtttcgg   3000
tgatgacggt cctctgaccg gttggacgtt aaaaaatatc cccggcaact gacacgctac    3060
cggggatttt tttatcattc tgagcttgtc tgtaagcgga tgccgggagc agacaagccc    3120
gtgaagttcc tattctctag aaagtatagg aacttcagag cgctttgacg tcggaattgc    3180
cagctggggc gccctctggt aaggttggga agccctgcaa agtaaactgg atggctttct    3240
tgccgccaag gatctgatgg cgcagggat caagatctga tcaagagaca ggatgaggat     3300
cgtttcgcat gattgaacaa gatggattgc acgcaggttc tccggccgct tgggtggaga    3360
ggctattcgg ctatgactgg gcacaacaga caatcggctg ctctgatgcc gccgtgttcc    3420
ggctgtcagc gcaggggcgc ccggttcttt ttgtcaagac cgacctgtcc ggtgccctga    3480
atgaactgca ggacgaggca gcgcggctat cgtggctggc cacgacgggc gttccttgcg    3540
cagctgtgct cgacgttgtc actgaagcgg gaagggactg gctgctattg ggcgaagtgc    3600
cggggcagga tctcctgtca tctcaccttg ctcctgccga aaagtatcc atcatggctg     3660 atgcaatgcg gcggctgcat acgcttgatc cggctacctg cccattcgac caccaagcga    3720
aacatcgcat cgagcgagca cgtactcgga tggaagccgg tcttgtcgat caggatgatc    3780
tggacgaaga gcatcagggg ctcgcgccag ccgaactgtt cgccaggctc aaggcgcgca    3840
tgcccgacgg cgaggatctc gtcgtgaccc atggcgatgc ctgcttgccg aatatcatgg    3900
tggaaaatgg ccgcttttct ggattcatcg actgtggccg gctgggtgtg gcggaccgct    3960
atcaggacat agcgttggct acccgtgata ttgctgaaga cttggcggc gaatgggctg     4020 accgcttcct cgtgctttac ggtatcgccg ctcccgattc gcagcgcatc gccttctatc    4080
gccttcttga cgagttcttc tgagcgggac tctggggttc gagagctcgc ttggactcct    4140
gttgatagat ccagtaatga cctcagaact ccatctggat ttgttcagaa cgctcggttg    4200
ccgccgggcg ttttttattg gtgagaatcc aagcactagt aagggatc ttgaagttcc      4260 tattccgaag ttcctattct ctagaaagta taggaacttc acatgcagct cccggagacg    4320
gtcacgcgat cgcattataa aaattgcctg atacgctgcg cttatcaggc ctacaagttc    4380
agcgatctac attagccgca tccggcatga acaaagcgca ggaacaagcg tcgcatcatg    4440
```

| | |
|---|---|
| cctctttgac ccacagctgc ggaaaacgta ctggtgcaaa acgcagggtt atgatcatca | 4500 |
| gcccaacgac gcacagcgca tgaaatgccc agtccatcag gtaattgccg ctgatactac | 4560 |
| gcagcacgcc agaaaaccac ggggcaagcc cggcgatgat aaaaccgatt ccctgcataa | 4620 |
| acgccaccag cttgccagca atagccggtt gcacagagtg atcgagcgcc agcagcaaac | 4680 |
| agagcggaaa cgcgccgccc agacctaacc cacacaccat cgcccacaat accggcaatt | 4740 |
| gcatcggcag ccagataaag ccgcagaacc ccaccagttg taacaccagc gccagcatta | 4800 |
| acagtttgcg ccgatcctga tggcgagcca tagcaggcat cagcaaagct cctgcggctt | 4860 |
| gcccaagcgt catcaatgcc agt | 4883 |

<210> SEQ ID NO 71
<211> LENGTH: 1332
<212> TYPE: DNA
<213> ORGANISM: Artificial Sequence
<220> FEATURE:
<223> OTHER INFORMATION: Mevalonate kinase codon-optimized for expression in Escherichia coli

<400> SEQUENCE: 71

| | |
|---|---|
| atgtctctgc cattcctgac gtctgcgcca ggtaaggtga tcatcttcgg cgagcactct | 60 |
| gcggtgtaca ataagccggc cgtcgccgcc tctgtgtctg cgttacgcac ctacctgctg | 120 |
| atcagcgaat cttctgcacc ggacacgatc gagctggact ttccggacat cagcttcaac | 180 |
| cacaagtgga gcatcaacga cttcaacgcg atcacggagg accaggtgaa cagccaaaag | 240 |
| ctggccaaag cccagcaagc aaccgacggt ctgtctcagg agctggtgtc tctgctggac | 300 |
| ccgctgttag cgcagttaag cgagagcttc cattaccacg ccgcgttctg cttcctgtac | 360 |
| atgttcgttt gcctgtgccc gcacgcaaag aacatcaagt tcagcctgaa gagcacgctg | 420 |
| ccgattggcg caggcttagg ctctagcgca tctatcagcg tgagcctggc gctggcgatg | 480 |
| gcctatctgg gtggcctgat tggcagcaac gacctggaga aactgagcga aaacgacaag | 540 |
| cacatcgtga accagtgggc ctttatcggc gagaagtgca ttcatggcac cccgagcggc | 600 |
| attgacaacg cagttgccac gtatggcaac gccctgctgt cgagaaaga cagccacaac | 660 |
| ggcacgatca acacgaacaa cttcaagttc ctggacgact tcccggcgat cccgatgatt | 720 |
| ctgacctaca cccgtatccc acgcagcacc aaggatttag tcgcccgcgt gcgtgttta | 780 |
| gtcaccgaaa agttcccgga ggtgatgaag ccgatcctgg acgcgatggg cgagtgcgcg | 840 |
| ctgcagggtc tggagatcat gaccaagctg agcaagtgca agggcaccga cgatgaggcg | 900 |
| gtggagacca acaatgagct gtacgagcag ctgctggagc tgatccgtat caatcacggc | 960 |
| ctgctggtct ctatcggtgt gtctcacccg ggcctggaac tgatcaaaaa cctgagcgac | 1020 |
| gacctgcgca ttggctctac gaaattaacg ggtgcaggtg gcgtggctg ctctttaacg | 1080 |
| ctgctgcgcc gtgacattac gcaggagcaa atcgacagct tcaagaagaa gctgcaggac | 1140 |
| gacttcagct acgagacgtt cgagacggac ctgggcggca cgggctgttg cctgctgagc | 1200 |
| gccaaaaatc tgaacaagga cctgaagatc aaaagcctgg tgttccagct gttcgaaaac | 1260 |
| aagacgacca cgaagcagca gatcgacgac ctgttactgc cgggtaacac caatctgccg | 1320 |
| tggacgtctt aa | 1332 |

<210> SEQ ID NO 72
<211> LENGTH: 5220
<212> TYPE: DNA
<213> ORGANISM: Artificial Sequence
<220> FEATURE:
<223> OTHER INFORMATION: Plasmid pAM618

<400> SEQUENCE: 72

| | | | | | |
|---|---|---|---|---|---|
| gcacttttcg | gggaaatgtg | cgcggaaccc | ctatttgttt | attttttctaa | atacattcaa | 60 |
| atatgtatcc | gctcatgaga | caataaccct | gataaatgct | tcaataatat | tgaaaaagga | 120 |
| agagtatgag | tattcaacat | ttccgtgtcg | cccttattcc | cttttttgcg | gcattttgcc | 180 |
| ttcctgtttt | tgctcaccca | gaaacgctgg | tgaaagtaaa | agatgctgaa | gatcagttgg | 240 |
| gtgcacgagt | gggttacatc | gaactggatc | tcaacagcgg | taagatcctt | gagagttttc | 300 |
| gccccgaaga | acgttttcca | atgatgagca | cttttaaagt | tctgctatgt | ggcgcggtat | 360 |
| tatcccgtat | tgacgccggg | caagagcaac | tcggtcgccg | catacactat | tctcagaatg | 420 |
| acttggttga | gtactcacca | gtcacagaaa | agcatcttac | ggatggcatg | acagtaagag | 480 |
| aattatgcag | tgctgccata | accatgagtg | ataacactgc | ggccaactta | cttctgacaa | 540 |
| cgatcggagg | accgaaggag | ctaaccgctt | ttttgcacaa | catgggggat | catgtaactc | 600 |
| gccttgatcg | ttgggaaccg | gagctgaatg | aagccatacc | aaacgacgag | cgtgacacca | 660 |
| cgatgcctgt | agcaatggca | acaacgttgc | gcaaactatt | aactggcgaa | ctacttactc | 720 |
| tagcttcccg | gcaacaatta | atagactgga | tggaggcgga | taaagttgca | ggaccacttc | 780 |
| tgcgctcggc | ccttccggct | ggctggttta | ttgctgataa | atctggagcc | ggtgagcgtg | 840 |
| ggtcccgcgg | tatcattgca | gcactggggc | cagatggtaa | gccctcccgt | atcgtagtta | 900 |
| tctacacgac | ggggagtcag | gcaactatgg | atgaacgaaa | tagacagatc | gctgagatag | 960 |
| gtgcctcact | gattaagcat | tggtaactgt | cagaccaagt | ttactcatat | atactttaga | 1020 |
| ttgatttaaa | acttcatttt | taatttaaaa | ggatctaggt | gaagatcctt | tttgataatc | 1080 |
| tcatgaccaa | aatcccttaa | cgtgagtttt | cgttccactg | agcgtcagac | cccgtagaaa | 1140 |
| agatcaaagg | atcttcttga | gatcctttt | ttctgcgcgt | aatctgctgc | ttgcaaacaa | 1200 |
| aaaaaccacc | gctaccagcg | gtggtttgtt | tgccggatca | agagctacca | actcttttc | 1260 |
| cgaaggtaac | tggcttcagc | agagcgcaga | taccaaatac | tgtccttcta | gtgtagccgt | 1320 |
| agttaggcca | ccacttcaag | aactctgtag | caccgcctac | atacctcgct | ctgctaatcc | 1380 |
| tgttaccagt | ggctgctgcc | agtggcgata | agtcgtgtct | taccgggttg | gactcaagac | 1440 |
| gatagttacc | ggataaggcg | cagcggtcgg | gctgaacggg | gggttcgtgc | acacagccca | 1500 |
| gcttggagcg | aacgacctac | accgaactga | gatacctaca | gcgtgagcta | tgagaaagcg | 1560 |
| ccacgcttcc | cgaagggaga | aaggcggaca | ggtatccggt | aagcggcagg | gtcggaacag | 1620 |
| gagagcgcac | gagggagctt | ccagggggaa | acgcctggta | tctttatagt | cctgtcgggt | 1680 |
| ttcgccacct | ctgacttgag | cgtcgatttt | tgtgatgctc | gtcaggggg | cggagcctat | 1740 |
| ggaaaaacgc | cagcaacgcg | gcctttttac | ggttcctggc | cttttgctgg | ccttttgctc | 1800 |
| acatgttctt | tcctgcgtta | tcccctgatt | ctgtggataa | ccgtattacc | gcctttgagt | 1860 |
| gagctgatac | cgctcgccgc | agccgaacga | ccgagcgcag | cgagtcagtg | agcgaggaag | 1920 |
| cggaagagcg | cccaatacgc | aaaccgcctc | tccccgcgcg | ttggccgatt | cattaatgca | 1980 |
| gctggcacga | caggtttccc | gactggaaag | cgggcagtga | gcgcaacgca | attaatgtga | 2040 |

```
gttagctcac tcattaggca ccccaggctt tacactttat gcttccggct cgtatgttgt   2100
gtggaattgt gagcggataa caatttcaca caggaaacag ctatgaccat gattacgcca   2160
agctcgaaat taaccctcac taaagggaac aaaagctgga gctgcggccg cgagctttcc   2220
taaaaaaggt tatccaccct ttttaggatg caagagctat ggaaggtctc tataggcgcc   2280
agcaaccgca cctgtggcgc cggtgatgcc ggccacgatg cgtccggcgt agaggatcga   2340
gatctcgatc ccgcgaaatt aatacgactc actatagggg aattgtgagc ggataacaat   2400
tcccctctag aaataatttt gtttaacttt aagaaggaga tatacccata tggaattcga   2460
gctcggtacc cggggatcct ctagagtcga cctgcaggca tgcaagcttg agctcggtac   2520
ccaaactcta tgactgagtt aattaagcag ttcatacagg cgcgccgtct gataaaacag   2580
aatttgcctg gcggcagtag cgcggtggtc ccacctgacc ccatgccgaa ctcagaagtg   2640
aaacgccgta gcgccgatgg tagtgtgggg tctccccatg cgagagtagg gaactgccag   2700
gcatcaaata aaacgaaagg ctcagtcgaa agactgggcc tttcgtttta tctgttgttt   2760
gtcggtgaac gctctcctga gtaggacaaa tccgccggga gcggatttga acgttgcgaa   2820
gcaacggccc ggagggtggc gggcaggacg cccgccataa actgccaggc atcaaattaa   2880
gcagaaggcc atcctgacgg atggcctttt tgcgtttcta caaactcttt ctagagctgc   2940
ctcgcgcgtt tcggtgatga cggtcctctg accggttgga cgttaaaaaa tatccccggc   3000
aactgacacg ctaccgggga ttttttttatc attctgagct tgtctgtaag cggatgccgg   3060
gagcagacaa gcccgtgaag ttcctattct ctagaaagta taggaacttc agagcgcttt   3120
gacgtcggaa ttgccagctg gggcgccctc tggtaaggtt gggaagccct gcaaagtaaa   3180
ctggatggct tcttgccgc caaggatctg atggcgcagg ggatcaagat ctgatcaaga   3240
gacaggatga ggatcgtttc gcatgattga acaagatgga ttgcacgcag gttctccggc   3300
cgcttgggtg gagaggctat tcggctatga ctgggcacaa cagacaatcg gctgctctga   3360
tgccgccgtg ttccggctgt cagcgcaggg gcgcccggtt cttttgtca agaccgacct   3420 gtccggtgcc ctgaatgaac tgcaggacga ggcagcgcgg ctatcgtggc tggccacgac   3480
gggcgttcct tgcgcagctg tgctcgacgt tgtcactgaa gcgggaaggg actggctgct   3540
attgggcgaa gtgccggggc aggatctcct gtcatctcac cttgctcctg ccgagaaagt   3600
atccatcatg gctgatgcaa tgcggcggct gcatacgctt gatccggcta cctgcccatt   3660
cgaccaccaa gcgaaacatc gcatcgagcg agcacgtact cggatggaag ccggtcttgt   3720
cgatcaggat gatctggacg aagagcatca ggggctcgcg ccagccgaac tgttcgccag   3780
gctcaaggcg cgcatgcccg acggcgagga tctcgtcgtg acccatggcg atgcctgctt   3840
gccgaatatc atggtggaaa atggccgctt tctggattc atcgactgtg ccggctggg   3900 tgtggcggac cgctatcagg acatagcgtt ggctacccgt gatattgctg aagagcttgg   3960
cggcgaatgg gctgaccgct tcctcgtgct ttacggtatc gccgctcccg attcgcagcg   4020
catcgccttc tatcgccttc ttgacgagtt cttctgagcg ggactctggg gttcgagagc   4080
tcgcttggac tcctgttgat agatccagta atgacctcag aactccatct ggatttgttc   4140
agaacgctcg gttgccgccg ggcgtttttt attggtgaga atccaagcac tagttaaggg   4200
gatcttgaag ttcctattcc gaagttccta ttctctagaa agtataggaa cttcacatgc   4260
agctcccgga gacggtcacg cgatcgcttc ttgaagacga aagggcctcg tgatacgcct   4320 attttttatag gttaatgtca tgataataat ggtttcttag acgtcaggtg cactttttcg   4380
gggaaatgtg cgcggaaccc ctatttgttt attttttctaa atacattcaa atatgtatcc   4440
```

```
gctcatgaga caataaccct gataaatgct tcaataatat tgaaaaagga agagtgagac    4500
gccacgtacc agcggccgcg tcgacaagct tatgcatcca tgcagttggc catgcctaca    4560
tcgagtacca attcgcccta tagtgagtcg tattacaatt cactggccgt cgttttacaa    4620
cgtcgtgact gggaaaaccc tggcgttacc caacttaatc gccttgcagc acatcccct     4680 ttcgccagct ggcgtaatag cgaagaggcc cgcaccgatc gcccttccca acagttgcgc    4740
agcctgaatg gcgaatggga cgcgccctgt agcggcgcat taagcgcggc gggtgtggtg    4800
gttacgcgca gcgtgaccgc tacacttgcc agcgccctag cgcccgctcc tttcgctttc    4860
ttcccttcct ttctcgccac gttcgccggc tttccccgtc aagctctaaa tcggggctc     4920 cctttagggt tccgatttag tgctttacgg cacctcgacc ccaaaaaact tgattagggt    4980
gatggttcac gtagtgggcc atcgccctga tagacggttt ttcgcccttt gacgttggag    5040
tccacgttct ttaatagtgg actcttgttc caaactggaa caacactcaa ccctatctcg    5100
gtctattctt ttgatttata agggattttg ccgatttcgg cctattggtt aaaaaatgag    5160
ctgatttaac aaaaatttaa cgcgaatttt aacaaaatat taacgcttac aatttaggtg    5220
```

<210> SEQ ID NO 73
<211> LENGTH: 1356
<212> TYPE: DNA
<213> ORGANISM: Artificial Sequence
<220> FEATURE:
<223> OTHER INFORMATION: Phosphomevalonate kinase codon-optimized for
      expression in Escherichia coli

<400> SEQUENCE: 73

```
atgagcgaat tacgtgcatt cagcgcgcca ggtaaggcac tgctggccgg tggctacctg      60
gtgttagaca ccaagtacga ggcgttcgtc gtcggcttat ctgcccgtat gcatgcagtt     120
gcccacccgt atggtagcct gcagggctct gacaagttcg aagtgcgtgt gaagagcaag     180
cagttcaagg acggcgagtg gctgtaccac attagcccaa agagcggctt catcccggtt     240
agcattggtg gcagcaagaa cccatttatc gagaaggtca ttgccaacgt cttcagctac     300
ttcaagccga atatggacga ttactgcaac cgcaacctgt tcgtcatcga catttttcagc    360 gacgacgcgt accacagcca agaggactct gttacggagc atcgtggtaa ccgccgcctg     420
agcttccaca gccatcgcat tgaggaggtg ccgaagacgg tctgggttc tagcgccggt      480 ttagttaccg tcttaacgac ggcgttagcg agcttcttcg tgagcgacct ggagaacaac     540
gtggacaagt accgcgaagt gattcataac ctggcgcagg tggcacattg tcaggcccaa     600
ggtaagattg gctctggttt tgatgtggca gcggccgcct atggctctat ccgctatcgc     660
cgctttccgc cggccctgat cagcaatctg ccggacatcg gctctgcgac gtatggtagc     720
aaactggcgc atctggtgga cgaggaggac tggaacatca ccattaagtc taatcacctg     780
ccgagcggct taacgttatg gatgggcgat atcaagaacg gcagcgaaac ggttaagctg     840
gtgcagaaag tgaaaaactg gtacgacagc cacatgccgg aaagcctgaa gatttacacg     900
gagctggacc acgccaatag ccgtttcatg gatggtctga gcaagctgga ccgcctgcac     960
gaaacccacg acgactacag cgaccagatc ttcgagagcc tggagcgcaa tgactgcacc    1020
tgccagaagt acccggagat cacggaggtc cgcgatgccg tggcaacgat tcgccgtagc    1080
ttccgcaaaa ttacgaagga gagcggcgcg gatatcgaac caccggtcca gacgtctctg    1140
ctggacgact gtcaaacctt aaagggcgtg ttaacgtgcc tgattccggg cgcgggtggt    1200
tacgacgcca ttgccgtcat cacgaaacag gacgtcgatc tgcgcgcaca aacggccaac    1260
```

```
gacaaacgtt tcagcaaagt ccaatggctg gatgttacgc aggccgactg gggtgttcgc    1320
aaggagaagg acccggaaac gtatctggat aagtga                              1356
```

US 11,725,225 B2

PRODUCTION OF ISOPRENOIDS

PRIOR RELATED APPLICATIONS

This application claims the benefit under 35 U.S.C. § 119(e) of U.S. Provisional Application Nos. 60/994,790, filed Sep. 20, 2007, and 61/049,350, filed Apr. 30, 2008, all of which are incorporated herein by reference in their entirety.

FIELD OF THE INVENTION

Provided herein are, among others, compositions and methods for a robust production of isoprenoids. Also provided herein are nucleic acids, enzymes, expression vectors, and genetically modified host cells for carrying out the methods. Also provided herein are fermentation methods for high productivity of isoprenoids from genetically modified host cells.

BACKGROUND OF THE INVENTION

Isoprenoids are ubiquitous in nature. They comprise a diverse family of over 40,000 individual products, many of which are vital to living organisms. Isoprenoids serve to maintain cellular fluidity, electron transport, and other metabolic functions. A vast number of natural and synthetic isoprenoids are useful as pharmaceuticals, cosmetics, perfumes, pigments and colorants, fungicides, antiseptics, nutraceuticals, and fine chemical intermediates.

An isoprenoid product is typically composed of repeating five carbon isopentenyl diphosphate (IPP) units, although irregular isoprenoids and polyterpenes have been reported. In nature, isoprenoids are synthesized by consecutive condensations of their precursor IPP and its isomer dimethylallyl pyrophosphate (DMAPP). Two pathways for these precursors are known. Eukaryotes, with the exception of plants, generally use the mevalonate-dependent (MEV) pathway to convert acetyl coenzyme A (acetyl-CoA) to IPP, which is subsequently isomerized to DMAPP. Prokaryotes, with some exceptions, typically employ only the mevalonate-independent or deoxyxylulose-5-phosphate (DXP) pathway to produce IPP and DMAPP. Plants use both the MEV pathway and the DXP pathway. See Rohmer et al. (1993) *Biochem. J.* 295:517-524; Lange et al. (2000) *Proc. Natl. Acad. Sci. USA* 97(24): 13172-13177; Rohdich et al. (2002) *Proc. Natl. Acad. Sci. USA* 99:1158-1163.

Traditionally, isoprenoids have been manufactured by extraction from natural sources such as plants, microbes, and animals. However, the yield by way of extraction is usually very low due to a number of profound limitations. First, most isoprenoids accumulate in nature in only small amounts. Second, the source organisms in general are not amenable to the large-scale cultivation that is necessary to produce commercially viable quantities of a desired isoprenoid. Third, the requirement of certain toxic solvents for isoprenoid extraction necessitates special handling and disposal procedures, and thus complicating the commercial production of isoprenoids.

The elucidation of the MEV and DXP metabolic pathways has made biosynthetic production of isoprenoids feasible. For instance, microbes have been engineered to overexpress a part of or the entire mevalonate pathway for production of an isoprenoid named amorpha-4,11-diene (U.S. Pat. Nos. 7,172,886 and 7,192,751) Other efforts have focused on balancing the pool of glyceraldehyde-3-phosphate and pyruvate, or on increasing the expression of 1-deoxy-D-xylulose-5-phosphate synthase (dxs) and IPP isomerase (idi). See Farmer et al. (2001) *Biotechnol. Prog.* 17:57-61; Kajiwara et al. (1997) *Biochem. J.* 324:421-426; and Kim et al. (2001) *Biotechnol. Bioeng.* 72:408-415.

Nevertheless, given the very large quantities of isoprenoid products needed for many commercial applications, there remains a need for expression systems and fermentation procedures that produce even more isoprenoids than available with current technologies. Optimal redirection of microbial metabolism toward isoprenoid production requires that the introduced biosynthetic pathway is properly engineered both to funnel carbon to isoprenoid production efficiently and to prevent build up of toxic levels of metabolic intermediates over a sustained period of time. Provided herein are compositions and methods that address this need and provide related advantages as well.

SUMMARY OF THE INVENTION

Provided herein are compositions and methods for a robust production of isoprenoids. Non-limiting examples of suitable isoprenoids include: hemiterpenes (derived from 1 isoprene unit) such as isoprene; monoterpenes (derived from 2 isoprene units) such as myrcene; sesquiterpenes (derived from 3 isoprene units) such as amorpha-4,11-diene; diterpenes (derived from four isoprene units) such as taxadiene; triterpenes (derived from 6 isoprene units) such as squalene; tetraterpenes (derived from 8 isoprenoids) such as β-carotene; and polyterpenes (derived from more than 8 isoprene units) such as polyisoprene.

In one aspect, a method for producing an isoprenoid compound is provided wherein the method comprises:
  (a) obtaining a plurality of host cells that are capable of making the isoprenoid compound comprising a chromosomally integrated heterologous nucleic acid sequence encoding an enzyme of the MEV or DXP pathway;
  (b) culturing the host cells in a medium under conditions wherein the host cells use ethanol as a carbon source and make the isoprenoid compound; and
  (c) recovering the isoprenoid compound from the medium.

In some embodiments, the ethanol that is consumed by the host cells as the carbon source is made by the host cell. In other embodiments, the ethanol that is consumed by the host cells as the carbon source is exogenously supplied to the medium.

In another aspect, a method for making an isoprenoid compound is provided which comprises:
  (a) obtaining a plurality of host cells that are capable of making the isoprenoid compound;
  (b) culturing the host cells in a medium comprising ethanol in an amount equal to or greater than about 1 gram per liter of medium for at least four hours; and
  (c) recovering the isoprenoid compound from the medium.

In yet another aspect, a method for making an isoprenoid compound is provided which comprises:
  (a) obtaining a plurality of yeast cells that are capable of making the isoprenoid compound;
  (b) culturing the yeast cells to build biomass by providing a bolus of a carbon source to the medium;
  (c) maintaining the cells under conditions whereby the yeast cells have an ethanol consumption rate equal to or greater than about 0.01 gram per ethanol per gram of dry cell weight per hour for at least four hours; and (d) recovering the isoprenoid compound from the medium.

In some embodiments, the host cells make the isoprenoid compound using the MEV pathway. In other embodiments, the host cells make the isoprenoid compound using the DXP pathway.

In other embodiments, the host cells are cultured or maintained for at least some period of time under oxygen limited conditions. In still other embodiments, the host cells are cultured or maintained for at least some period of time under phosphate limited conditions.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIGS. 10A through 10D show dissolved oxygen concentration, growth, ethanol production/consumption, and amorpha-4,11-diene production by strain Y283 at different degrees of oxygen limitation.

DETAILED DESCRIPTION OF THE INVENTION

Definitions

Figure 1:
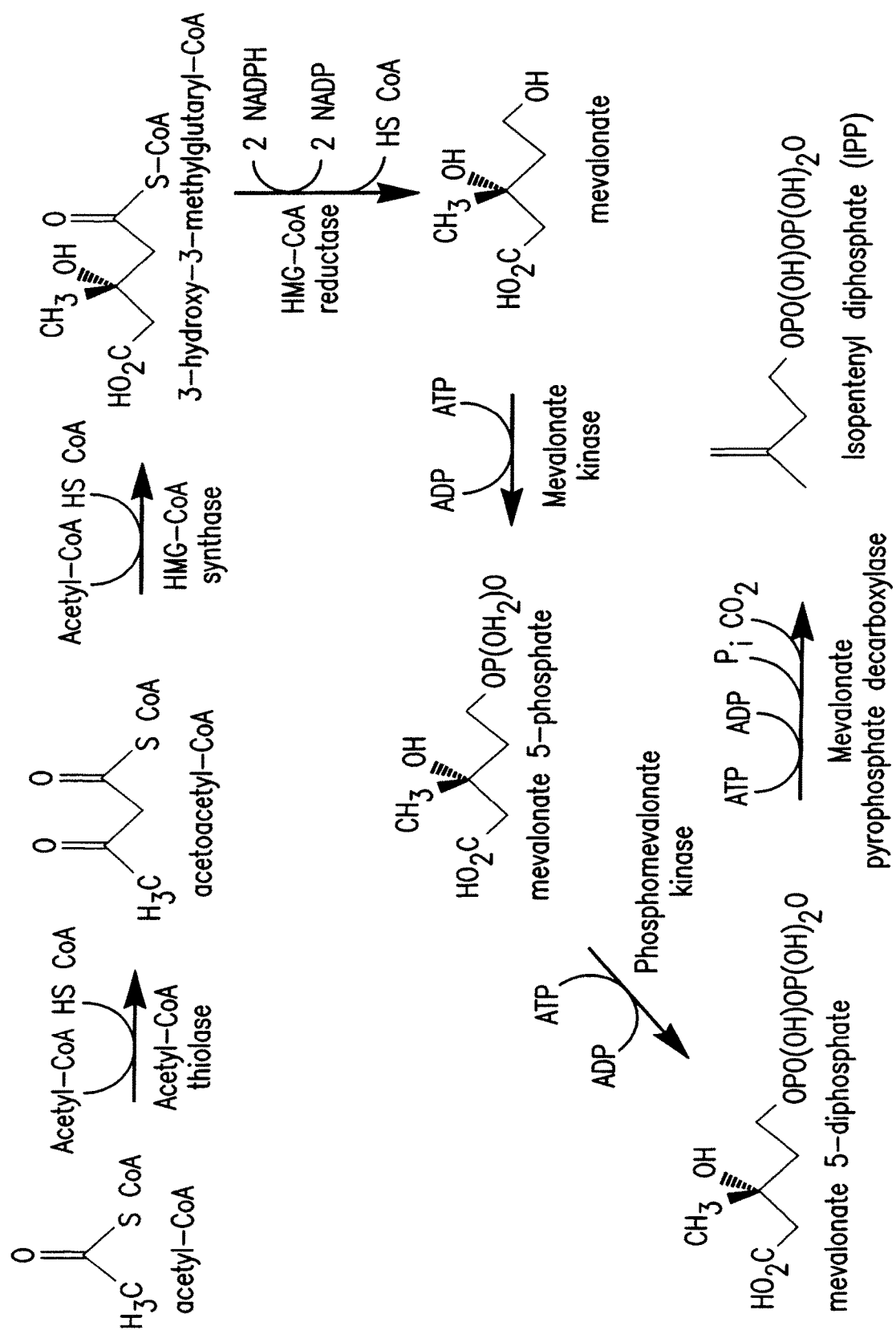
FIG. 1 is a schematic representation of the mevalonate ("MEV") pathway for the production of isopentenyl pyrophosphate ("IPP").

Unless defined otherwise, all technical and scientific terms used herein have the same meaning as commonly understood by one of ordinary skill in the art. Reference is made here to a number of terms that shall be defined to have the following meanings:

The term "optional" or "optionally" means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where the event or circumstance does not occur.

The terms "metabolic pathway" is used herein to refer to a catabolic pathway or an anabolic pathway. Anabolic pathways involve constructing a larger molecule from smaller molecules, a process requiring energy. Catabolic pathways involve breaking down of larger molecules, often releasing energy.

The term "mevalonate pathway" or "MEV pathway" is used herein to refer to the biosynthetic pathway that converts acetyl-CoA to IPP. The MEV pathway is illustrated schematically in FIG. 1.

The term "deoxyxylulose 5-phosphate pathway" or "DXP pathway" is used herein to refer to the pathway that converts glyceraldehyde-3-phosphate and pyruvate to IPP and DMAPP. The DXP pathway is illustrated schematically in FIG. 2.

The word "pyrophosphate" is used interchangeably herein with "diphosphate".

The terms "expression vector" or "vector" refer to a nucleic acid that transduces, transforms, or infects a host cell, thereby causing the cell to produce nucleic acids and/or proteins other than those that are native to the cell, or to express nucleic acids and/or proteins in a manner that is not native to the cell.

The term "endogenous" refers to a substance or process that occurs naturally, e.g., in a non-recombinant host cell.

The terms "enzymatic pathway for making isopentenyl pyrophosphate" refers to any pathway capable of producing isopentyl pyrophosphate, including, without limitation, either the mevalonate pathway or the DXP pathway.

The term "nucleic acid" refers to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically, or biochemically modified, non-natural, or derivatized nucleotide bases.

The term "operon" is used to refer to two or more contiguous nucleotide sequences that each encode a gene product such as a RNA or a protein, and the expression of which are coordinately regulated by one or more controlling elements (for example, a promoter).

The term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The term "protein" refers to a polymeric form of amino acids of any length, which can include coded and non-coded amino acids, chemically or biochemically modified or derivatized amino acids, and polypeptides having modified peptide backbones.

The term "heterologous nucleic acid" as used herein refers to a nucleic acid wherein at least one of the following is true: (a) the nucleic acid is foreign ("exogenous") to (that is, not naturally found in) a given host cell; (b) the nucleic acid comprises a nucleotide sequence that is naturally found in (that is, is "endogenous to") a given host cell, but the nucleotide sequence is produced in an unnatural (for example, greater than expected or greater than naturally found) amount in the cell; (c) the nucleic acid comprises a nucleotide sequence that differs in sequence from an endogenous nucleotide sequence, but the nucleotide sequence encodes the same protein (having the same or substantially the same amino acid sequence) and is produced in an unnatural (for example, greater than expected or greater than naturally found) amount in the cell; or (d) the nucleic acid comprises two or more nucleotide sequences that are not found in the same relationship to each other in nature (for example, the nucleic acid is recombinant).

A "transgene" refers to a gene that is exogenously introduced into a host cell. It can comprise an endogenous or exogenous, or heterologous nucleic acid.

The term "recombinant host" (also referred to as a "genetically modified host cell" or "genetically modified host microorganism") denotes a host cell that comprises a heterologous nucleic acid provided herein.

The term "exogenous nucleic acid" refers to a nucleic acid that is exogenously introduced into a host cell, and hence is not normally or naturally found in and/or produced by a given cell in nature.

The term "regulatory element" refers to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" refers to a permanent or transient genetic change induced in a cell following introduction of new nucleic acid. Genetic change ("modification") can be accomplished either by incorporation of the new DNA into the genome of the host cell, or by transient or stable maintenance of the new DNA as an episomal element. In eukaryotic cells, a permanent genetic change is generally achieved by introduction of the DNA into the genome of the cell. In prokaryotic cells, a permanent genetic change can be introduced into the chromosome or via extrachromosomal elements such as plasmids and expression vectors, which may contain one or more selectable markers to aid in their maintenance in the recombinant host cell.

The term "operably linked" refers to a juxtaposition wherein the components so described are in a relationship permitting them to function in their intended manner. For instance, a promoter is operably linked to a nucleotide sequence if the promoter affects the transcription or expression of the nucleotide sequence.

The term "host cell" and "host microorganism" are used interchangeably herein to refer to any archae, bacterial, or eukaryotic living cell into which a heterologous nucleic acid can be or has been inserted. The term also relates to the progeny of the original cell, which may not necessarily be completely identical in morphology or in genomic or total DNA complement to the original parent, due to natural, accidental, or deliberate mutation.

The term "synthetic" as used in reference to nucleic acids means the annealing of chemically synthesized oligonucleotide building blocks to form gene segments, which are then enzymatically assembled to construct the entire gene. Synthesis of nucleic acids via "chemical means" means that the component nucleotides were assembled in vitro.

The term "natural" as applied to a nucleic acid, a cell, or an organism, refers to a nucleic acid, cell, or organism that is found in nature. For example, a polypeptide or polynucleotide sequence that is present in a non-pathological (undiseased) organism that can be isolated from a source in nature and that has not been intentionally modified by a human in the laboratory is natural.

The term "naturally occurring" as applied to a nucleic acid, an enzyme, a cell, or an organism, refers to a nucleic acid, enzyme, cell, or organism that is found in nature. For example, a polypeptide or polynucleotide sequence that is present in an organism that can be isolated from a source in nature and that has not been intentionally modified by a human in the laboratory is naturally occurring.

The term "biologically active fragment" as applied to a protein, polypeptide or enzyme refers to functional portion (s) of the proteins or polypeptide or enzyme. Functionally equivalents may have variant amino acid sequences may arise, e.g., as a consequence of codon redundancy and functional equivalency which are known to occur naturally within nucleic acid sequences and the proteins thus encoded. Functionally equivalent proteins or peptides may alternatively be constructed via the application of recombinant DNA technology, in which changes in the protein structure may be engineered, based on considerations of the properties of the amino acids being exchanged.

The terms "isoprenoid", "isoprenoid compound", "isoprenoid product", "terpene", "terpene compound", "terpenoid", and "terpenoid compound" are used interchangeably herein. They refer to compounds that are capable of being derived from IPP.

The singular forms "a," "and," and "the" include plural referents unless the context clearly dictates otherwise. Thus, for example, reference to "an expression vector" includes a single expression vector as well as a plurality of expression vectors, and reference to "the host cell" includes reference to one or more host cells, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Unless otherwise indicated, the embodiments provided herein are not limited to particular sequences, expression vectors, enzymes, host microorganisms, or processes, as such may vary in accordance with the understanding of those of ordinary skill in the art in view of the teaching herein. Terminology used herein is for purposes of describing particular embodiments only and is not intended to be limiting.

IPP Pathways

The host cells provided herein comprise or utilize the MEV pathway, the DXP pathway or both to synthesize IPP and its isomer, DMAPP. Provided herein is the host cell includes at least one chromosomally integrated heterologous nucleic acid sequence encoding an enzyme of the MEV or DXP pathways. In other embodiments, the host cell includes at least one heterologous nucleic acid sequence encoding a plurality of enzymes of the MEV or DXP pathways. In still other embodiments, the host cell includes a plurality of heterologous nucleic acid sequences encoding all of the MEV pathway enzymes. In yet other embodiments, the host cell includes a plurality of heterologous nucleic acid sequences that encodes all of the DXP pathway enzymes.

In general, eukaryotes other than plants use the MEV isoprenoid pathway exclusively to convert acetyl-CoA to IPP, which is subsequently isomerized to DMAPP. Prokaryotes, with some exceptions, use the mevalonate-independent or DXP pathway to produce IPP and DMAPP separately through a branch point. Plants use both the MEV and DXP pathways for IPP synthesis.

MEV Pathway

A schematic representation of the MEV pathway is described in FIG. 1. In general, the pathway comprises six steps.

In the first step, two molecules of acetyl-coenzyme A are enzymatically combined to form acetoacetyl-CoA. An enzyme known to catalyze this step is, for example, acetyl-CoA thiolase (also known as acetyl-CoA acetyltransferase). Illustrative examples of nucleotide sequences include but are not limited to the following GenBank accession numbers and the organism from which the sequences derived: (NC_000913 REGION: 2324131 . . . 2325315; *Escherichia coli*), (D49362; *Paracoccus denitrificans*), and (L20428; *Saccharomyces cerevisiae*).

In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Illustrative examples of nucleotide sequences include but are not limited to: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In the third step, HMG-CoA is enzymatically converted to mevalonate. An enzyme known to catalyze this step is, for example, HMG-CoA reductase. Illustrative examples of nucleotide sequences include but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*).

In the fourth step, mevalonate is enzymatically phosphorylated to form mevalonate 5-phosphate. An enzyme known to catalyze this step is, for example, mevalonate kinase. Illustrative examples of nucleotide sequences include but are not limited to: (L77688; *Arabidopsis thaliana*), and (X55875; *Saccharomyces cerevisiae*).

In the fifth step, a second phosphate group is enzymatically added to mevalonate 5-phosphate to form mevalonate 5-pyrophosphate. An enzyme known to catalyze this step is, for example, phosphomevalonate kinase. Illustrative examples of nucleotide sequences include but are not limited to: (AF429385; *Hevea brasiliensis*), (NM_006556; *Homo sapiens*), and (NC_001145. complement 712315 . . . 713670; *Saccharomyces cerevisiae*).

In the sixth step, mevalonate 5-pyrophosphate is enzymatically converted into IPP. An enzyme known to catalyze this step is, for example, mevalonate pyrophosphate decarboxylase. Illustrative examples of nucleotide sequences include but are not limited to: (X97557; *Saccharomyces cerevisiae*), (AF290095; *Enterococcus faecium*), and (U49260; *Homo sapiens*).

If IPP is to be converted to DMAPP, then a seventh step is required. An enzyme known to catalyze this step is, for example, IPP isomerase. Illustrative examples of nucleotide sequences include but are not limited to: (NC_000913, 3031087 . . . 3031635; *Escherichia coli*), and (AF082326; *Haematococcus pluvialis*). If the conversion to DMAPP is required, an increased expression of IPP isomerase ensures that the conversion of IPP into DMAPP does not represent a rate-limiting step in the overall pathway.

DXP Pathway

Figure 2:
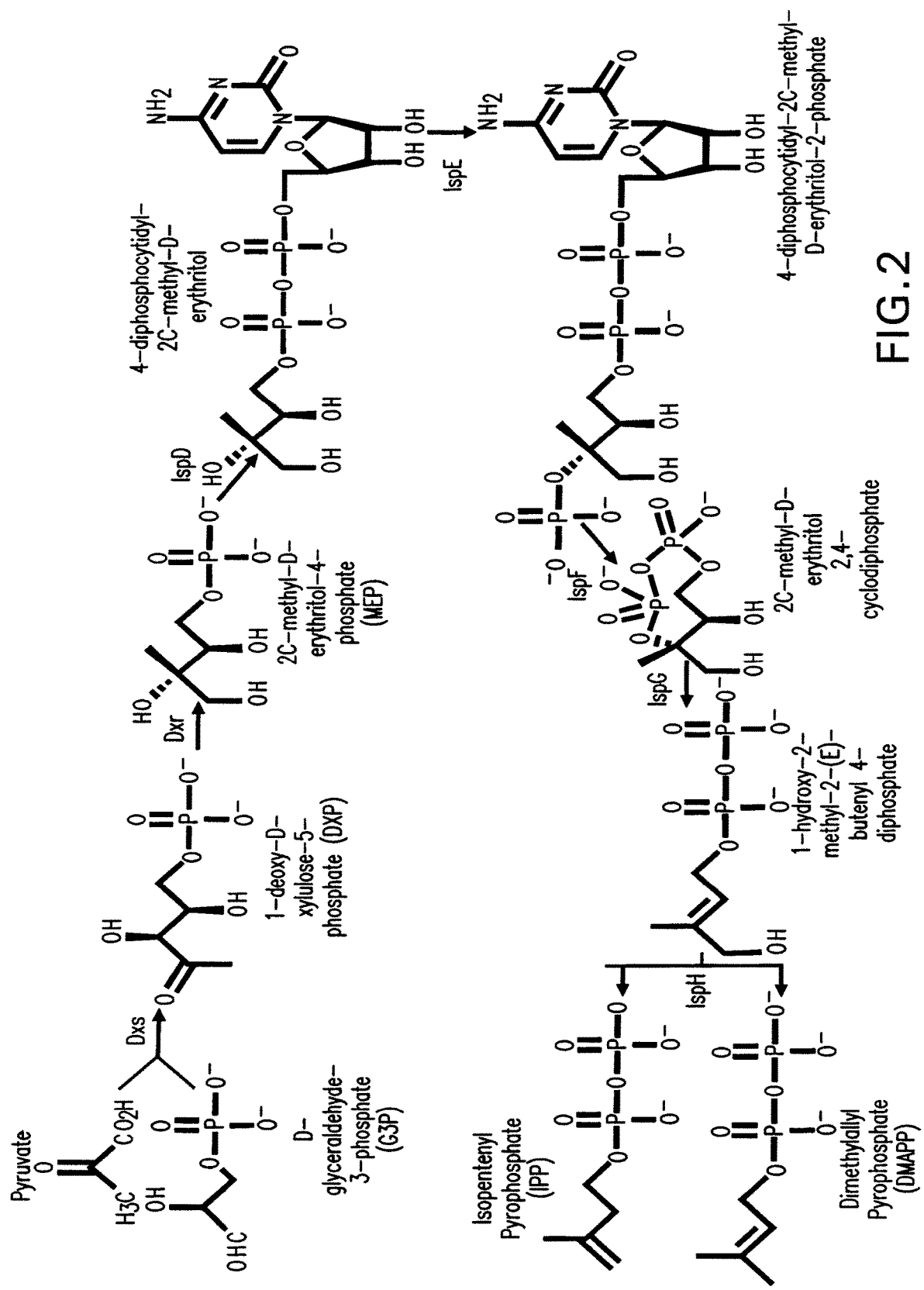
FIG. 2 is a schematic representation of the 1-deoxy-D-xylulose 5-diphosphate ("DXP") pathway for the production of isopentenyl pyrophosphate ("IPP") and dimethylallyl pyrophosphate ("DMAPP"). Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritol synthase; IspF is 2C-methyl-D-erythritol 2,4-cyclodiphosphate synthase; IspG is 1-hydroxy-2-methyl-2-(E)-butenyl 4-diphosphate synthase (IspG); and ispH is isopentenyl/dimethylallyl diphosphate synthase.

A schematic representation of the DXP pathway is described in FIG. 2. In general, the DXP pathway comprises seven steps. In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Illustrative examples of nucleotide sequences include but are not limited to: (AF035440; *Escherichia coli*), (NC_002947, locus tag PP0527; *Pseudomonas putida* KT2440), (CP000026, locus tag SPA2301; *Salmonella enterica* Paratyphi, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC_004556, locus tag PD1293; *Xylella fastidiosa* Temecula1), and (NC_003076, locus tag AT5G11380; *Arabidopsis thaliana*).

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP_2709; *Rhodobacter sphaeroides* 2.4.1), and (NC_007492, locus tag Pfl_1107; *Pseudomonas fluorescens* PfO-1).

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Illustrative examples of nucleotide sequences include but are not limited to: (AF230736; *Escherichia coli*), (NC_007493, locus_tag RSP_2835; *Rhodobacter sphaeroides* 2.4.1), (NC_003071, locus_tag AT2G02500; *Arabidopsis thaliana*), and (NC_002947, locus_tag PP1614; *Pseudomonas putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Illustrative examples of nucleotide sequences include but are not limited to: (AF216300; *Escherichia coli*) and (NC_007493, locus_tag RSP_1779; *Rhodobacter sphaeroides* 2.4.1).

In the fifth step, 4-diphosphocytidyl-2C-methyl-D-erythritol-2-phosphate is converted to 2C-methyl-D-erythritol 2,4-cyclodiphosphate. An enzyme known to catalyze this step is, for example, 2C-methyl-D-erythritol 2,4-cyclodiphosphate synthase. Illustrative examples of nucleotide sequences include but are not limited to: (AF230738; *Escherichia coli*), (NC_007493, locus_tag RSP_6071; *Rhodobacter sphaeroides* 2.4.1), and (NC_002947, locus_tag PP1618; *Pseudomonas putida* KT2440).

In the sixth step, 2C-methyl-D-erythritol 2,4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Illustrative examples of nucleotide sequences include but are not limited to: (AY033515; *Escherichia coli*), (NC_002947, locus_tag PP0853; *Pseudomonas putida* KT2440), and (NC_007493, locus_tag RSP_2982; *Rhodobacter sphaeroides* 2.4.1).

In the seventh step, 1-hydroxy-2-methyl-2-(E)-butenyl-4-diphosphate is converted into either IPP or its isomer, DMAPP. An enzyme known to catalyze this step is, for example, isopentyl/dimethylallyl diphosphate synthase. Illustrative examples of nucleotide sequences include but are not limited to: (AY062212; *Escherichia coli*) and (NC_002947, locus_tag PP0606; *Pseudomonas putida* KT2440).

In some embodiments, "cross talk" (or interference) between the host cell's own metabolic processes and those processes involved with the production of IPP as provided herein are minimized or eliminated entirely. For example, cross talk is minimized or eliminated entirely when the host microorganism relies exclusively on the DXP pathway for synthesizing IPP, and a MEV pathway is introduced to provide additional IPP. Such a host organisms would not be equipped to alter the expression of the MEV pathway enzymes or process the intermediates associated with the MEV pathway. Organisms that rely exclusively or predominately on the DXP pathway include, for example, *Escherichia coli*.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

Host Cells

Illustrative examples of suitable host cells for use provided herein include any archae, prokaryotic, or eukaryotic cell. Examples of an archae cell include, but are not limited to those belonging to the genera: *Aeropyrum, Archaeglobus, Halobacterium, Methanococcus, Methanobacterium, Pyrococcus, Sulfolobus,* and *Thermoplasma.* Illustrative examples of archae strains include but are not limited to: *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum, Thermoplasma volcanium.*

Examples of a procaryotic cell include, but are not limited to those belonging to the genera: *Agrobacterium, Aliyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus,* and *Zymomonas.*

Illustrative examples of prokaryotic bacterial strains include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus,* and the like.

In general, if a bacterial host cell is used, a non-pathogenic strain is preferred. Illustrative examples of non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum,* and the like.

Examples of eukaryotic cells include but are not limited to fungal cells. Examples of fungal cell include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces, Trichoderma* and *Xanthophyllomyces* (formerly *Phaffia*).

Illustrative examples of eukaryotic strains include but are not limited to: *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccharomyces bayanus, Saccharomyces boulardi, Saccharomyces cerevisiae, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Trichoderma reesei* and *Xanthophyllomyces dendrorhous* (formerly *Phaffia rhodozyma*).

In general, if a eukaryotic cell is used, a non-pathogenic strain is preferred. Illustrative examples of non-pathogenic strains include but are not limited to: *Fusarium graminearum, Fusarium venenatum, Pichia pastoris, Saccaromyces boulardi,* and *Saccaromyces cerevisiae.*

In addition, certain strains have been designated by the Food and Drug Administration as GRAS or Generally Regarded As Safe. These strains include: *Bacillus subtilis, Lactibacillus acidophilus, Lactobacillus helveticus,* and *Saccharomyces cerevisiae.*

Isoprenoid Compounds

The host cells provided herein are used to make isoprenoids. Specific isoprenoid compounds are made from IPP or DMAPP and may require additional finishing enzymes. Non-limiting examples of suitable isoprenoids include: hemiterpenes (derived from 1 isoprene unit) such as isoprene; monoterpenes (derived from 2 isoprene units) such as myrcene; sesquiterpenes (derived from 3 isoprene units) such as amorpha-4,1-diene; diterpenes (derived from four isoprene units) such as taxadiene; triterpenes (derived from 6 isoprene units) such as squalene; tetraterpenes (derived from 8 isoprenoids) such as carotene; and polyterpenes (derived from more than 8 isoprene units) such as polyisoprene. In some embodiments, the isoprenoid is not a carotenoid. In other embodiments, the isoprenoid is a $C_5$-$C_{20}$ isoprenoid. Illustrative examples of specific $C_5$-$C_{20}$ isoprenoid compounds and their respective finishing enzymes are further described below.

$C_5$ Compounds $C_5$ compounds provided herein generally are derived from IPP or DMAPP. These compounds are also known as hemiterpenes because they are derived from a single isoprene unit (IPP or DMAPP).

Isoprene

Isoprene, whose structure is

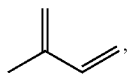

is found in many plants. Isoprene is made atom IPP by isoprene synthase. Illustrative examples of suitable nucleotide sequences include but are not limited to: (AB198190; *Populus alba*) and (AJ294819; *Polulus alba×Polulus tremula*).

$C_{10}$ Compounds $C_{10}$ compounds provided herein generally derived from geranyl pyrophosphate (GPP) which is made by the condensation of IPP with DMAPP. An enzyme known to catalyze this step is, for example, geranyl pyrophosphate synthase. These $C_{10}$ compounds are also known as monoterpenes because they are derived from two isoprene units.

Figure 3:
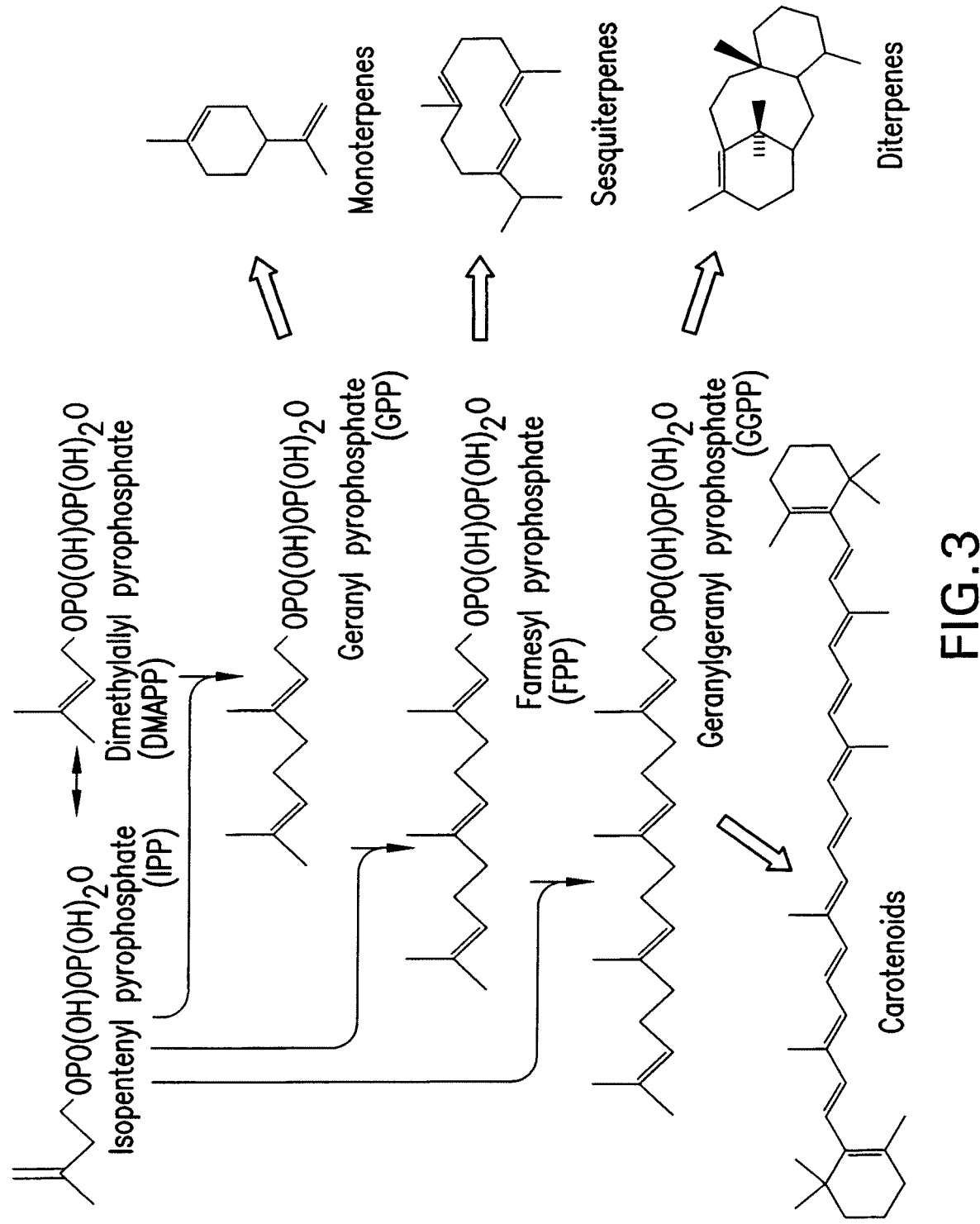
FIG. 3 is a schematic representation of the conversion of isopentenyl pyrophosphate ("IPP") and dimethylallyl pyrophosphate ("DMAPP") to geranyl pyrophosphate ("GPP"), farnesyl pyrophosphate ("FPP"), and geranylgeranyl pyrophosphate ("GGPP"), and the synthesis of various isoprenoids.

FIG. 3 shows schematically how IPP and DMAPP can produce GPP, which can be further processed to a monoterpene.

Illustrative examples of nucleotide sequences for geranyl pyrophosphate synthase include but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Menthaxpiperita*), (AF182827; *Menthaxpiperita*), (MP1249453; *Menthaxpiperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

GPP is then subsequently converted to a variety of $C_{10}$ compounds. Illustrative examples of $C_{10}$ compounds include but are not limited:

Carene

Carene, whose structure is

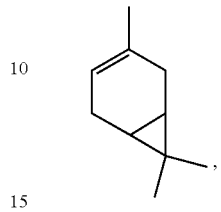

is found in the resin of many trees, particularly pine trees. Carene is made from GPP from carene synthase. Illustrative examples of suitable nucleotide sequences include but are not limited to: (AF461460, REGION 43 . . . 1926; *Picea abies*) and (AF527416, REGION: 78 . . . 1871; *Salvia stenophylla*).

Geraniol

Geraniol (also known as rhodnol), whose structure is

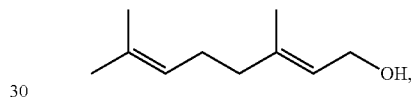

is the main component of oil-of-rose and palmarosa oil. It also occurs in geranium, lemon, and citronella. Geraniol is made from GPP by geraniol synthase. Illustrative examples of suitable nucleotide sequences include but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*)

Linalool

Linalool, whose structure is

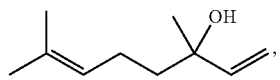

is found in many flowers and spice plants such as coriander seeds. Linalool is made from GPP by linalool synthase. Illustrative examples of a suitable nucleotide sequence include but are not limited to: (AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM_463918; *Oryza sativa*), (AP004078, Locus BAD07605; *Oryza saliva*), (XM_463918, Locus XP_463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. crispa cultivar No. 79).

Limonene

Limonene, whose structure is

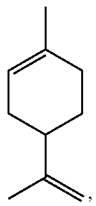

is found in the rind of citrus fruits and peppermint. Limonene is made from GPP by limonene synthase. Illustrative examples of suitable nucleotide sequences include but are not limited to: (+)-limonene synthases (AF514287, REGION: 47 . . . 1867; *Citrus limon*) and (AY055214, REGION: 48 . . . 1889; *Agastache rugosa*) and (−)-limonene synthases (DQ195275, REGION: 1 . . . 1905; *Picea sitchensis*), (AF006193, REGION: 73 . . . 1986; *Abies grandis*), and (MHC4SLSP, REGION: 29 . . . 1828; *Mentha spicata*).

Myrcene

Myrcene, whose structure is

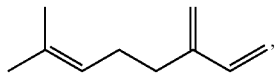

is found in the essential oil in many plants including bay, verbena, and myrcia from which it gets its name. Myrcene is made from GPP by myrcene synthase. Illustrative examples of suitable nucleotide sequences include but are not limited to: (U87908; *Abies grandis*), (AY195609; *Antirrhinum majus*), (AY195608; *Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

Ocimene

α- and β-Ocimene, whose structures are

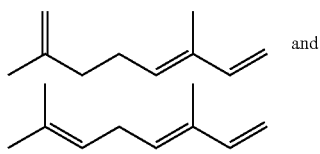 and respectively, are found in a variety of plants and fruits including *Ocimum basilicum* and is made from GPP by ocimene synthase. Illustrative examples of suitable nucleotide sequences include but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

α-Pinene

α-Pinene, whose structure is

is found in pine trees and eucalyptus. α-Pinene is made from GPP by α-pinene synthase. Illustrative examples of suitable nucleotide sequences include but are not limited to: (+) α-pinene synthase (AF543530, REGION: 1 . . . 1887; *Pinus taeda*), (−)α-pinene synthase (AF543527, REGION: 32 . . . 1921; *Pinus taeda*), and (+)/(−) α-pinene synthase (AGU87909, REGION: 6111892; *Abies grandis*).

β-Pinene

β-Pinene, whose structure is

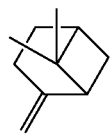

is found in pine trees, rosemary, parsley, dill, basil, and rose. β-Pinene is made from GPP by β-pinene synthase. Illustrative examples of suitable nucleotide sequences include but are not limited to: (−) β-pinene synthases (AF276072, REGION: 1 . . . 1749; *Artemisia annua*) and (AF514288, REGION: 26 . . . 1834; *Citrus limon*).

Sabinene

Sabinene, whose structure is

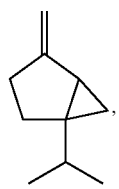

is found in black pepper, carrot seed, sage, and tea trees. Sabinene is made from GPP by sabinene synthase. An illustrative example of a suitable nucleotide sequence includes but is not limited to AF051901, REGION: 26 . . . 1798 from *Salvia officinalis*.

γ-Terpinene

γ-Terpinene, whose structure is

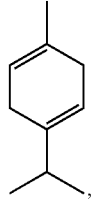

is a constituent of the essential oil from citrus fruits. Biochemically, γ-terpinene is made from GPP by a γ-terpinene synthase. Illustrative examples of suitable nucleotide sequences include: (AF514286, REGION: 30 . . . 1832 from *Citrus limon*) and (AB110640, REGION 1 . . . 1803 from *Citrus unshiu*).

Terpinolene

Terpinolene, whose structure is

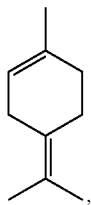

is found in black currant, cypress, guava, lychee, papaya, pine, and tea. Terpinolene is made from GPP by terpinolene synthase. An illustrative example of a suitable nucleotide sequence includes but is not limited to AY906866, REGION: 10 . . . 1887 from *Pseudotsuga menziesii*.

$C_{15}$ Compounds $C_{15}$ compounds provided herein generally derive from farnesyl pyrophosphate (FPP) which is made by the condensation of two molecules of IPP with one molecule of DMAPP. An enzyme known to catalyze this step is, for example, farnesyl pyrophosphate synthase. These $C_{15}$ compounds are also known as sesquiterpenes because they are derived from three isoprene units.

FIG. 3 shows schematically how IPP and DMAPP can be combined to produce FPP, which can be further processed to a sesquiterpene.

Illustrative examples of nucleotide sequences for farnesyl pyrophosphate synthase include but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), and (MZEFPS; *Zea mays*).

Alternatively, FPP can also be made by adding IPP to GPP. Illustrative examples of nucleotide sequences encoding for an enzyme capable of this reaction include but are not limited to: (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar Copenhageni str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP 779706; *Xylella fastidiosa* Temecula1).

FPP is then subsequently converted to a variety of $C_{15}$ compounds. Illustrative examples of $C_{15}$ compounds include but are not limited to:

Amorphadiene

Amorphadiene, whose structure is

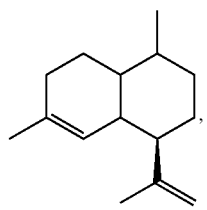

is a precursor to artemisinin which is made by *Artemisia anna*. Amorphadiene is made from FPP by amorphadiene synthase. An illustrative example of a suitable nucleotide sequence is SEQ ID NO. 37 of U.S. Pat. No. 7,192,751.

α-Farnesene

α-Farnesene, whose structure is

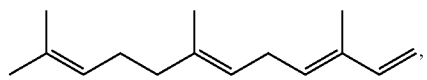

is found in various biological sources including but not limited to the Dufour's gland in ants and in the coating of apple and pear peels. α-Farnesene is made from FPP by α-farnesene synthase. Illustrative examples of suitable nucleotide sequences include but are not limited to DQ309034 from *Pyrus communis* cultivar d'Anjou (pear; gene name AFS1) and AY182241 from *Malus domestica* (apple; gene AFS1). Pechouus et al., *Planta* 219(1):84-94 (2004).

β-Farnesene

β-Farnesene, whose structure is

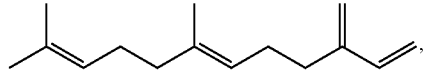

is found in various biological sources including but not limited to aphids and essential oils such as from peppermint. In some plants such as wild potato, β-farnesene is synthesized as a natural insect repellent. β-Farnesene is made from FPP by β-farnesene synthase. Illustrative examples of suitable nucleotide sequences include but is not limited to GenBank accession number AF024615 from *Menthaxpiperita* (peppermint; gene Tspa11), and AY835398 from *Artemisia annua*. Picaud et al., *Phytochemistry* 66(9): 961-967 (2005).

Farnesol

Farnesol, whose structure is

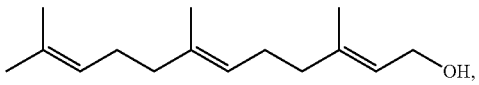 [SMILES: CC(C)=CCC/C(C)=C/CC/C(C)=C/CO]

is found in various biological sources including insects and essential oils such as from cintronella, neroli, cyclamen, lemon grass, tuberose, and rose. Farnesol is made from FPP by a hydroxylase such as farnesol synthase. Illustrative examples of suitable nucleotide sequences include but are not limited to GenBank accession number AF529266 from *Zea mays* and YDR481C from *Saccharomyces cerevisiae* (gene Pho8). Song, L., *Applied Biochemistry and Biotechnology* 128:149-158 (2006).

Nerolidol

Nerolidol, whose structure is

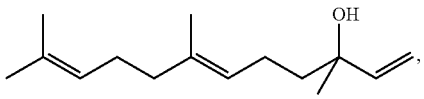 [SMILES: C=CC(C)(O)CC/C=C(\C)CCC=C(C)C]

is also known as peruviol, and is found in various biological sources including as essential oils such as from neroli, ginger, jasmine, lavender, tea tree, and lemon grass. Nerolidol is made from FPP by a hydroxylase such as nerolidol synthase. An illustrative example of a suitable nucleotide sequence includes but is not limited to AF529266 from *Zea mays* (maize; gene tps1).

Patchoulol

Patchoulol, whose structure is

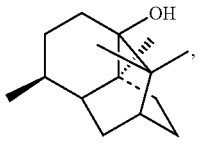

is also known as patchouli alcohol and is a constituent of the essential oil of *Pogostemon patchouli*. Patchouliol is made from FPP by patchouliol synthase. An illustrative example of a suitable nucleotide sequence includes but is not limited to AY508730 REGION: 1 . . . 1659 from *Pogostemon cablin*.

Valencene

Valencene, whose structure is

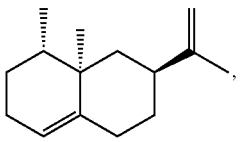

is one of the main chemical components of the smell and flavour of oranges and is found in orange peels. Valencene is made from FPP by nootkatone synthase. Illustrative examples of suitable nucleotide sequence includes but is not limited to AF441124 REGION: 1 . . . 1647 from *Citrus sinensis* and AY917195 REGION: 1 . . . 1653 from *Perilla frutescens*.

$C_{20}$ Compounds $C_{20}$ compounds provided herein generally derived from geranylgeraniol pyrophosphate (GGPP) which is made by the condensation of three molecules of IPP with one molecule of DMAPP. An enzyme known to catalyze this step is, for example, geranylgeranyl pyrophosphate synthase. These $C_{20}$ compounds are also known as diterpenes because they are derived from four isoprene units.

FIG. 3 shows schematically how IPP and DMAPP can be combined to produce GGPP, which can be further processed to a diterpene, or can be further processed to produce a carotenoid.

Illustrative examples of nucleotide sequences for geranylgeranyl pyrophosphate synthase include but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar israelensis, ATCC 35646 sq 1563), (CRGGPPS; *Catharanthus roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MC1276129; *Mucor circinelloides* f. *lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus acidotrophicus* SB), and (NC_006840, Locus YP_204095; *Vibrio fischeri* ES114).

Alternatively, GGPP can also be made by adding IPP to FPP. Illustrative examples of nucleotide sequences encoding an enzyme capable of this reaction include but are not limited to: (NM_12315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

GGPP is then subsequently converted to a variety of $C_{20}$ isoprenoids. Illustrative examples of $C_{20}$ compounds include but are not limited to:

Geranylgeraniol

Geranylgeraniol, whose structure is

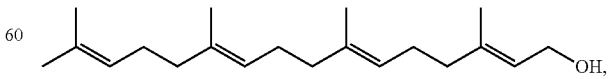

is a constituent of wood oil from *Cedrela toona* and of linseed oil. Geranylgeraniol can be made by e.g., adding to the expression constructs a phosphatase gene after the gene for a GGPP synthase.

Abietadiene
Abietadiene encompasses the following isomers:

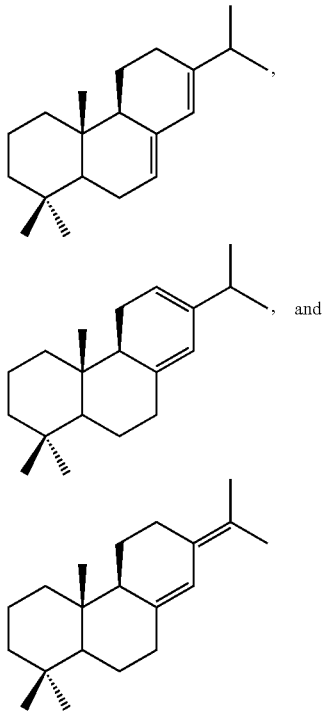

and is found in trees such as *Abies grandis*. Abietadiene is made by abietadiene synthase. An illustrative example of a suitable nucleotide sequence includes but are not limited to: (U50768; *Abies grandis*) and (AY473621; *Picea abies*).

$C_{20+}$ Compounds $C_{20+}$ compounds are also within the scope provided herein. Illustrative examples of such compounds include sesterterpenes ($C_{25}$ compound made from five isoprene units), triterpenes ($C_{30}$ compounds made from six isoprene units), and tetraterpenes ($C_{40}$ compound made from eight isoprene units). These compounds are made by using similar methods described herein and substituting or adding nucleotide sequences for the appropriate synthase(s).

High Yields of Isoprenoid Compounds

Provided herein are compositions and methods for a robust production of isoprenoids by culturing or maintaining the host cells under conditions in which ethanol is used as a carbon source. Using the methods described herein, the host cells produce more than about 5 grams of isoprenoid per liter of fermentation reaction mixture (5 g/L). In other embodiments, more than about 10 g/L, more than about 15 g/L, more than about 20 g/L, more than 25 g/L is produced, or more than about 30 g/L of isoprenoid is produced.

Alternatively isoprenoid production can be expressed in terms of specific productivity instead of yields. For example, using the methods described herein, the host cells produce more about 50 milligrams of isoprenoid per gram of dry host cells. In other embodiments, more than about 100 milligrams per gram dry cell weight, more than about 150 milligrams per gram dry cell weight, more than about 200 milligrams per gram dry cell weight, more than about 250 milligrams per gram dry cell weight, more than about 500 milligrams per gram dry cell weight, more than about 750 milligrams per gram dry cell weight, or more than about 1000 milligrams per gram dry cell weight of isoprenoid is produced.

Whether the production level is expressed in terms of yield or specific productivity, production occurs in less than about 120 hours, less than about 96 hours, less than about 72 hours, preferably less than about 48 hours, or even less than about 24 hours.

The methods provided herein can be carried out in a batch, a fed-batch, or a continuous process. A batch process is typically a closed process where all of the raw materials are added at the beginning of the process. A fed-batch process is typically a closed process where the carbon source and/or other substrates are added in increments throughout the process. A fed-batch process allows for greater control of the medium and the growth of the microorganisms. A continuous process can be considered an open system where medium is continuously added and product is simultaneously removed.

Processes in between fed-batch and continuous processes can also be used. For example, in one embodiment, the process is begun as a fed-batch process, and an organic layer, is placed in contact with the culturing medium while the process continues. Isoprenoids, which typically have a higher solubility in an organic solution than in an aqueous solution, are extracted out of the medium into the organic layer. Because product is removed from the medium, this method has characteristics of both a fed-batch and a continuous process.

Product removal through an organic overlay (e.g. dodecane, isopropyl myristate, methyl oleate and the like) can often lead to increases in isoprenoid production. Product removal can lead to production increases and is desirable particularly where product accumulation leads to pathway inhibition. In certain embodiments, the organic layer can be formed by the isoprenoid product itself. This occurs where the isoprenoid is produced in excess of its saturation point and form a layer separable from the aqueous medium.

In some embodiments, ethanol is the sole carbon source for host cells. In other embodiments, the carbon source includes both ethanol and a non-ethanol carbon source. In still other embodiments, the non-ethanol carbon source is a carbohydrate.

Illustrative examples of carbohydrates include monosaccharides, disaccharides, and combinations thereof. Some non-limiting examples of suitable monosaccharides include glucose, galactose, mannose, fructose, ribose, and combinations thereof. Some non-limiting examples of suitable disaccharides include sucrose, lactose, maltose, trehalose, cellobiose, and combinations thereof. Some non-limiting examples of suitable polysaccharides include starch, glycogen, cellulose, chitin, and combinations thereof. Other sources of carbohydrates include cane juice and molasses.

In general, polysaccharides are first converted into monosaccharides and oligosaccharides by chemical means or by enzymatic methods before they used as a source of carbon for host cells. For instance, cellulose can be converted into glucose by the enzyme cellulase. In certain embodiments, after the breakdown of the polysaccharide, the monosaccharide and/or oligosaccharide constitute at least about 50% by weight of the carbon source as determined at the beginning of the fermentation. In other embodiments, the monosaccharide and/or oligosaccharide constitute at least about 80% or even 90% by weight of the carbon source as determined at the beginning of the fermentation, such that the fermentation medium is essentially free of cellulose.

In certain embodiments, the host cells are exogenously provided ethanol as a carbon source. In other embodiments, the ethanol that is consumed by the host cells as the carbon source was made by the host cells. In other words, the host cells are provided a non-ethanol carbon source (typically a carbohydrate) which is converted by the host cells into ethanol and the ethanol is subsequently consumed by the host cells.

The host cells' use of ethanol can be quantified in a number of ways. In one method, ethanol concentration is used. In addition to being a carbon source, the presence of ethanol in the medium also has the beneficial effects of deterring microbial contaminants.

Thus, in one embodiment, the ethanol concentration in the medium is at least about 1 gram per liter of medium for at least 4 hours. The ethanol concentration can be determined by any method known in the art. It can be measured directly by sampling the medium or indirectly by sampling the offgas. If an indirect method is used such as offgas analysis by mass spectrophotometer, a correlation first be must be established between the offgas measurements in parts per million and the direct measurements of ethanol in the medium. In other embodiments, the ethanol concentration in the medium is between about 1 and about 5 grams, between about 1 and about 10 grams, or between about 1 and about 20 grams per liter of medium. In still other embodiments, the ethanol concentration in the medium is greater than about 10 grams per liter of medium or greater than about 20 grams per liter of medium. In yet other embodiments, the above ethanol concentrations are maintained for at least 6 hours, 8 hours, 10 hours, 12 hours, 24 hours, or 48 hours.

However, host cells can be using ethanol as a carbon source but still have undetectable levels of ethanol or have ethanol concentration close to zero. For example, this can occur when the host cells are consuming ethanol as fast as the ethanol is being supplied. As a result, provided herein are alternative measures for the host cells' ethanol utilization.

In another embodiment, the host cells have a specific ethanol consumption rate of at least 0.01 gram of ethanol per gram of dry cell weight per hour. In other embodiments, the specific ethanol consumption rate is between about 0.01 and about 0.20 gram of ethanol, or between about 0.02 and about 0.10 gram of ethanol per gram of dry cell weight per hour. In still other embodiments, the specific ethanol consumption rate is greater than about 0.10 gram of ethanol per gram of dry cell weight per hour. The specific ethanol consumption rate is maintained for at least 4 hours, 6 hours, 8 hours, 10 hours, 12 hours, 24 hours, or 48 hours.

Alternatively, specific ethanol consumption rate is expressed in terms of grams of ethanol per gram of dry cell weight per day. In some embodiments, the host cells have a specific ethanol consumption rate of at least 0.2 grams of ethanol per gram of dry cell weight per day. In some embodiments, the specific ethanol consumption rate is between about 0.2 and about 5 grams or between about 0.5 and about 3 of ethanol per gram of dry cell weight per day. In other embodiments, the specific ethanol consumption rate is greater than about 3 grams of ethanol per gram of dry cell weight per day.

In certain embodiments, the cells are cultured or maintained under conditions that are not limited by oxygen. In other words, the cells are under aerobic conditions.

However, maintaining fully aerobic conditions can be challenging particularly in large scale processes oxygen due to limitations of mass transfer and the relatively low solubility of oxygen in aqueous solutions. For example, if air is used to sparge into tanks, the solubility of oxygen in water is 9 milligrams per liter at 20° C. If pure oxygen is used instead of air, then the solubility increases to 43 milligrams per liter. In either case (sparging air or pure oxygen), this amount of oxygen is depleted in seconds by an active and concentrated microbial population unless oxygen is continuously supplied. In comparison, the amounts of other nutrients that are used by the cells during the same period (seconds, e.g., less than a minute) are neglible compared to the bulk concentrations.

We have found that the host cells provided herein are able to tolerate some period of oxygen limitation is and still make high levels of isoprenoid compounds. This flexibility allows for a more economical process by providing savings in terms of tank design, decreased demain for oxygen gas, lower energy costs for aeration and the like. Moreover, under certain circumstances, oxygen limitation appears to be beneficial. Without being bound by theory, cell growth under oxygen limited conditions appears to allow more of the carbon to be directed to product instead of biomass or loss through carbon dioxide.

As a consequence, in certain other embodiments, the host cells are cultured or maintained under conditions that are oxygen limited. The periods of oxygen limitation include at least 4 hours, at least 6 hours, at least 8 hours, at least 10 hours, at least 12 hours, at least 24 hours, or at least 48 hours.

Oxygen limitation occurs when the specific growth rate of the host cells is less than the maximum specific growth rate where oxygen is not limiting (e.g., provided in excess). Specific growth rate is the rate of growth of cells per unit of biomass per unit time and has the units of reciprocal time (1/t). The maximum specific growth rate for cells in a culture medium relates to the effect of a substrate concentration on growth rate which in this case is oxygen. Generally, cells will grow slowly at a low level of the substrate, and as the level of the substrate in the medium increases, so does the rate of cell growth. However, the rate of cell growth does not continue to rise indefinitely, and at high levels of substrate, a given increase in the amount of substrate will produce a smaller and smaller increase in the rate of cell growth. Therefore, the growth rate ultimately reaches a limit, which is often referred to as the maximum specific growth rate.

A theoretical treatment of the relationship between growth rates in culture is well known to those skilled in the art, and is referred to as the Monod equation. See, for example, Pirt, Principles of Microbe and Cell Cultivation, Wiley, N.Y., 1975, pages 4-10. In this theoretical treatment, the maximum specific rate is an asymptotic limit that is never reached until an infinite level of substrate is reached. In practice, however, the maximum specific growth rate can be considered as being obtained when the conditions under investigation (e.g., a substrate level such as oxygen) support the fastest initial growth rate. For instance, in a fed-batch reactor, the initial condition where all substrates required for growth (e.g. nutrients and oxygen) are supplied in excess and fermentation occurs at the optimal temperature for the host cell is treated as the conditions for the maximum growth rate. See, for example, Lee et al. (1996) *Trends Biotechnol.* 14: 98-105 and Korz et al. (1995) *J Biotechnology* 39:59-65. Maximum specific growth rate is also sometimes referred to as unlimited growth.

In one method, oxygen limitation is quantified by oxygen concentration in the medium and is expressed in terms of dissolved oxygen concentration (DOC). The DOC in the culture medium can be less than about 20%, less than about 15%, less than about 10%, and less than about 5%. In other embodiments the DOC is about 0% or below the level of detection.

However, because oxygen is consumed by the cells relatively rapidly, a DOC of zero can mean that the cells are being cultured under anaerobic conditions (no oxygen) or that the cells are consuming oxygen as fast as it is being supplied. In another method, the cells' use of oxygen is expressed in terms of oxygen uptake rate (OUR; the cells' rate of oxygen consumption per liter of medium) to differentiate between these two possibilities. Suitable oxygen uptake rates include less than about 50 mmoles, less than about 40 mmoles, less than about 30 mmoles, less than about 20 mmoles per liter of medium, or less than about 10 mmoles per liter of medium.

Alternatively, specific oxygen uptake rate (SOUR which is OUR divided by cell density) can be used when normalized values with respect to cell densities is preferred. The amount of microorganism per liter of fermentation, or the density of microorganism, can be measured by measuring the weight of microorganism isolated from a given volume of the fermentation medium. A common measure is the dry weight of cells per liter of fermentation medium. Another method which can be used to monitor the fermentation while it is progressing is by a measurement of the optical density of the medium. A common method is to measure the optical density at a wavelength of 600 nm, referred to the $OD_{600}$, or the OD. The OD can be correlated to a the density of a specific type of organism within a specific medium, but the specific relationship between OD and amount of microorganism per volume will not generally be applicable across all types of organisms in all types of media. A calibration curve can be created by measuring the OD and the dry cell weight over a range of cell densities. In some cases, these correlations can be used in different fermentation of the same or similar microorganisms in the same or similar media. Suitable specific oxygen uptake rates include less than about 30 mmoles, less than about 25 mmoles, less than about 20 mmoles, less than about 15 mmoles, less than about 10 mmoles, or less than about 5 mmoles per gram of dry cell weight per hour.

We have also found that the host cells provided herein are able to tolerate some period of phosphate limitation and still make high levels of isoprenoid compounds. Without being bound by theory, cell growth under phosphate limited conditions appears to allow more of the carbon to be directed to product instead of biomass. Suitable concentrations of phosphate in the medium is less than about 5 grams, less than about 4 grams, less than about 3 grams, less than about 2 grams, or less than about 1 gram per liter of medium. In certain embodiments, the phosphate concentration is zero or below the level of detection. The periods of such phosphate limitation include at least 4 hours, at least 6 hours, at least 8 hours, at least 10 hours, at least 12 hours, at least 24 hours, or at least 48 hours.

Host cells can be grown under non-limiting conditions (allowing for maximum specific growth) to build sufficient biomass before limiting conditions (oxygen limited, phosphate limited, or both) are imposed. These limiting conditions include those such that specific growth is less than about 90%, 80%, 75%, 60%, 50%, 40%, 30%, 25%, 20%, 10%, 5%, or 1%, of the maximum specific growth rate.

Although specific embodiments are provided herein, the foregoing description is intended to illustrate and not limit the scope of the embodiments. Other aspects, advantages, and modifications within the scope of the embodiments will be apparent to those skilled in the art.

EXAMPLES

Unless otherwise indicated, conventional techniques of the biosynthetic industry and the like, which are within the skill of the art, may be used to practice the embodiments provided herein. To the extent such techniques are not described fully herein, one can find ample reference to them in the scientific literature.

In the following examples, efforts have been made to ensure accuracy with respect to numbers used (for example, amounts, temperature, and so on), but variation and deviation can be accommodated, and in the event a clerical error in the numbers reported herein exists, one of ordinary skill in the art can deduce the correct amount in view of the remaining disclosure herein. Unless indicated otherwise, temperature is reported in degrees Celsius, and pressure is at or near atmospheric pressure at sea level. All reagents, unless otherwise indicated, were obtained commercially. The following examples are intended for illustrative purposes only and do not limit in any way the scope of the embodiments provided herein.

Example 1

This example describes methods for making vectors for the targeted integration of nucleic acids encoding enzymes including enzymes of the MEV pathway into specific chromosomal locations of *Saccharomyces cerevisiae*.

Genomic DNA was isolated from *Saccharomyces cerevisiae* strains Y002 and Y003 (CEN.PK2 background MATA or MATα ura3-52 trp1-289 leu2-3,112 his3Δ1 MAL2-8C SUC2) (van Dijken et al. (2000) *Enzyme Microb. Technol.* 26:706-714), Y007 (S288C background MATA trp1Δ63) (ATCC number 200873), and EG123 (MATA ura3 trp1 leu2 his4 can1) (Michaelis & Herskowitz. (1988) *Mol. Cell Biol.* 8: 1309-1318). The strains were grown overnight in liquid medium containing 1% Yeast extract, 2% Bacto-peptone, and 2% Dextrose (YPD medium). Cells were isolated from 10 mL liquid cultures by centrifugation at 3,100 rpm, washing of cell pellets in 10 mL ultra-pure water, and re-centrifugation. Genomic DNA was extracted using the Y-DER yeast DNA extraction kit (Pierce Biotechnologies, Rockford, Ill.) as per manufacturer's suggested protocol. Extracted genomic DNA was re-suspended in 100 uL 10 mM Tris-Cl, pH 8.5, and $OD_{260/280}$ readings were taken on a ND-1000 spectrophotometer (NanoDrop Technologies, Wilmington, Del.) to determine genomic DNA concentration and purity.

DNA amplification by Polymerase Chain Reaction (PCR) was done in an Applied Biosystems 2720 Thermocycler (Applied Biosystems Inc., Foster City, Calif.) using the Phusion High Fidelity DNA Polymerase system (Finnzymes OY, Espoo, Finland) as per manufacturer's suggested protocol. Upon completion of a PCR amplification of a DNA fragment that was to be inserted into the TOPO TA pCR2.1 cloning vector (Invitrogen, Carlsbad, Calif.), A nucleotide overhangs were created by adding 1 uL of Qiagen Taq Polymerase (Qiagen, Valencia, Calif.) to the reaction mixture and performing an additional 10 minute, 72° C. PCR extension step, followed by cooling to 4° C. Upon completion of a PCR amplification, 8 uL of a 50% glycerol solution was added to the reaction mix.

Agarose gel electrophoresis was performed using a 1% TBE (0.89 M Tris, 0.89 M boric acid, 0.02 M EDTA sodium salt) agarose gel containing 0.5 ug/mL ethidium bromide, at 120 V, 400 mA for 30 minutes. DNA bands were visualized using ultraviolet light. DNA bands were excised from the gel with a sterile razor blade, and the excised DNA was gel purified using the Zymoclean Gel DNA Recovery Kit (Zymo Research, Orange, Calif.) according to manufacturer's suggested protocols. The purified DNA was eluted into 10 uL ultra-pure water, and $OD_{260/280}$ readings were taken on a ND-1000 spectrophotometer to determine DNA concentration and purity.

Ligations were performed using 100-500 ug of purified PCR product and High Concentration T4 DNA Ligase (New England Biolabs, Ipswich, Mass.) as per manufacturer's suggested protocol. For plasmid propagation, ligated constructs were transformed into *Escherichia coli* DH5α chemically competent cells (Invitrogen, Carlsbad, Calif.) as per manufacturer's suggested protocol. Positive transformants were selected on solid media containing 1.5% Bacto Agar, 1% Tryptone, 0.5% Yeast Extract, 1% NaCl, and an appropriate antibiotic. Isolated transformants were grown for 16 hours in liquid Luria-Bertoni (LB) medium containing appropriate antibiotics at 37° C., and plasmid was isolated and purified using a QIAprep Spin Miniprep kit (Qiagen, Valencia, Calif.) as per manufacturer's suggested protocol. Constructs were verified by performing diagnostic restriction enzyme digestions, resolving DNA fragments on an agarose gel, and visualizing the bands using ultraviolet light. Select constructs were also verified by DNA sequencing, which was done by Elim Biopharmaceuticals Inc. (Hayward, Calif.).

Figure 4A:
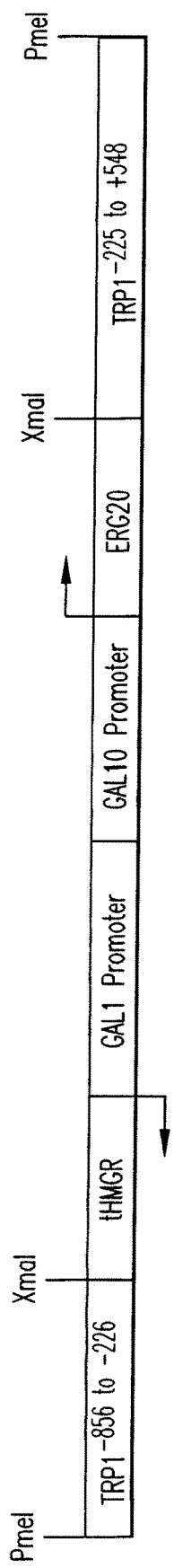
FIG. 4 shows maps of DNA fragments ERG20-PGAL-tHMGR (A), ERG13-PGAL-tHMGR (B), IDI1-PGAL-tHMGR (C), ERG10-PGAL-ERG12 (D), ERG8-PGAL-ERG19 (E), GAL74 to 1021-HPH-GAL11637 to 2587 (F), GAL80-50 to −1-NatR-GAL801309 to 1358 (G), and GAL11 to 48-NatR-GAL11500 to 1550 (H).

Plasmid pAM489 was generated by inserting the ERG20-$P_{GAL}$-tHMGR insert of vector pAM471 into vector pAM466. Vector pAM471 was generated by inserting DNA fragment ERG20-$P_{GAL}$-tHMGR, which comprises the open reading frame (ORF) of the ERG20 gene of *Saccharomyces cerevisiae* (ERG20 nucleotide positions 1 to 1208; A of ATG start codon is nucleotide 1) (ERG20), the genomic locus containing the divergent GAL1 and GAL10 promoter of *Saccharomyces cerevisiae* (GAL1 nucleotide position −1 to −668) ($P_{GAL}$), and a truncated ORF of the HMG1 gene of *Saccharomyces cerevisiae* (HMG1 nucleotide positions 1586 to 3323) (tHMGR), into the TOPO Zero Blunt II cloning vector (Invitrogen, Carlsbad, Calif.). Vector pAM466 was generated by inserting DNA fragment TRP1$^{-856\ to\ +548}$, which comprises a segment of the wild-type TRP1 locus of *Saccharomyces cerevisiae* that extends from nucleotide position −856 to position 548 and harbors a non-native internal XmaI restriction site between bases −226 and −225, into the TOPO TA pCR2.1 cloning vector (Invitrogen, Carlsbad, Calif.). DNA fragments ERG20-$P_{GAL}$-tHMGR and TRP1$^{-856\ to\ +548}$ were generated by PCR amplification as outlined in Table 1. For the construction of pAM489, 400 ng of pAM471 and 100 ng of pAM466 were digested to completion using XmaI restriction enzyme (New England Biolabs, Ipswich, Mass.), DNA fragments corresponding to the ERG20-$P_{GAL}$-tHMGR insert and the linearized pAM466 vector were gel purified, and 4 molar equivalents of the purified insert was ligated with 1 molar equivalent of the purified linearized vector, yielding pAM489. FIG. 4A shows a map of the ERG20-$P_{GAL}$-tHMGR insert, and SEQ ID NO: 1 shows the nucleotide sequence of the insert with flanking TRP1 sequences.

TABLE 1

PCR amplifications performed to generate pAM489

| PCR Round | Template | Primer 1 | Primer 2 | PCR Product |
|---|---|---|---|---|
| 1 | 100 ng of Y003 genomic DNA | 61-67-CPK001-G (SEQ ID NO: 12) | 61-67-CPK002-G (SEQ ID NO: 13) | TRP1$^{-856\ to\ -226}$ |
| | | 61-67-CPK003-G (SEQ ID NO: 14) | 61-67-CPK004-G (SEQ ID NO: 15) | TRP1$^{-225\text{-}to\ +548}$ |
| | 100 ng of EG123 genomic DNA | 61-67-CPK025-G (SEQ ID NO: 36) | 61-67-CPK050-G (SEQ ID NO: 44) | ERG20 |
| | 100 ng of Y002 genomic DNA | 61-67-CPK051-G (SEQ ID NO: 45) | 61-67-CPK052-G (SEQ ID NO: 46) | $P_{GAL}$ |
| | | 61-67-CPK053-G (SEQ ID NO: 47) | 61-67-CPK031-G (SEQ ID NO: 37) | tHMGR |
| 2 | 100 ng each of TRP1$^{-856\ to\ -226}$ and TRP1$^{-225\text{-}to\ +548}$ purified PCR products | 61-67-CPK001-G (SEQ ID NO: 12) | 61-67-CPK004-G (SEQ ID NO: 15) | TRP1$^{-856\ to\ +548}$ |
| | 100 ng each of ERG20 and $P_{GAL}$ purified PCR products | 61-67-CPK025-G (SEQ ID NO: 36) | 61-67-CPK052-G (SEQ ID NO: 46) | ERG20-$P_{GAL}$ |
| 3 | 100 ng each of ERG20-$P_{GAL}$ and tHMGR purified PCR products | 61-67-CPK025-G (SEQ ID NO: 36) | 61-67-CPK031-G (SEQ ID NO: 37) | ERG20-$P_{GAL}$-tHMGR |

Figure 4B:
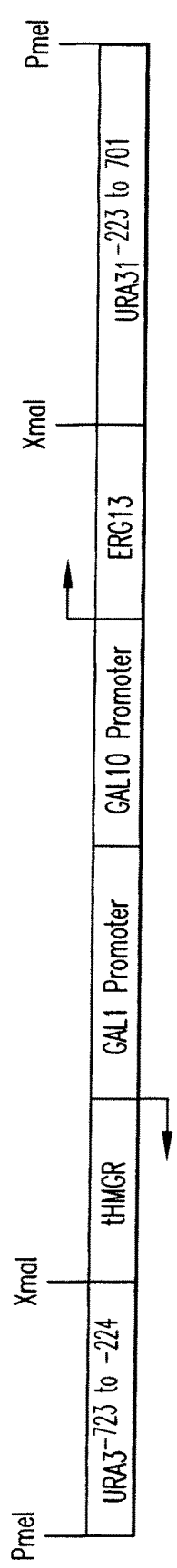

Plasmid pAM491 was generated by inserting the ERG13-$P_{GAL}$-tHMGR insert of vector pAM472 into vector pAM467. Vector pAM472 was generated by inserting DNA fragment ERG13-$P_{GAL}$-tHMGR, which comprises the ORF of the ERG13 gene of *Saccharomyces cerevisiae* (ERG13 nucleotide positions 1 to 1626) (ERG13), the genomic locus containing the divergent GAL1 and GAL10 promoter of *Saccharomyces cerevisiae* (GAL1 nucleotide position −1 to −668) ($P_{GAL}$), and a truncated ORF of the HMG1 gene of *Saccharomyces cerevisiae* (HMG1 nucleotide position 1586 to 3323) (tHMGR), into the TOPO Zero Blunt II cloning vector. Vector pAM467 was generated by inserting DNA fragment URA3$^{-723\ to\ 701}$, which comprises a segment of the wild-type URA3 locus of *Saccharomyces cerevisiae* that extends from nucleotide position −723 to position −224 and harbors a non-native internal XmaI restriction site between bases −224 and −223, into the TOPO TA pCR2.1 cloning vector. DNA fragments ERG13-$P_{GAL}$-tHMGR and URA3$^{-723\ to\ 701}$ were generated by PCR amplification as outlined in Table 2. For the construction of pAM491, 400 ng of pAM472 and 100 ng of pAM467 were digested to completion using XmaI restriction enzyme, DNA fragments corresponding to the ERG13-$P_{GAL}$-tHMGR insert and the linearized pAM467 vector were gel purified, and 4 molar equivalents of the purified insert was ligated with 1 molar equivalent of the purified linearized vector, yielding pAM491. FIG. 4B shows a map of the ERG13-$P_{GAL}$-tHMGR insert, and SEQ ID NO: 2 shows the nucleotide sequence of the insert with flanking URA3 sequences.

TABLE 2

PCR amplifications performed to generate pAM491

| PCR Round | Template | Primer 1 | Primer 2 | PCR Product |
|---|---|---|---|---|
| 1 | 100 ng of Y007 genomic DNA | 61-67-CPK005-G (SEQ ID NO: 16) | 61-67-CPK006-G (SEQ ID NO: 17) | URA3$^{-723\ to\ -224}$ |
| | | 61-67-CPK007-G (SEQ ID NO: 18) | 61-67-CPK008-G (SEQ ID NO: 19) | URA3$^{-223\ to\ 701}$ |
| | 100 ng of Y002 genomic DNA | 61-67-CPK032-G (SEQ ID NO: 38) | 61-67-CPK054-G (SEQ ID NO: 48) | ERG13 |
| | | 61-67-CPK052-G (SEQ ID NO: 46) | 61-67-CPK055-G (SEQ ID NO: 49) | P$_{GAL}$ |
| | | 61-67-CPK031-G (SEQ ID NO: 37) | 61-67-CPK053-G (SEQ ID NO: 47) | tHMGR |
| 2 | 100 ng each of URA3$^{-723\ to\ -224}$ and URA3$^{-223\ to\ 701}$ purified PCR products | 61-67-CPK005-G (SEQ ID NO: 16) | 61-67-CPK008-G (SEQ ID NO: 19) | URA3$^{-723\ to\ 701}$ |
| | 100 ng each of ERG13 and P$_{GAL}$ purified PCR products | 61-67-CPK032-G (SEQ ID NO: 38) | 61-67-CPK052-G (SEQ ID NO: 46) | ERG13-P$_{GAL}$ |
| 3 | 100 ng each of ERG13-P$_{GAL}$ and tHMGR purified PCR products | 61-67-CPK031-G (SEQ ID NO: 37) | 61-67-CPK032-G (SEQ ID NO: 38) | ERG13-P$_{GAL}$-tHMGR |

Figure 4C:
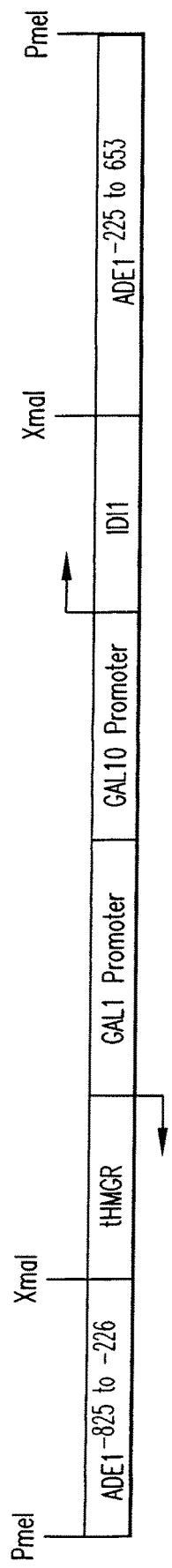

Plasmid pAM493 was generated by inserting the IDI1-P$_{GAL}$-tHMGR insert of vector pAM473 into vector pAM468. Vector pAM473 was generated by inserting DNA fragment IDI1-P$_{GAL}$-tHMGR, which comprises the ORF of the IDI1 gene of Saccharomyces cerevisiae (IDI1 nucleotide position 1 to 1017) (IDI1), the genomic locus containing the divergent GAL1 and GAL10 promoter of Saccharomyces cerevisiae (GAL1 nucleotide position −1 to −668) (P$_{GAL}$), and a truncated ORF of the HMG1 gene of Saccharomyces cerevisiae (HMG1 nucleotide positions 1586 to 3323) (tHMGR), into the TOPO Zero Blunt II cloning vector. Vector pAM468 was generated by inserting DNA fragment ADE1$^{-825\ to\ 653}$, which comprises a segment of the wild-type ADE1 locus of Saccharomyces cerevisiae that extends from nucleotide position −225 to position 653 and harbors a non-native internal XmaI restriction site between bases −226 and −225, into the TOPO TA pCR2.1 cloning vector. DNA fragments IDI1-P$_{GAL}$-tHMGR and ADE1$^{-825\ to\ 653}$ were generated by PCR amplification as outlined in Table 3. For the construction of pAM493, 400 ng of pAM473 and 100 ng of pAM468 were digested to completion using XmaI restriction enzyme, DNA fragments corresponding to the IDI1-P$_{GAL}$-tHMGR insert and the linearized pAM468 vector were gel purified, and 4 molar equivalents of the purified insert was ligated with 1 molar equivalent of the purified linearized vector, yielding vector pAM493. FIG. 4C shows a map of the IDI1-P$_{GAL}$-tHMGR insert, and SEQ ID NO: 3 shows the nucleotide sequence of the insert with flanking ADE1 sequences.

TABLE 3

PCR amplifications performed to generate pAM493

| PCR Round | Template | Primer 1 | Primer 2 | PCR Product |
|---|---|---|---|---|
| 1 | 100 ng of Y007 genomic DNA | 61-67-CPK009-G (SEQ ID NO: 20) | 61-67-CPK010-G (SEQ ID NO: 21) | ADE1$^{-825\ to\ -226}$ |
| | | 61-67-CPK011-G (SEQ ID NO: 22) | 61-67-CPK012-G (SEQ ID NO: 23) | ADE1$^{-225\ to\ 653}$ |
| | 100 ng of Y002 genomic DNA | 61-67-CPK047-G (SEQ ID NO: 43) | 61-67-CPK064-G (SEQ ID NO: 58) | IDI1 |
| | | 61-67-CPK052-G (SEQ ID NO: 46) | 61-67-CPK065-G (SEQ ID NO: 59) | P$_{GAL}$ |
| | | 61-67-CPK031-G (SEQ ID NO: 37) | 61-67-CPK053-G (SEQ ID NO: 47) | tHMGR |
| 2 | 100 ng each of ADE1$^{-825\ to\ -226}$ and ADE1$^{-225\ to\ 653}$ purified PCR products | 61-67-CPK009-G (SEQ ID NO: 20) | 61-67-CPK012-G (SEQ ID NO: 23) | ADE1$^{-825\ to\ 653}$ |
| | 100 ng each of IDI1 and P$_{GAL}$ purified PCR products | 61-67-CPK047-G (SEQ ID NO: 43) | 61-67-CPK052-G (SEQ ID NO: 46) | IDI1-P$_{GAL}$ |
| 3 | 100 ng each of IDI1-P$_{GAL}$ and tHMGR purified PCR products | 61-67-CPK031-G (SEQ ID NO: 37) | 61-67-CPK047-G (SEQ ID NO: 43) | IDI1-P$_{GAL}$-tHMGR |

Plasmid pAM495 was generated by inserting the ERG10-P$_{GAL}$-ERG12 insert of pAM474 into vector pAM469. Vector pAM474 was generated by inserting DNA fragment ERG10-P$_{GAL}$-ERG12, which comprises the ORF of the ERG10 gene of Saccharomyces cerevisiae (ERG10 nucleotide position 1 to 1347) (ERG10), the genomic locus containing the divergent GAL1 and GAL10 promoter of Saccharomyces cerevisiae (GAL1 nucleotide position −1 to −668) (P$_{GAL}$), and the ORF of the ERG12 gene of Saccharomyces cerevisiae (ERG12 nucleotide position 1 to 1482) (ERG12), into the TOPO Zero Blunt II cloning vector. Vector pAM469 was generated by inserting DNA fragment HIS3$^{-32\ to\ -1000}$-HISMX-HIS3$^{504\ to\ -1103}$, which comprises two segments of the HIS locus of Saccharomyces cerevisiae that extend from nucleotide position −32 to position −1000 and from nucleotide position 504 to position 1103, a HISMX marker, and a non-native XmaI restriction site between the HIS3$^{504\ to\ -1103}$ sequence and the HISMX marker, into the TOPO TA pCR2.1 cloning vector. DNA fragments ERG10-P$_{GAL}$-ERG12 and HIS3$^{-32\ to\ -1000}$-HISMX-HIS3$^{504\ to\ -1103}$ were generated by PCR amplification as outlined in Table 4. For construction of pAM495, 400 ng of pAM474 and 100 ng of pAM469 were digested to completion using XmaI restriction enzyme, DNA fragments corresponding to the ERG10-P$_{GAL}$-ERG12 insert and the linearized pAM469 vector were gel purified, and 4 molar equivalents of the purified insert was ligated with 1 molar equivalent of the purified linearized vector, yielding vector pAM495. FIG. 4D shows a map of the ERG10-P$_{GAL}$-ERG12 insert, and SEQ ID NO: 4 shows the nucleotide sequence of the insert with flanking HIS3 sequences.

of the ERG19 gene of *Saccharomyces cerevisiae* (ERG19 nucleotide position 1 to 1341) (ERG19), into the TOPO Zero Blunt II cloning vector. Vector pAM470 was generated by inserting DNA fragment LEU2$^{-100\ to\ 450}$-HISMX-LEU2$^{1096\ to\ 1770}$, which comprises two segments of the LEU2 locus of *Saccharomyces cerevisiae* that extend from nucleotide position −100 to position 450 and from nucleotide position 1096 to position 1770, a HISMX marker, and a non-native XmaI restriction site between the LEU2$^{1096\ to\ 1770}$ sequence and the HISMX marker, into the TOPO TA pCR2.1 cloning vector. DNA fragments ERG8-P$_{GAL}$-ERG19 and LEU2$^{-100\ to\ 450}$-HISMX-LEU2$^{1096\ to\ 1770}$ were generated by PCR amplification as outlined in Table 5. For the construction of pAM497, 400 ng of pAM475 and 100 ng of pAM470 were digested to completion using XmaI

TABLE 4

PCR reactions performed to generate pAM495

| PCR Round | Template | Primer 1 | Primer 2 | PCR Product |
|---|---|---|---|---|
| 1 | 100 ng of Y007 genomic DNA | 61-67-CPK013-G (SEQ ID NO: 24) | 61-67-CPK014alt-G (SEQ ID NO: 25) | HIS3$^{-32\ to\ -1000}$ |
| | | 61-67-CPK017-G (SEQ ID NO: 28) | 61-67-CPK018-G (SEQ ID NO: 29) | HIS3$^{504\ to\ -1103}$ |
| | | 61-67-CPK035-G (SEQ ID NO: 39) | 61-67-CPK056-G (SEQ ID NO: 50) | ERG10 |
| | | 61-67-CPK057-G (SEQ ID NO: 51) | 61-67-CPK058-G (SEQ ID NO: 52) | P$_{GAL}$ |
| | | 61-67-CPK040-G (SEQ ID NO: 40) | 61-67-CPK059-G (SEQ ID NO: 53) | ERG12 |
| | 10 ng of plasmid pAM330 DNA** | 61-67-CPK015alt-G (SEQ ID NO: 26) | 61-67-CPK016-G (SEQ ID NO: 27) | HISMX |
| 2 | 100 ng each of HIS3$^{504\ to\ -1103}$ and HISMX PCR purified products | 61-67-CPK015alt-G (SEQ ID NO: 26) | 61-67-CPK018-G (SEQ ID NO: 29) | HISMX-HIS3$^{504\ to\ -1103}$ |
| | 100 ng each of ERG10 and P$_{GAL}$ purified PCR products | 61-67-CPK035-G (SEQ ID NO: 39) | 61-67-CPK058-G (SEQ ID NO: 52) | ERG10-P$_{GAL}$ |
| 3 | 100 ng each of HIS3$^{-32\ to\ -1000}$ and HISMX-HIS3$^{504\ to\ -1103}$ purified PCR products | 61-67-CPK013-G (SEQ ID NO: 24) | 61-67-CPK018-G (SEQ ID NO: 29) | HIS3$^{-32\ to\ -1000}$-HISMX-HIS3$^{504\ to\ -1103}$ |
| | 100 ng each of ERG10-P$_{GAL}$ and ERG12 purified PCR products | 61-67-CPK035-G (SEQ ID NO: 39) | 61-67-CPK040-G (SEQ ID NO: 40) | ERG10-P$_{GAL}$-ERG12 |

**The HISMX marker in pAM330 originated from pFA6a-HISMX6-PGAL1 as described by van Dijken et al. ((2000) Enzyme Microb. Technol. 26(9-10): 706-714).

Plasmid pAM497 was generated by inserting the ERG8-P$_{GAL}$-ERG19 insert of pAM475 into vector pAM470. Vector pAM475 was generated by inserting DNA fragment ERG8-P$_{GAL}$-ERG19, which comprises the ORF of the ERG8 gene of *Saccharomyces cerevisiae* (ERG8 nucleotide position 1 to 1512) (ERG8), the genomic locus containing the divergent GAL1 and GAL10 promoter of *Saccharomyces cerevisiae* (GAL1 nucleotide position −1 to −668) (P$_{GAL}$), and the ORF restriction enzyme, DNA fragments corresponding to the ERG8-P$_{GAL}$-ERG19 insert and the linearized pAM470 vector were purified, and 4 molar equivalents of the purified insert was ligated with 1 molar equivalent of the purified linearized vector, yielding vector pAM497. FIG. 4E for a map of the ERG8-P$_{GAL}$-ERG19 insert, and SEQ ID NO: 5 shows the nucleotide sequence of the insert with flanking LEU2 sequences.

TABLE 5

PCR reactions performed to generate pAM497

| PCR Round | Template | Primer 1 | Primer 2 | PCR Product |
|---|---|---|---|---|
| 1 | 100 ng of Y007 genomic DNA | 61-67-CPK019-G (SEQ ID NO: 30) | 61-67-CPK020-G (SEQ ID NO: 31) | LEU2$^{-100\ to\ 450}$ |
| | | 61-67-CPK023-G (SEQ ID NO: 34) | 61-67-CPK024-G (SEQ ID NO: 35) | LEU2$^{1096\ to\ 1770}$ |
| | 10 ng of plasmid pAM330 DNA** | 61-67-CPK021-G (SEQ ID NO: 32) | 61-67-CPK022-G (SEQ ID NO: 33) | HISMX |

TABLE 5-continued

PCR reactions performed to generate pAM497

| PCR Round | Template | Primer 1 | Primer 2 | PCR Product |
|---|---|---|---|---|
| | 100 ng of Y002 genomic DNA | 61-67-CPK041-G (SEQ ID NO: 41) | 61-67-CPK060-G (SEQ ID NO: 54) | ERG8 |
| | | 61-67-CPK061-G (SEQ ID NO: 55) | 61-67-CPK062-G (SEQ ID NO: 56) | $P_{GAL}$ |
| | | 61-67-CPK046-G (SEQ ID NO: 42) | 61-67-CPK063-G (SEQ ID NO: 57) | ERG19 |
| 2 | 100 ng each of $LEU2^{1096\ to\ 1770}$ and HISMX purified PCR products | 61-67-CPK021-G (SEQ ID NO: 32) | 61-67-CPK024-G (SEQ ID NO: 35) | HISMX-$LEU2^{1096\ to\ 1770}$ |
| | 100 ng each of ERG8 and $P_{GAL}$ purified PCR products | 61-67-CPK041-G (SEQ ID NO: 41) | 61-67-CPK062-G (SEQ ID NO: 56) | ERG8-$P_{GAL}$ |
| 3 | 100 ng of $LEU2^{-100\ to\ 450}$ and HISMX-$LEU2^{1096\ to\ 1770}$ purified PCR products | 61-67-CPK019-G (SEQ ID NO: 30) | 61-67-CPK024-G (SEQ ID NO: 35) | $LEU2^{-100\ to\ 450}$-HISMX-$LEU2^{1096\ to\ 1770}$ |
| | 100 ng each of ERG8-$P_{GAL}$ and ERG19 purified PCR products | 61-67-CPK041-G (SEQ ID NO: 41) | 61-67-CPK046-G (SEQ ID NO: 42) | ERG8-$P_{GAL}$-ERG19 |

**The HISMX marker in pAM330 originated from pFA6a-HISMX6-PGAL1 as described by van Dijken et al. ((2000) Enzyme Microb. Technol. 26(9-10): 706-714).

Example 2

This example describes methods for making plasmids and DNA fragments useful in the embodiments provided herein.

Plasmid pAM584 was generated by inserting DNA fragment $GAL7^{4\ to\ 1021}$-HPH-$GAL1^{1637\ to\ 2587}$ into the TOPO ZERO Blunt II cloning vector (Invitrogen, Carlsbad, Calif.). DNA fragment $GAL7^{4\ to\ 1021}$-HPH-$GAL1^{1637\ to\ 2587}$ comprises a segment of the ORF of the GAL7 gene of Saccharomyces cerevisiae (GAL7 nucleotide positions 4 to 1021) ($GAL7^{4\ to\ 1021}$), the hygromycin resistance cassette (HPH), and a segment of the 3' untranslated region (UTR) of the GAL1 gene of Saccharomyces cerevisiae (GAL1 nucleotide positions 1637 to 2587). The DNA fragment was generated by PCR amplification as outlined in Table 6. FIG. 4F shows a map and SEQ ID NO: 9 the nucleotide sequence of DNA fragment $GAL7^{4\ to\ 1021}$-HPH-$GAL1^{1637\ to\ 2587}$.

DNA fragment $GAL80^{-50\ to\ -1}$-NatR-$GAL80^{1309\ to\ 1358}$ was generated by PCR amplification. The DNA fragments includes the nourseothricin resistance selectable marker gene of Streptomyces noursei (NatR) flanked by two segments of 50 nucleotides each that map immediately upstream and immediately downstream of the coding region of the GAL80 gene of Saccharomyces cerevisiae (GAL80 nucleotide position −50 to −1 and 1309 to 1358; $GAL80^{-50\ to\ -1}$ and $GAL80^{1309\ to\ 1358}$, respectively). FIG. 4G shows a map, and SEQ ID NO: 8 the nucleotide sequence, of DNA fragment $GAL80^{-50\ to\ -1}$-NatR-$GAL80^{1309\ to\ 1358}$.

DNA fragment $GAL1^{1\ to\ 48}$-NatR-$GAL1^{1500\ to\ 1550}$ was generated by PCR amplification. The DNA fragment includes the nourseothricin resistance selectable marker gene of Streptomyces noursei (NatR) flanked by two segments of 40 to 50 nucleotides each that map to the 5' and the 3' end of the coding region of the GAL1 gene of Saccharomyces cerevisiae (GAL1 nucleotide position 1 to 48 and 1500 to 1550; $GAL1^{1\ to\ 48}$ and $GAL1^{1500\ to\ 1550}$, respectively). FIG. 4H shows a map, and SEQ ID NO: 68 the nucleotide sequence of DNA fragment $GAL1^{1\ to\ 48}$-NatR-$GAL1^{1500\ to\ 1550}$.

TABLE 6

PCR reactions performed to generate pAM584

| PCR Round | Template | Primer 1 | Primer 2 | PCR Product |
|---|---|---|---|---|
| 1 | 100 ng of Y002 genomic DNA | 91-014-CPK236-G (SEQ ID NO: 65) | 91-014-CPK237-G (SEQ ID NO: 66) | $GAL7^{4\ to\ 1021}$ |
| | | 91-014-CPK232-G (SEQ ID NO: 63) | 91-014-CPK233-G (SEQ ID NO: 64) | $GAL1^{1637\ to\ 2587}$ |
| | 10 ng of plasmid pAM547 DNA** | 91-014-CPK231-G (SEQ ID NO: 62) | 91-014-CPK238-G (SEQ ID NO: 67) | HPH |
| 2 | 100 ng each of $GAL7^{4\ to\ 1021}$ and HPH purified PCR products | 91-014-CPK231-G (SEQ ID NO: 62) | 91-014-CPK236-G (SEQ ID NO: 65) | $GAL7^{4\ to\ 1021}$-HPH |
| 3 | 100 ng of each $GAL1^{1637\ to\ 2587}$ and $GAL7^{4\ to\ 1021}$-HPH purified PCR products | 91-014-CPK233-G (SEQ ID NO: 64) | 91-014-CPK236-G (SEQ ID NO: 65) | $GAL7^{4\ to\ 1021}$-HPH-$GAL1^{1637\ to\ 2587}$ |

**Plasmid pAM547 was generated synthetically, and comprises the HPH cassette, which consists of the coding sequence for the hygromycin B phosphotransferase of Escherichia coli flanked by the promoter and terminator of the Tef1 gene of Kluyveromyces lactis.

Expression plasmid pAM353 was generated by inserting a nucleotide sequence encoding a β-farnesene synthase into the pRS425-Gal1 vector (Mumberg et. al. (1994) Nucl. Acids. Res. 22(25): 5767-5768). The nucleotide sequence insert was generated synthetically, using as a template the coding sequence of the β-farnesene synthase gene of *Artemisia annua* (GenBank accession number AY835398) codon-optimized for expression in *Saccharomyces cerevisiae* (SEQ ID NO: 10). The synthetically generated nucleotide sequence was flanked by 5' BamHI and 3' XhoI restriction sites, and could thus be cloned into compatible restriction sites of a cloning vector such as a standard pUC or pACYC origin vector. The synthetically generated nucleotide sequence was isolated by digesting to completion the DNA synthesis construct using BamHI and XhoI restriction enzymes. The reaction mixture was resolved by gel electrophoresis, the approximately 1.7 kb DNA fragment comprising the β-farnesene synthase coding sequence was gel extracted, and the isolated DNA fragment was ligated into the BamHI XhoI restriction site of the pRS425-Gal1 vector, yielding expression plasmid pAM353.

Figure 5:
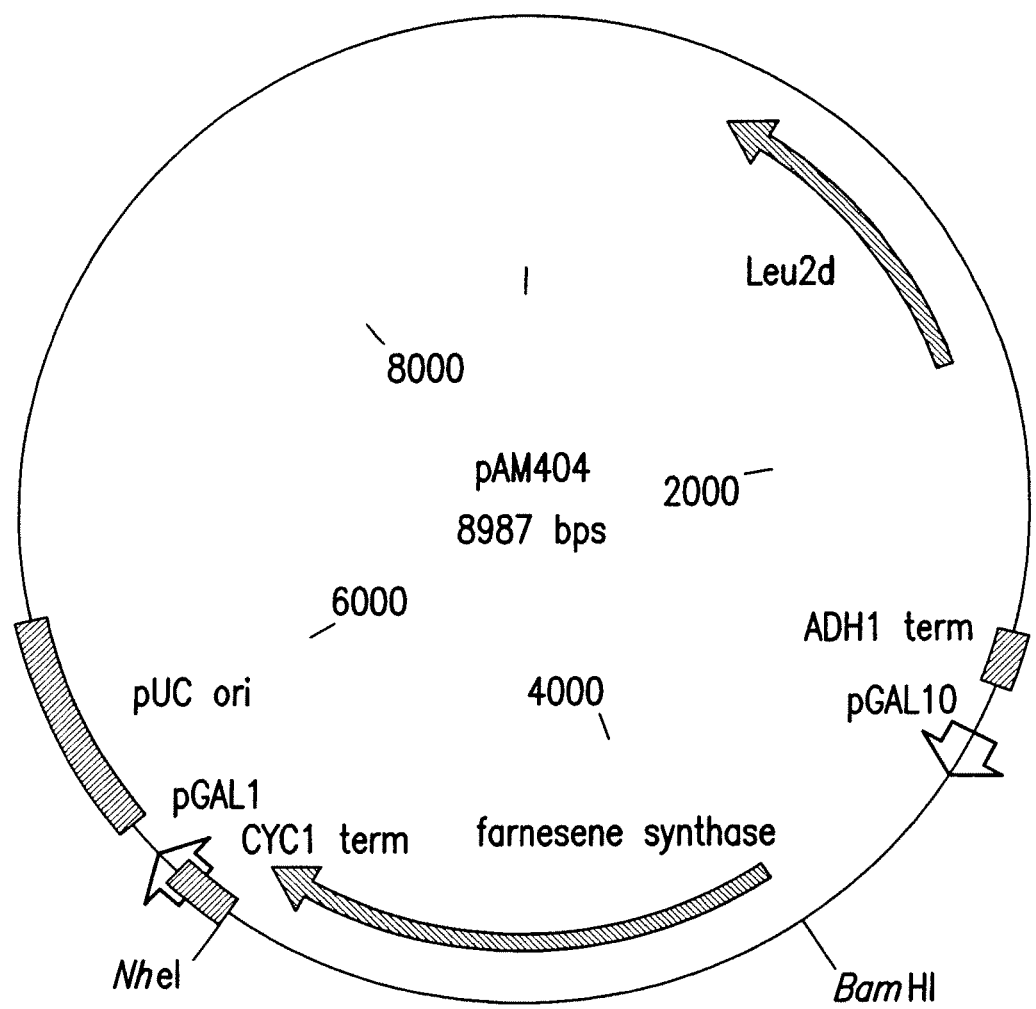
FIG. 5 shows a map of plasmid pAM404.

Expression plasmid pAM404 was generated by inserting a nucleotide sequence encoding the β-farnesene synthase of *Artemisia annua*, codon-optimized for expression in *Saccharomyces cerevisiae*, into vector pAM178 (SEQ ID NO: 69). The nucleotide sequence encoding the β-farnesene synthase was PCR amplified from pAM353 using primers 52-84 pAM326 BamHI (SEQ ID NO: 71) and 52-84 pAM326 NheI (SEQ ID NO: 72). The resulting PCR product was digested to completion using BamHI and NheI restriction enzymes, the reaction mixture was resolved by gel electrophoresis, the approximately 1.7 kb DNA fragment comprising the β-farnesene synthase coding sequence was gel extracted, and the isolated DNA fragment was ligated into the BamHI NheI restriction site of vector pAM178, yielding expression plasmid pAM404 (see FIG. 5 for a plasmid map).

Example 3

This example describes the generation of *Saccharomyces cerevisiae* strains useful in the embodiments provided herein.

*Saccharomyces cerevisiae* strains CEN.PK2-1C Y002 and Y003 (MATA or MATalpha; ura3-52; trp1-289; leu2-3,112; his3Δ1; MAL2-8C; SUC2) (van Dijken et al. (2000) *Enzyme Microb. Technol.* 26(9-10):706-714) were prepared for introduction of inducible MEV pathway genes by replacing the ERG9 promoter with the *Saccharomyces cerevisiae* MET3 promoter, and the ADE1 ORF with the *Candida glabrata* LEU2 gene (CgLEU2). This was done by PCR amplifying the KanMX-$P_{MET3}$ region of vector pAM328 (SEQ ID NO: 6), which comprises the $P_{MET3}$ promoter preceded by the kanamycin resistance marker flanked by the promoter and terminator of the Tef1 gene of *Kluyveromyces lactis*, using primers 50-56-pw100-G (SEQ ID NO: 10) and 50-56-pw101-G (SEQ ID NO: 11), which include 45 base pairs of homology to the native ERG9 promoter, transforming 10 ug of the resulting PCR product into exponentially growing Y002 and Y003 cells using 40% w/w Polyethelene Glycol 3350 (Sigma-Aldrich, St. Louis, Mo.), 100 mM Lithium Acetate (Sigma-Aldrich, St. Louis, Mo.), and 10 ug Salmon Sperm DNA (Invitrogen Corp., Carlsbad, Calif.), and incubating the cells at 30° C. for 30 minutes followed by heat shocking them at 42° C. for 30 minutes (Schiestl and Gietz (1989) *Curr. Genet.* 16:339-346). Positive recombinants were identified by their ability to grow on rich medium containing 0.5 ug/mL Geneticin (Invitrogen Corp., Carlsbad, Calif.), and selected colonies were confirmed by diagnostic PCR. The resultant clones were given the designation Y93 (MAT A) and Y94 (MAT alpha). The 3.5 kb CgLEU2 genomic locus was then amplified from *Candida glabrata* genomic DNA (ATCC, Manassas, Va.) using primers 61-67-CPK066-G (SEQ ID NO: 60) and 61-67-CPK067-G (SEQ ID NO: 61), which contain 50 base pairs of flanking homology to the ADE1 ORF, and 10 ug of the resulting PCR product were transformed into exponentially growing Y93 and Y94 cells, positive recombinants were selected for growth in the absence of leucine supplementation, and selected clones were confirmed by diagnostic PCR. The resultant clones were given the designation Y176 (MAT A) and Y177 (MAT alpha).

Strain Y188 was generated by digesting pAM491 and pAM495 plasmid DNA to completion using PmeI restriction enzyme (New England Biolabs, Beverly, Mass.), and introducing the purified DNA inserts into exponentially growing Y176 cells. Positive recombinants were selected for by growth on medium lacking uracil and histidine, and integration into the correct genomic locus was confirmed by diagnostic PCR.

Strain Y189 was generated by digesting pAM489 and pAM497 plasmid DNA to completion using PmeI restriction enzyme, and introducing the purified DNA inserts into exponentially growing Y177 cells. Positive recombinants were selected for by growth on medium lacking tryptophan and histidine, and integration into the correct genomic locus was confirmed by diagnostic PCR.

Approximately $1 \times 10^7$ cells from strains Y188 and Y189 were mixed on a YPD medium plate for 6 hours at room temperature to allow for mating. The mixed cell culture was plated to medium lacking histidine, uracil, and tryptophan to select for growth of diploid cells. Strain Y238 was generated by transforming the diploid cells using pAM493 plasmid DNA that had been digested to completion using PmeI restriction enzyme, and introducing the purified DNA insert into the exponentially growing diploid cells. Positive recombinants were selected for by growth on medium lacking adenine, and integration into the correct genomic locus was confirmed by diagnostic PCR.

Haploid strain Y211 (MAT alpha) was generated by sporulating strain Y238 in 2% potassium acetate and 0.02% Raffinose liquid medium, isolating approximately 200 genetic tetrads using a Singer Instruments MSM300 series micromanipulator (Singer Instrument LTD, Somerset, UK), identifying independent genetic isolates containing the appropriate complement of introduced genetic material by their ability to grow in the absence of adenine, histidine, uracil, and tryptophan, and confirming the integration of all introduced DNA by diagnostic PCR.

Strain Y227 was generated from strain Y211 by rendering the strain capable of converting FPP to amorpha-4,1,1-diene. To this end, exponentially growing Y211 cells were transformed with expression plasmid pAM426 (SEQ ID NO: 7), which comprises a GAL1 promoter operably linked to the coding sequence of an amorpha-4,11-diene synthase gene that is codon-optimized for expression in *Saccharomyces cerevisiae* (Merke et al. (2000) *Ach. Biochem. Biophys.* 381:173-180). Host cell transformants were selected on complete synthetic defined media lacking leucine.

Strain Y293 was generated from strain Y227 by deleting the coding sequence of the GAL80 gene, and thus rendering the GAL promoters in the strain constitutively active. To this end, exponentially growing Y227 cells were transformed with DNA fragment GAL80$^{-50\ to\ -1}$-NatR-GAL80$^{1309\ to\ 1358}$. Host cell transformants were selected on YPD agar containing 100 μg/mL nourseothricin, single colonies were picked, and integration into the correct genomic locus was confirmed by diagnostic PCR.

Strain Y337 was generated from strain Y227 by rendering the strain unable to catabolize galactose. To this end, pAM584 plasmid DNA was digested to completion using PmeI restriction enzyme, and the purified DNA insert GAL7$^{4\ to\ 1021}$-HPH-GAL1$^{1637\ to\ 2587}$ was introduced into exponentially growing Y227 cells. Positive recombinants were selected for by growth on YPD agar containing hygromycin B (Sigma, St. Louis, Mo.). Integration into the correct genomic locus was confirmed by diagnostic PCR and by testing the strain for inability to use galactose as a carbon source.

Strain Y351 was generated from strain Y211 by rendering the strain unable to catabolize galactose. To this end, pAM584 plasmid DNA was digested to completion using PmeI restriction enzyme, and the purified DNA insert GAL7$^{4\ to\ 1021}$-HPH-GAL1$^{1637\ to\ 2587}$ was introduced into exponentially growing Y211. Host cell transformants were selected on YPD agar containing hygromycin B. Integration into the correct genomic locus was confirmed by diagnostic PCR and by testing the strain for inability to use galactose as a carbon source.

Strain Y352 was generated from strain Y351 by rendering the strain able to produce β-farnesene synthase. To this end, exponentially growing Y351 cells were transformed with expression plasmid pAM404. Host cell transformants were selected on complete synthetic defined media lacking leucine.

Strain Y283 was generated from strain Y227 by deleting the coding sequence of the GAL1 gene and thus rendering the strain unable to catabolize galactose. To this end, exponentially growing Y227 cells were transformed with DNA fragment GAL1$^{1\ to\ 48}$-NatR-GAL1$^{1500\ to\ 1550}$. Host cell transformants were selected on YPD agar containing 100 μg/mL nourseothricin, single colonies were picked, and integration into the correct genomic locus was confirmed by diagnostic PCR and by growing the strain on agar containing glycerol and 2-deoxygalactose (a functional GAL1p would convert the latter into a toxin).

Strain Y221 was generated from strain Y211 by transforming exponentially growing Y211 cells with vector pAM178 (SEQ ID NO: 69). Positive transformants were selected for by growth on complete synthetic medium lacking leucine.

Strain Y290 was generated from strain Y221 by deleting the coding sequence of the GAL80 gene, and thus rendering the GAL promoters in the strain constitutively active.

Strain Y318 was generated from strain Y290 by screening colonies for loss of the pAM178 vector.

Strain 409 was generated from strain Y318 by rendering the strain able to produce β-farnesene synthase in the presence of galactose. To this end, exponentially growing Y318 cells were transformed with expression plasmid pAM404. Host cell transformants were selected on complete synthetic defined media lacking leucine.

Strain Y419 was generated from strain Y409 by rendering the GAL promoters in the strain constitutively active and able to express higher levels of GAL4p in the presence of glucose (i.e., able to more efficiently drive expression off galactose-inducible promoters in the presence of glucose, as well as assure that there is enough Gal4p transcription factor to drive expression from all the galactose-inducible promoters in the cell). To this end, the KanMX marker at the ERG9 locus in strain Y409 was replaced by a DNA fragment that comprised the ORF of the GAL4 gene of *Saccharomyces cerevisiae* under the control of an "operative constitutive" version of its native promoter (Griggs & Johnston (1991) *PNAS* 88(19):8597-8601) and the GAL4 terminator ($P_{Gal4OC}$-GAL4-$T_{GAL4}$), and the nourseothricin resistance selectable marker gene of *Streptomyces noursei* (NatR) flanked by the promoter and terminator of the Tef1 gene of *Kluyveromyces lactis*.

Strain Y677 was generated from strain Y419 by introducing another copy of the coding region of mevalonate kinase under the control of $P_{GAL1}$ at the GAL80 locus.

Cell banks of strains Y293, Y283, Y352 and Y677 were prepared by growing the cells in seed medium at 30° C. until they reached an OD$_{600}$ of between 2 to 5. At that time, the flasks were placed on ice. Three parts culture and 2 parts ice cold sterile 50% glycerol were combined, and 1 mL aliquots of this mixture were frozen at −80° C. in cyrovials. The same procedure was used for strain Y337, however the OD$_{600}$ for that strain was 13.6 at the time it was frozen.

Example 4

This example describes the production of amorpha-4,11-diene by host cells in fed batch, carbon-restricted fermentation with a glucose only feed.

Y337 seed cultures were prepared by inoculating a 1 mL frozen vial into a 250 mL flask containing 50 mL seed medium (Table 7). After ~24 hours of growth at 30° C., 0.5 mL of the culture was sub-cultured into additional 250 mL flasks each containing 50 mL seed medium. The seed cultures were grown at 30° C. overnight to an OD$_{600}$ of approximately 3 to 12. Flasks were pooled and used to inoculate bioreactors containing batch medium (Table 8) at 10% v/v.

TABLE 7

Seed medium

| Component | Seed Medium |
|---|---|
| tap water (mL/L) | 350 |
| 2x batch base (mL/L)$^{a)}$ | 500 |
| 715 g/L glucose monohydrate (mL/L)$^{b)}$ | 30 |
| Yeast vitamin solution (mL/L) (Table 9) | 12 |
| Yeast trace metals solution (mL/L) (Table 9) | 10 |
| succinate (0.5 M, pH 5.0) (mL/L)$^{c)}$ | 100 |

$^{a)}$16 g/L KH$_2$PO$_4$, 30 g/L (NH$_4$)$_2$SO$_4$, and 12.3 g/L MgSO$_4$*7H$_2$O (Note: no heating while mixing these components)
$^{b)}$The glucose monohydrate stock solution was prepared by dissolving the sugar in water with heating, allowing the solution to cool, and filter sterilizing.
$^{c)}$The succinate stock solution was prepared by dissolving succinic acid in water with heating, letting the solution cool, adjusting the pH to 5.05 with NaOH, and sterilizing the solution by autoclaving (45 minutes at 121° C.).

TABLE 8

Bioreactor batch medium

| Component | Batch Medium |
|---|---|
| tap water (mL/L) | 350 |
| 2x batch base (mL/L) (Table 7) | 500 |
| glucose (g/L) | 19.5 |
| Yeast vitamin solution (mL/L) (Table 9) | 12 |
| Yeast trace metals solution (mL/L) (Table 9) | 10 |

Batch medium was prepared by combining 2x batch base with tap water in a 2L bioreactor, autoclaving the unit, and in a sterile hood bringing the volume of the solution to 90% of final by adding concentrated filter-sterilized stock solutions of sugar, vitamins, and trace metals. The remaining 10% of starting volume was from the seed culture.

TABLE 9

Vitamin and trace metals stock solutions

| Component | Yeast vitamin solution (g/L)[a] | Component | Yeast trace metals solution (g/L)[b] |
|---|---|---|---|
| Biotin | 0.05 | $ZnSO_4 \cdot 7H_2O$ | 5.75 |
| calcium pantothenate | 1 | $MnCl_2 \cdot 4H_2O$ | 0.32 |
| nicotinic acid | 1 | $CuSO_4$ anhydrous | 0.32 |
| Myoinositol | 25 | $CoCl_2 \cdot 6H_2O$ | 0.47 |
| thiamine HCl | 1 | $Na_2MoO_4 \cdot 2H_2O$ | 0.48 |
| pyridoxol HCl | 1 | $CaCl_2 \cdot 2H_2O$ | 2.9 |
| p-aminobenzoic acid | 0.2 | $FeSO_4 \cdot 7H_2O$ | 2.8 |
|  |  | 0.5 M EDTA | 80 (mL/L) |

[a] Biotin was first dissolved in 10 mL of 5 M NaOH, and then added to DI water (750 mL/L). The pH was adjusted to 6.5 using 5 M NaOH or HCl, and again adjusted after the addition of each vitamin. After all vitamins were dissolved, the solution was brought to final volume with DI water, and filter sterilized. The bottle was covered in aluminum foil and stored at 4° C.

[b] EDTA was first added to DI water (750 mL/L) before the $ZnSO_4$ was dissolved. The pH was adjusted to 6.0 using 5 M NaOH, and again adjusted after the addition of each metal. After all metals were dissolved, the pH was adjusted to 4.0 using 5 M HCl, and the solution was brought to the final volume with DI water, and filter sterilized. The bottle was covered in aluminum foil and stored at 4° C.

The pH of the fermentation was controlled automatically and maintained at pH 5 with the addition of 10 N $NH_4OH$. Temperature was maintained at 30° C. Airflow was supplied at a rate of 1 LPM. Dissolved oxygen was maintained at 40% with an agitation cascade followed by oxygen enrichment. Foam was controlled with Biospumex antifoam 200 K.

The bioreactor culture was allowed to grow until glucose in the batch medium was depleted, at which point, an exponential glucose feed was initiated for which glucose feed medium (Table 10) was pumped into the bioreactor at the rate defined by the following equations:

$$F = V \mu_{set} S_B e^{\mu_{set}(t-t0)}$$

$$V = V_0 + V_{feed}$$

F is the substrate mass flow rate (g/hr), V is the liquid volume in the bioreactor at a given time (L), $S_B$ is the concentration of substrate in the batch media (20 g/L), $\mu_{set}$ is the specific feed rate (0.087 $hr^{-1}$), t is the batch age (hr), $t_0$ is the batch age when the feed was initiated (hr), $V_0$ is the initial volume in the bioreactor, and $V_{feed}$ is the total volume of feed added to the bioreactor at a given time (L). The exponential feed phase continued until the ratio of F/V reached a preset maximum feed rate (Table 11). After reaching this maximum, the ratio of F/V was maintained constant for the remainder of the process at a preset stationary feed rate (Table 11).

TABLE 10

| Component | Glucose Feed Medium[a] | Mixed Feed Medium[b] |
|---|---|---|
| Base Medium | | |
| glucose monohydrate (g/L)[a] | 650 | 425 |
| $KH_2PO_4$ (g/L) | 9 | 9 |
| $MgSO_4 \cdot 7H_2O$ (g/L) | 5.12 | 5.12 |
| $K_2SO_4$ (g/L) | 3.5 | 3.5 |
| $Na_2SO_4$ (g/L) | 0.28 | 0.28 |

TABLE 10-continued

| Component | Glucose Feed Medium[a] | Mixed Feed Medium[b] |
|---|---|---|
| Supplmentary Components | | |
| Yeast vitamin solution (mL/L) (Table 9) | 12 | 12 |
| Yeast trace metals solution (mL/L) (Table 9) | 10 | 10 |
| 95% (v/v) ethanol (mL/L) | 0 | 237 |

[a] Glucose feed medium was prepared by mixing glucose monohydrate, $KH_2PO_4$, $MgSO_4 \cdot 7H_2O$, $K_2SO_4$, and $Na_2SO_4$ in 38° C. tap water, cooling the solution, filter sterilizing, adding the supplementary components (concentrated filter-sterilized stock solutions of trace metals and vitamins) in a sterile hood, and bringing the solution to final volume by adding sterile water.

[b] Mixed feed medium was prepared by mixing glucose, $KH_2PO_4$, $MgSO_4 \cdot 7H_2O$, $K_2SO_4$, and $Na_2SO_4$ in 300 mL of 38° C. tap water, heating the mixture to approximately 100° C. to fully dissolve the sugar and salts, adding water to bring the volume to 750 mL, cooling the solution, filter sterilizing using a 0.2 micron filter, adding first 237 mL of 95% (v/v) ethanol and adding the supplementary components (concentrated filter-sterilized stock solutions of trace metals and vitamins) in a sterile hood, and bringing the solution to the final volume of 1 L by adding sterile water.

Production of amorpha-4,11-diene was induced at an $OD_{600}$ of 50 about 24 hours after inoculation with the addition of 10 g/L galactose to the bioreactor and feed bottle (22.2 mL of a 450 g/L galactose stock solution per liter culture volume). In addition, 0.25 g/L methionine was added to the bioreactor and 1 g/L methionine was added to the feed bottle to repress transcription of the ERG9 gene (10 mL of a 25 g/L methionine stock solution per liter culture volume and 40 mL of a 25 g/L methionine stock solution per liter feed volume), and 10% v/v of autoclaved methyl oleate was added to the bioreactor to capture the amorpha-4,11-diene. (The 450 g/L galactose stock solution was prepared by dissolving the sugar in water with heating, allowing the solution to cool, and filter sterilizing. The 25 g/L methionine stock solution was prepared by dissolving methionine in water, and filter sterilizing the solution.)

Samples were taken at various time points and diluted at a ratio of 1:20 into methanol. Each diluted sample was vortexed for 30 minutes, and culture debris was spun down. Amorpha-4,11-diene titers were determined by transferring 5 to 10 uL of the supernatant to a clean glass vial containing 990 to 995 uL ethyl acetate spiked with trans-caryophyllene as an internal standard. The ethyl acetate samples were analyzed on an Agilent 7890N gas chromatograph equipped with a flame ionization detector (Agilent Technologies Inc., Palo Alto, Calif.). Compounds in a 1 uL aliquot of each sample were separated using a DB Wax column (Agilent Technologies, Inc., Palo Alto, Calif.), helium carrier gas, and the following temperature program: 220° C. hold for 3 minutes, increasing temperature at 100° C./minute to a temperature of 260° C. Using this protocol, amorpha-4,11-diene has a retention time of approximately 3.4 minutes. Amporpha-4,11-diene titers were calculated by comparing generated peak areas against a quantitative calibration curve of purified amorpha-4,11-diene in trans-caryophyllene-spiked ethyl acetate.

Figure 6:
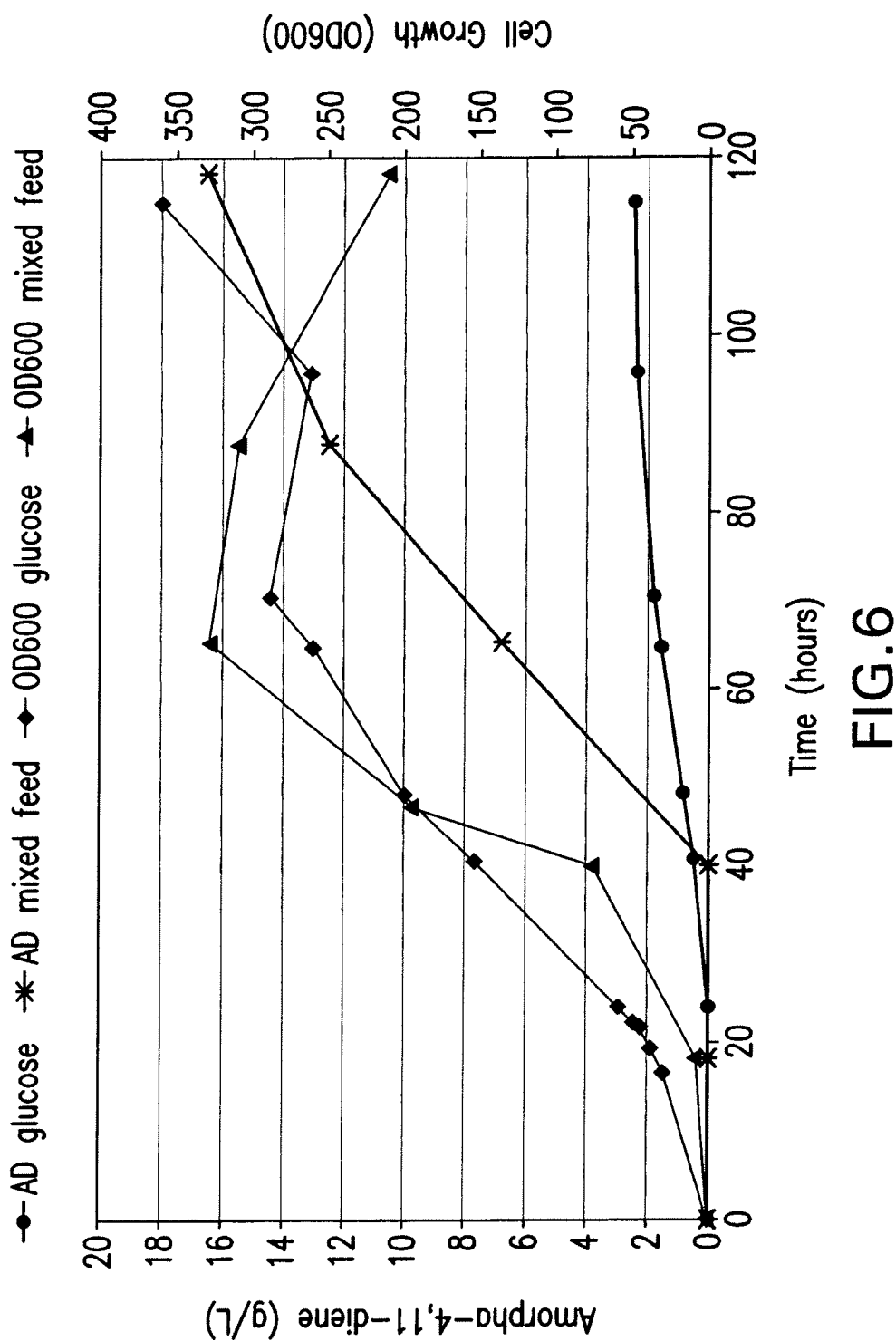
FIG. 6 shows cell growth and amorpha-4,11-diene (AD) production by strain Y337 under carbon restriction using either a glucose feed or a glucose/ethanol mixed feed.

As shown in Table 11 and FIG. 6, strain Y337 produced 2.4 g/L amorpha-4,11-diene (AD) at 114 hours after the start of the fermentation in the glucose only feed process.

TABLE 11

Amorpha-4,11-diene production by strain Y337 using either a glucose feed or a glucose/ethanol mixed feed

| Glucose in Feed Medium (g/L) | Ethanol in Feed Medium (g/L) | Maximum Feed Rate (g/hr/L)[a] | Stationary Feed Rate (g/hr/L)[a] | Maximum AD Titer (g/L) | Yield at Maximum Titer (mg product/g substrate) |
|---|---|---|---|---|---|
| 545 | 0 | 10 | 10 | 2.4 | 5.4 |
| 340 | 180 | 8.6 | 8.6 | 16.5 | 38.7 |
| 340 | 180 | 8.6 | 4.3 | 12.6 | 50.3 |

[a]g/hr/L is g substrate/hr/L bioreactor volume.

Example 5

This example describes the production of amorpha-4,11-diene by host cells in fed batch, carbon-restricted fermentation with a glucose-ethanol mixed feed.

Y337 seed cultures were prepared and used to inoculate bioreactors as described in Example 4. Fermentations were carried out, and samples were analyzed, essentially as described in Example 4 with the following modifications.

During the early phase of the fermentation, some of the glucose in the batch medium was converted to ethanol. The bioreactor culture was allowed to grow until the glucose and the ethanol in the batch medium was depleted, at which point an exponential feed was initiated for which mixed feed medium (Table 10) was pumped into the bioreactor at the rate defined by the following equations:

$$F = V \mu_{set} S_B e^{\mu_{set}(t-t_0)}$$

$$V = V_0 + V_{feed}$$

F is the substrate mass flow rate (g/hr), V is the liquid volume in the bioreactor at a given time (L), $S_B$ is the concentration of substrate in the batch media (20 g/L), $\mu_{set}$ is the specific feed rate (0.087 hr$^{-1}$), t is the batch age (hr), $t_0$ is the batch age when the feed was initiated (hr), $V_0$ is the initial volume in the bioreactor, and $V_{feed}$ is the total volume of feed added to the bioreactor at a given time (L). The exponential feed phase continued until the ratio of F/V reached a preset maximum feed rate in units of g substrate/hr/L bioreactor volume (Table 11). After reaching this maximum, the ratio of F/V was maintained constant for the remainder of the process at a preset stationary feed rate (Table 11).

Production of amorpha-4,11-diene was induced at an $OD_{600}$ of 77 about 40 hours after inoculation.

As shown in Table 11 and FIG. 6, strain Y337 produced up to 16.5 g/L amorpha-4,11-diene at 118 hours after the start of the fermentation in the mixed glucose and ethanol feed fermentation.

Example 6

This example describes the production of amorpha-4,11-diene by host cells in fed-batch, pulse feed fermentation with an ethanol only feed.

Y293 seed cultures were prepared and used to inoculate bioreactors as described in Example 3. Fermentations were carried out, and samples were analyzed, essentially as described in Example 4 with the following modifications.

Figure 7A:
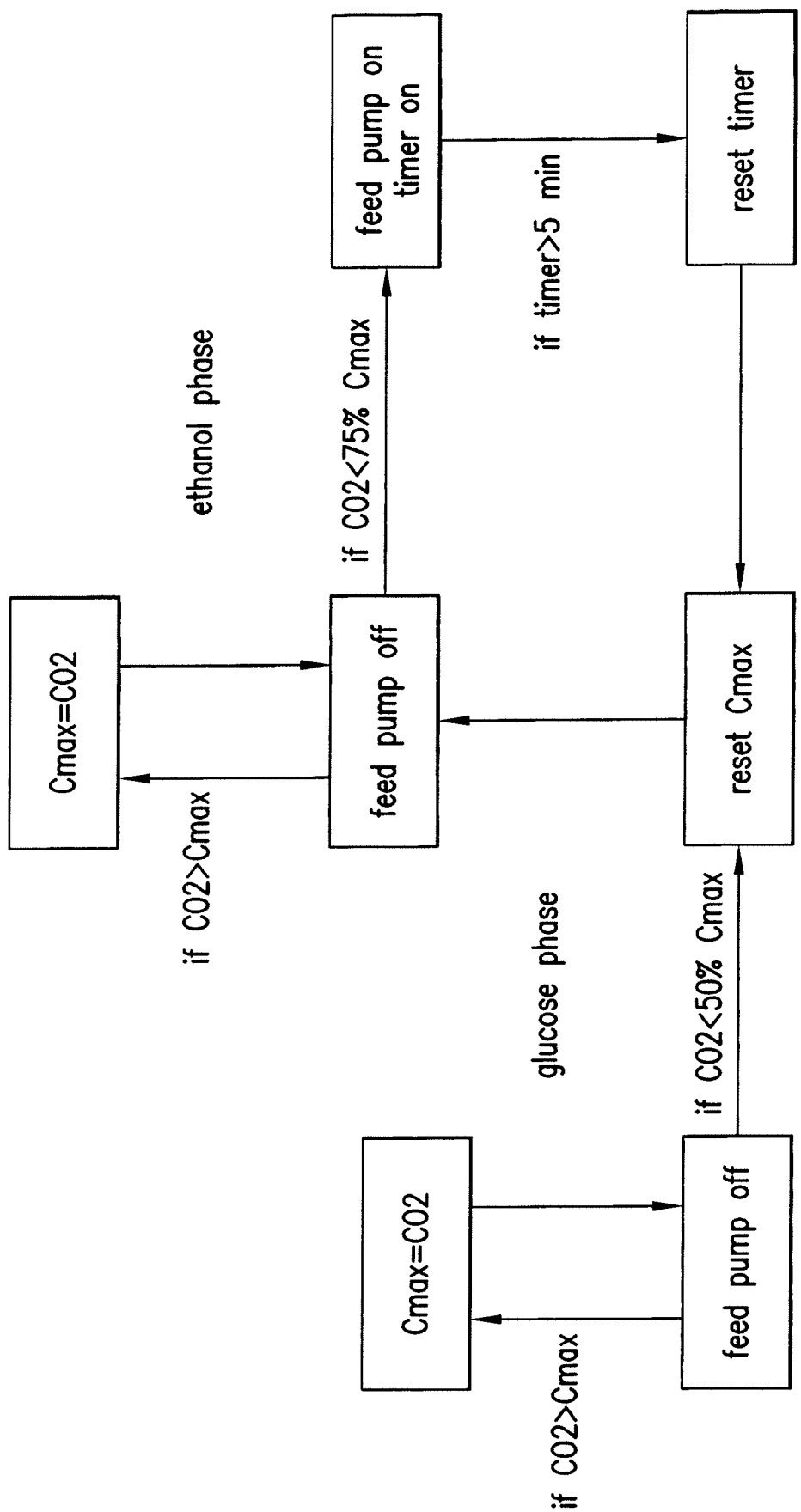
FIG. 7A shows a diagram of a CO2 control feed algorithm.
Figure 7B:
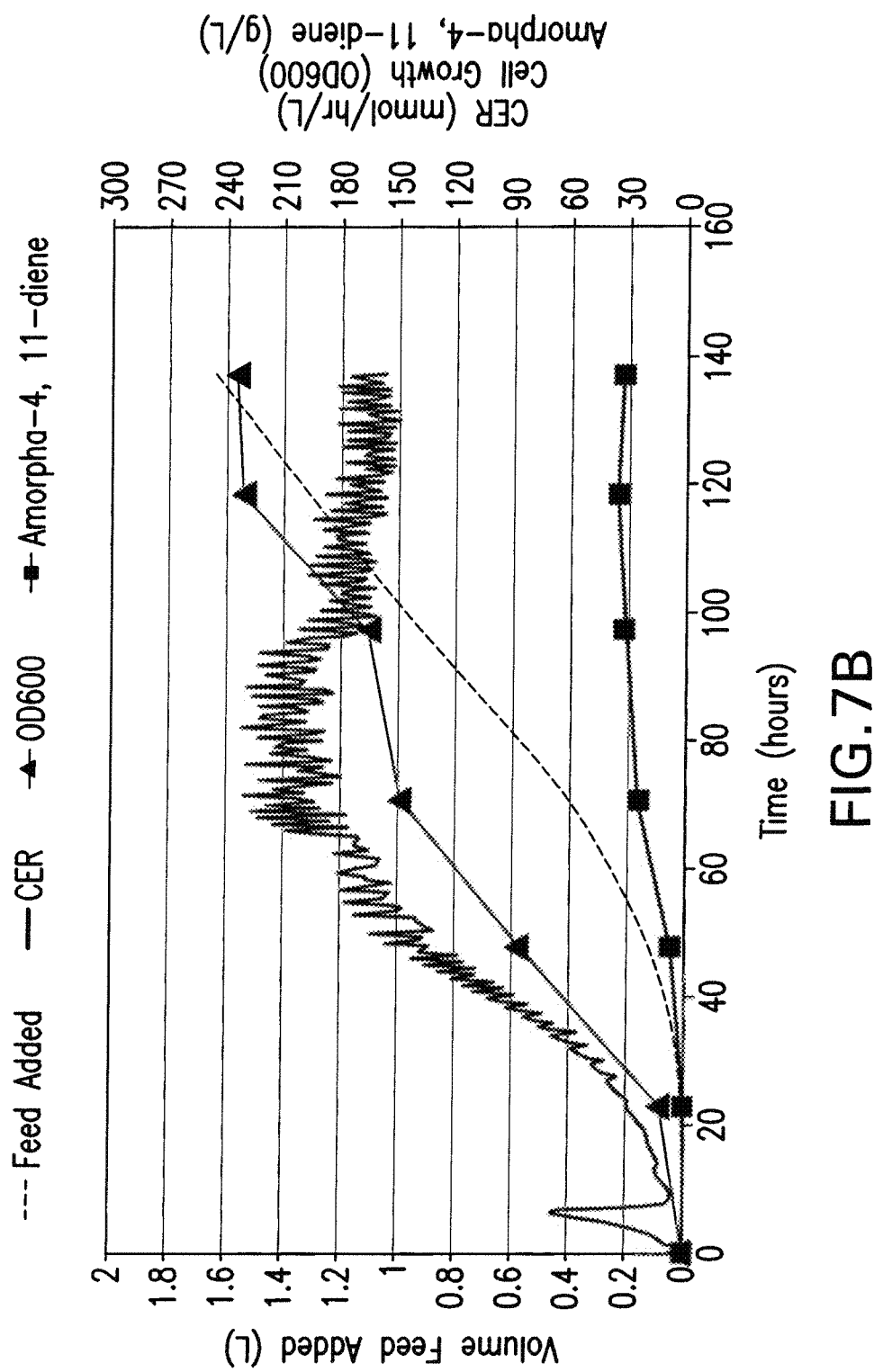
FIG. 7B shows carbon dioxide evolution rate, substrate delivery, growth, and production of amorpha-4,11-diene by strain Y293 using an ethanol pulse feed.

During the early phase of the fermentation, some of the glucose in the batch medium was converted to ethanol. The bioreactor culture was allowed to grow until the glucose and the ethanol in the batch medium was depleted, at which point an ethanol pulse feed was initiated. The rate of the feed was controlled by the percent of $CO_2$ in the off-gas (the $CO_2$ evolution rate; CER), which was monitored with an off-gas analyzer and a computer algorithm that assigned a variable ($C_{max}$) to the maximum CER which tracked the maximum value of $CO_2$ percent in off gas. While growing on glucose, the CER evolved rapidly (FIG. 7B). When glucose was depleted from the batch medium, the CER dropped to below 50% of $C_{max}$, and the computer algorithm reset $C_{max}$ to the $CO_2$ value after the drop. When the ethanol produced from the excess glucose in the batch medium was depleted, the CER dropped a second time. The pulse feed was triggered automatically when the CER fell below 75% of the current $C_{max}$. The pump injected 75% (v/v) ethanol into the bioreactor for 5 minutes, delivering approximately 10 g ethanol to the culture. $C_{max}$ was reset to the value of the percent $CO_2$ in the off-gas at the time the pump was turned off and then reassign to track the increases in $CO_2$ evolution, and the pump was reactivated when the CER again fell below 75% of the newly set $C_{max}$. The feed algorithm was iterated throughout the fermentation (FIG. 7A), and ensured that the culture was not overfed with ethanol. Because none of the salts, trace metals, vitamins, sugars, or amino acid solutions were soluble in the ethanol feed, concentrated feed components (Table 12) were combined and injected through a septum in the bioreactor head plate once per day according to how much ethanol volume had been delivered since the previous addition of feed components.

TABLE 12

| Concentrated feed components | |
|---|---|
| Component | Amount (mL/L ethanol) |
| glucose (450 g/L) | 24 |
| methionine (25 g/L) | 40 |
| 10x feed base[a] | 100 |
| Yeast vitamin solution (mL/L) (Table 9) | 12 |
| Yeast trace metals solution (Table 9) | 10 |

[a]90 g/L $KH_2PO_4$, 51.2 g/L $MgSO_4$*$7H_2O$, 35 g/L $K_2SO_4$, and 2.8 g/L $Na_2SO_4$ Ten hours after the glucose was depleted from the batch medium, 0.25 g/L methionine was added to the bioreactor through the head plate, and 10% v/v of autoclaved methyl oleate was pumped into the vessel. (Since strain Y293 comprises a disrupted GAL80 gene, galactose was not necessary to induce production of amorpha-4,11-diene.)

As shown in FIG. 7B, strain Y293 produced 36 g/L amorpha-4,11-diene.

Example 7

This example describes the production of amorpha-4,11-diene by host cells in fed batch, carbon-restricted fermentation with an ethanol only feed.

Y293 seed cultures were prepared and used to inoculate bioreactors containing batch medium (Table 13) as described in Example 3.

TABLE 13

Bioreactor media

| Component | Batch Medium |
|---|---|
| glucose-H$_2$O (715 g/L) (mL/L) | 19.5 |
| (NH$_4$)$_2$SO$_4$ (g/L) | 15 |
| KH$_2$PO$_4$ (g/L) | 26 |
| MgSO$_4$*7H2O (g/L) | 16.4 |
| K$_2$SO$_4$ (g/L) | 7 |
| Na$_2$SO$_4$ (g/L) | 0.56 |
| Yeast vitamin solution (mL/L) (Table 9) | 46.3 |
| Yeast trace metals solution (mL/L) (Table 9) | 38.5 |

Fermentations were carried out, and samples were analyzed, essentially as described in Example 4 with the following modifications:

The bioreactor culture was allowed to grow until glucose in the batch medium was depleted, at which point an exponential feed was initiated for which glucose feed medium (Table 10) was pumped into the bioreactor at the rate defined by the following equations:

$$F = V\mu_{set}S_B e^{\mu_{set}(t-t0)}$$

$$V = V_0 + V_{feed}$$

F is the substrate mass flow rate (g/hr), V is the liquid volume in the fermentor at a given time (L), $S_B$ is the concentration of substrate in the batch media (20 g/L), $\mu_{set}$ is the specific feed rate (0.087 hr$^{-1}$), t is the batch age (hr), to is the batch age when the feed was initiated (hr), $V_0$ is the initial volume in the fermentor, and $V_{feed}$ is the total volume of feed added to the fermentor at a given time (L). The exponential feed continued until the maximum feed rate of 7.1 g/hr/L was reached (OD$_{600}$ of approximately 50). At that point, the feed was switched to an ethanol feed (190 proof), and the feed rate was set to a constant volumetric value of 2.5 g/hr/L for the remainder of the fermentation. With this programmed feed rate, ethanol consumption rates were controlled, and ranged from 0.4 to 1.75 g ethanol/g DCW/day.

Figure 8:
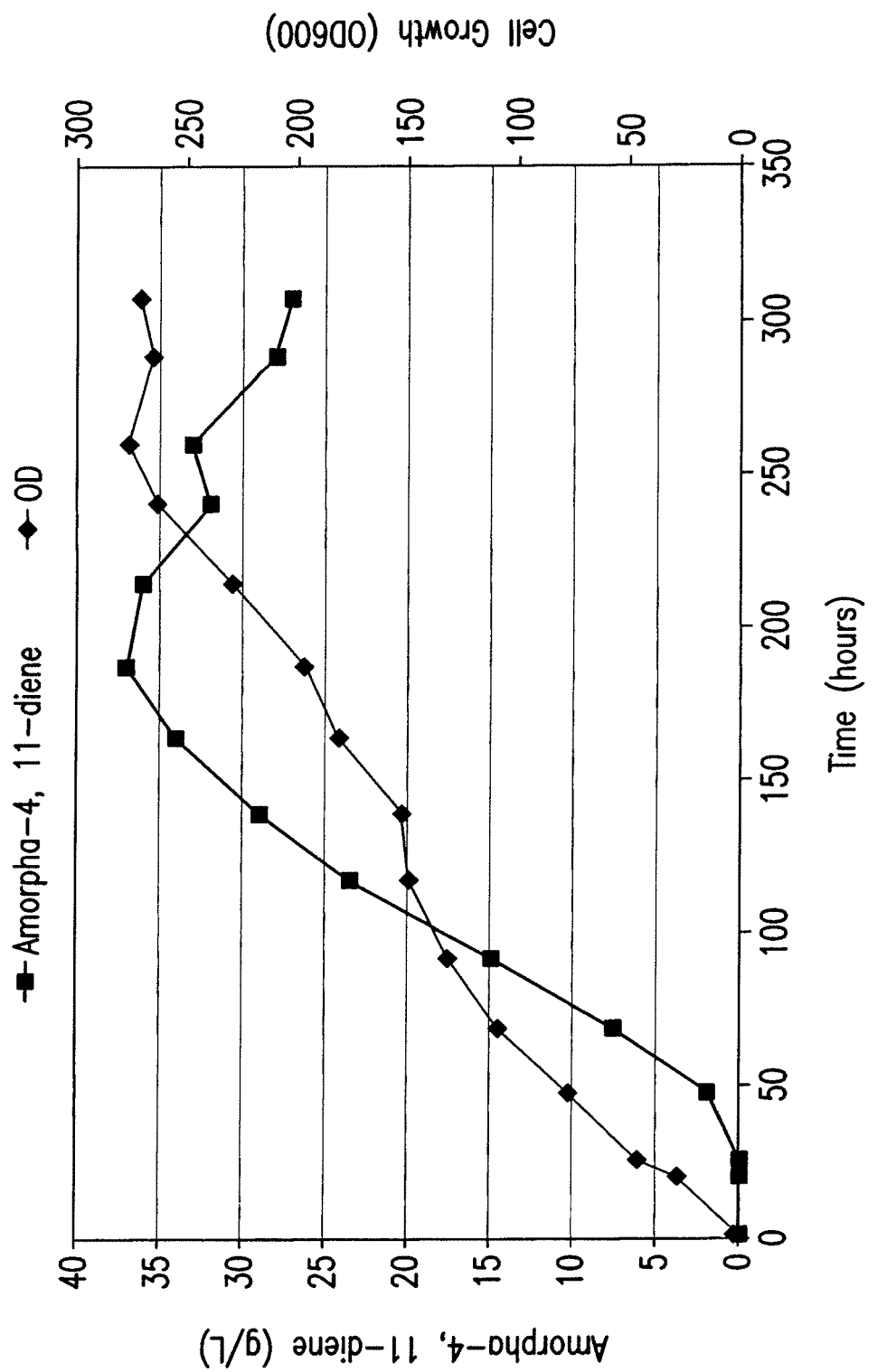
FIG. 8 shows cell growth and amorpha-4,11-diene production by strain Y293 under carbon restriction using a concentrated glucose feed for initial growth followed by an ethanol feed for production.

As shown in FIG. 8, strain Y293 produced 37 g/L amorpha-4,11-diene at 187 hours after the start of fermentation.

Example 8

This example describes the production of farnesene by host cells in fed batch, carbon-restricted fermentation with an ethanol only feed.

Y677 seed cultures were prepared and used to inoculate two bioreactors each containing 630 mL batch medium (Table 14) as described in Example 3. To one of the two bioreactors, 200 mL methyl oleate was added for product capture. Fermentations were carried out, and samples were analyzed, essentially as described in Example 4 with the following modifications:

TABLE 14

Bioreactor media

| Component | Batch Medium |
|---|---|
| Glucose (g/L) | 39.03 |
| (NH$_4$)$_2$SO$_4$ (g/L) | 15 |
| KH$_2$PO$_4$ (g/L) | 33.7 |
| MgSO$_4$*7H2O (g/L) | 20.77 |
| K$_2$SO$_4$ (g/L) | 10 |
| Na$_2$SO$_4$ (g/L) | 0.8 |
| Yeast vitamin solution (mL/L) (Table 9) | 32.4 |
| Yeast trace metals solution (mL/L) (Table 9) | 27 |

During the early phase of the fermentations, some of the glucose in the batch medium was converted to ethanol. The bioreactor cultures were allowed to grow until the glucose and the ethanol in the batch media were depleted, at which point, an exponential feed was initiated for which pure ethanol (190 proof) was pumped into the bioreactor at the rate defined by the following equations:

$$F = V\mu_{set}S_B e^{\mu_{set}(t-t0)}$$

$$V = V_0 + V_{feed}$$

Figure 9A:
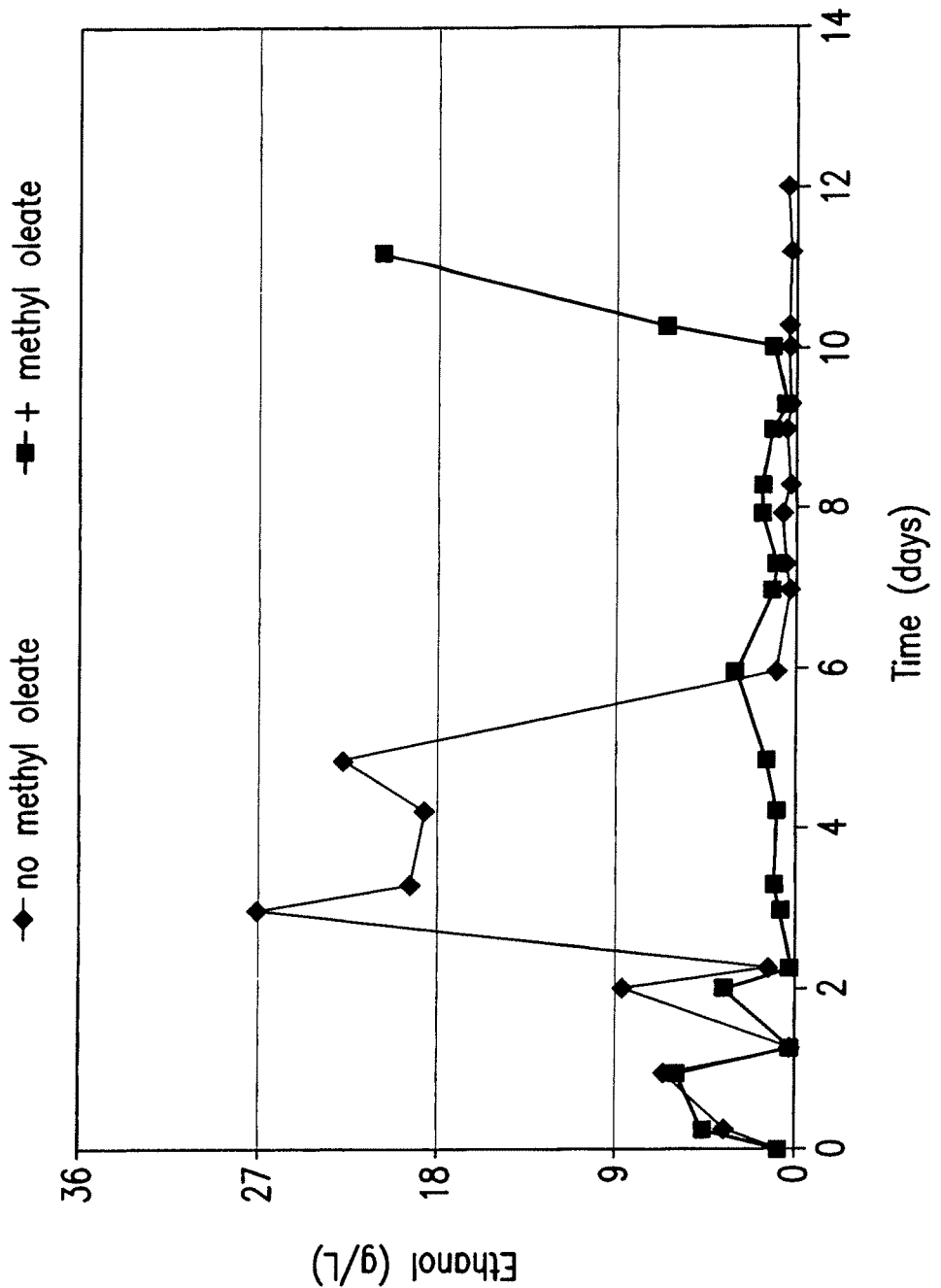
FIGS. 9A through 9E show ethanol production/consumption, feed rate, growth, carbon evolution and oxygen utilization rates, and farnesene production by strain Y677 in fed batch, carbon-restricted fermentation with an ethanol only feed in the presence or absence of methyl oleate.
Figure 9B:
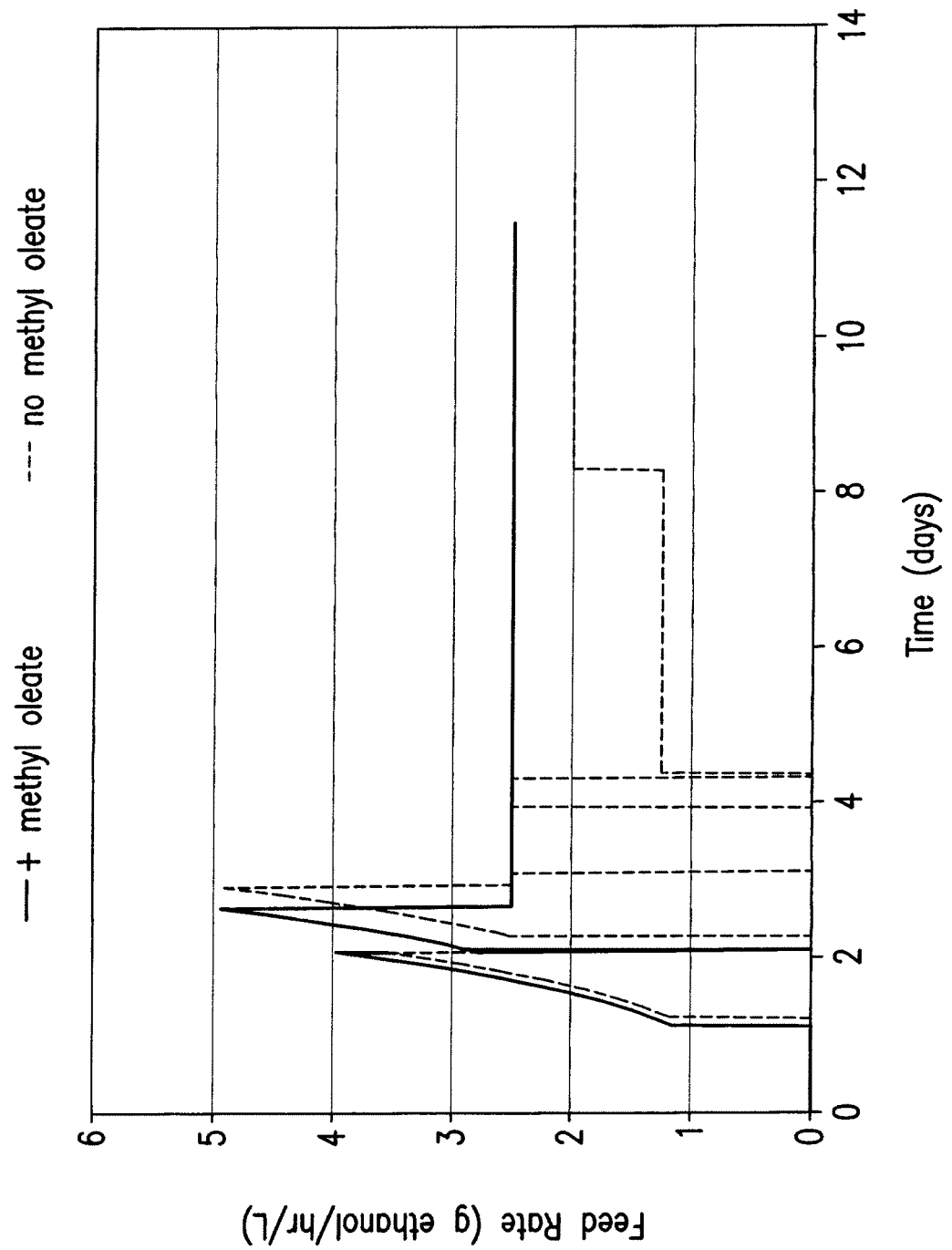
Figure 9C:
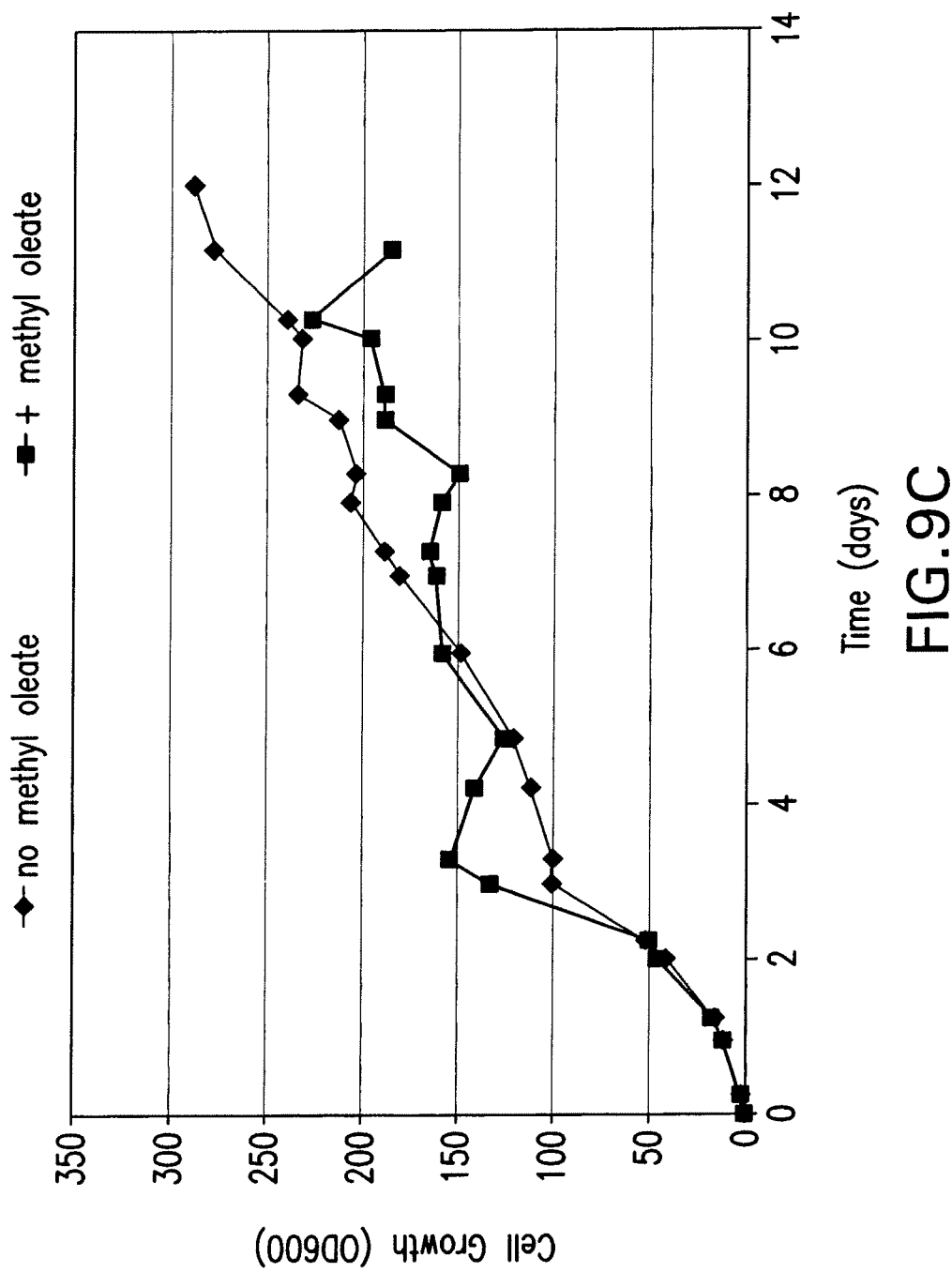

F is the substrate mass flow rate (g/hr), V is the liquid volume in the fermentor at a given time (L), $S_B$ is the concentration of substrate in the batch media (39.03 g/L), $\mu_{set}$ is the specific feed rate (0.058 hr$^{-1}$), t is the batch age (hr), $t_0$ is the batch age when the feed was initiated (hr), $V_0$ is the initial volume in the fermentor (0.7 L), and $V_{feed}$ is the total volume of feed added to the fermentor at a given time (L). The exponential feed phase continued until the ratio of F/V reached a maximum feed rate of 5 g substrate/hr/L bioreactor volume. After reaching this maximum, the ratio of F/V was maintained constant for the remainder of the process at a stationary feed rate of 2.5 g/hr/L. However, as shown in FIG. 9A, the relatively slow rate of ethanol utilization at the beginning of the exponential feed phase resulted in the accumulation of ethanol. This accumulation necessitated manual adjustment of the preset feed rates (FIG. 9B) and an increase in the feed rate doubling time from 12 to 14 hours to maintain a carbon-limited process. Cells grown in the presence of methyl oleate quickly recovered and resumed growth to the preset maximum and stationary feed rates (FIG. 9C). In contrast, the culture that contained no methyl oleate was slower to consume the accumulated ethanol, and thus required a second suspension of the stationary feed followed by a reduction of the stationary feed rate from 2.5 g/hr/L to 1.25 g/hr/L. Overall, strain Y677 had an ethanol consumption rate of 0 to 2.1 g ethanol/g DCW/day in the absence of methyl oleate, and of 0.27-2.9 g ethanol/g DCW/day in the presence of methyl oleate.

Figure 9D:
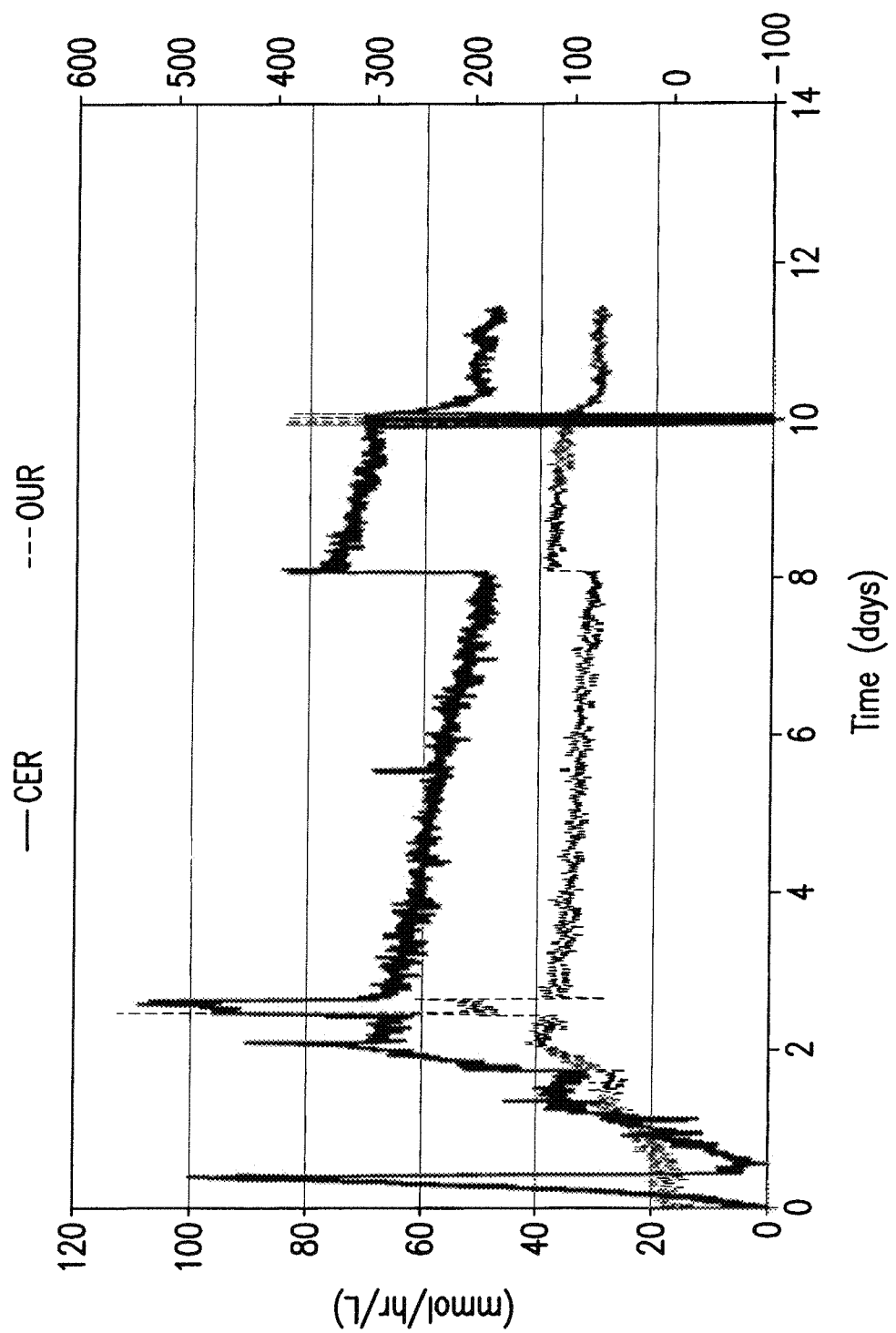

The off gas of the bioreactor was led through a condenser to measure oxygen uptake rate (OUR) and CO$_2$ generation (CER) using an off-gas mass spectrometer. FIG. 9D shows the CER and OUR of strain Y677 in the presence of methyl oleate.

Cell densities and ethanol consumption were monitored by sampling twice a day. At each time point, 1 mL broth samples were taken and diluted 1:1000 in water, and cell density was measured using a spectrophotometer set at 600 nm wavelength.

Levels of ethanol were quantified by HPLC. At each time point, a 1 mL broth sample was taken and diluted 2× in 30 mM sulfuric acid solution (400 uL 30 mM sulfuric acid to 400 uL supernatant for a final concentration of 15 mM sulfuric acid, which matched the concentration of the mobile phase solution). Cells were removed by centrifugation and filtration prior to loading.

Levels of farnesene produced were quantified by GC-FID. At each time point, 100 uL of methyl oleate overlay was taken and diluted 1:40 in ethyl acetate containing 0.001% trans-beta caryophyllene. The mixture was once again diluted 1:100 in ethyl acetate for a final 1:4000 dilution, which fit within the calibration curve for the method. When no methyl oleate was used for product capture, 25 uL culture broth was combined with 975 uL methanol, the mixture was vortexed for five minutes and centrifuged, and finally diluted 1:100 in ethyl acetate containing 0.001% trans-beta caryophyllene before analysis.

Figure 9E:
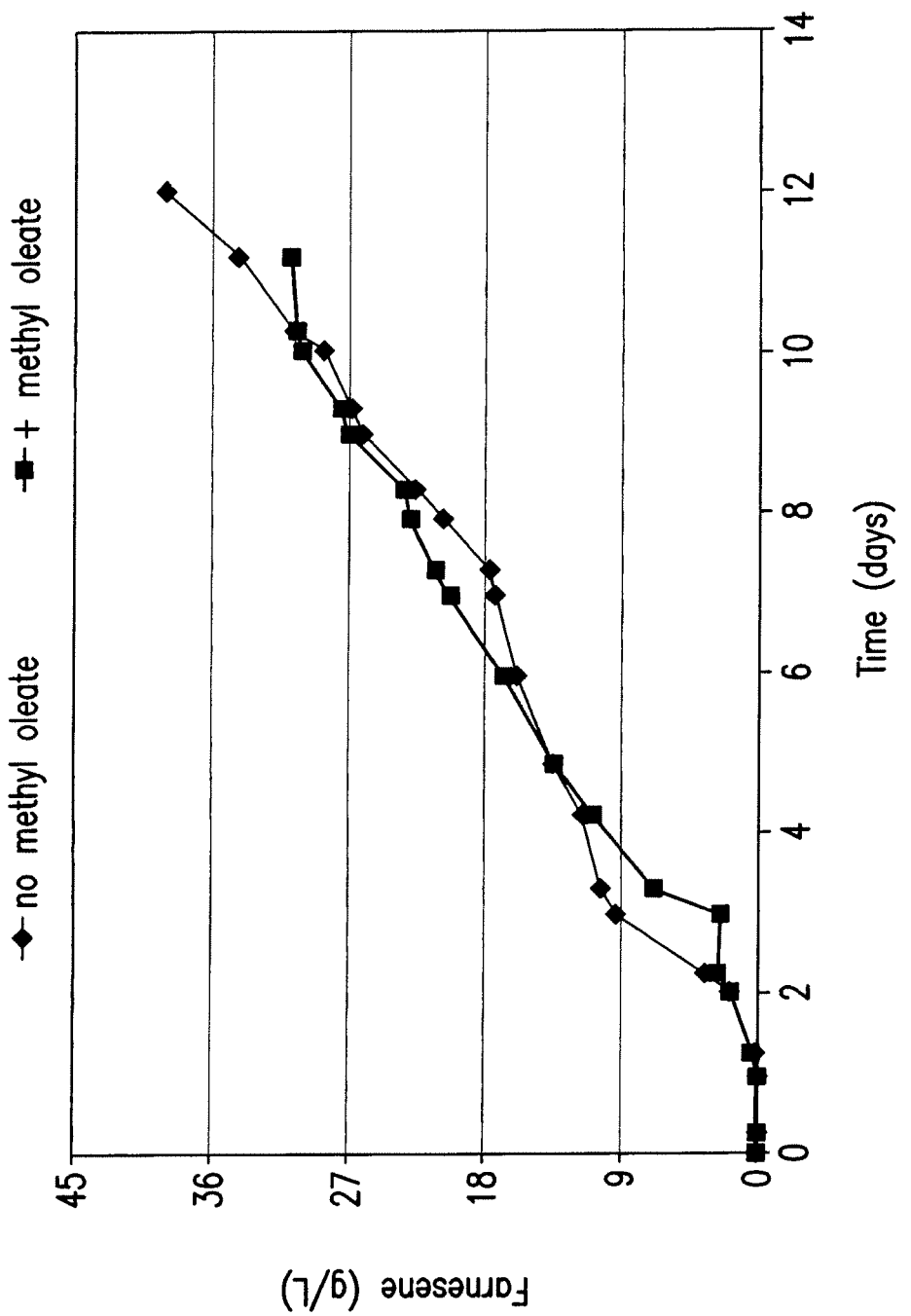

As shown in FIG. 9E, in the presence of methyl oleate strain Y677 reached a peak farnesene titer of 30 g/L, and in the absence of methyl oleate it reached a peak farnesene titer of 40 g/L.

Example 9

This example describes the production of amorpha-4,11-diene and farnesene by host cells in oxygen-restricted fermentation.

Y283 and Y352 seed cultures were prepared and used to inoculate bioreactors containing 800 mL batch medium (Table 15) and 100 mL methyl oleate as described in Example 3.

TABLE 15

Bioreactor media

| Component | Seed Medium | Batch Medium |
|---|---|---|
| glucose (g/L) | 20 | 30 |
| galactose (g/L) | 0 | 5 |
| methionine (g/L) | 0 | 0.25 |
| (NH$_4$)$_2$SO$_4$ (g/L) | 15 | 15 |
| KH$_2$PO$_4$ (g/L) | 8 | 8 |
| MgSO$_4$*7H2O (g/L) | 6.15 | 6.15 |
| Yeast vitamin solution (mL/L) (Table 9) | 12 | 12 |
| Yeast trace metals solution (mL/L) (Table 9) | 10 | 10 |
| succinate (0.5 M, pH 5.0) (mL/L) (Table 7) | 100 | 0 |

Fermentations were carried out in 2L Sartorius Biostat B plus twins with gas-flow ration controllers. The pH was controlled automatically at pH 5.0 with the addition of 15N NH$_4$OH and 5N H$_2$SO$_4$. Temperature was maintained at 30° C. and Biospumex 200 K brand antifoam was used to control foam. Bioreactors were inoculated between OD500 of 0.6-1 and allowed to grow on 30 g/L glucose.

The off gas of the bioreactor was led through a condenser to measure oxygen uptake rate (OUR) and CO$_2$ generation (CER) using an off-gas mass spectrometer. The dissolved oxygen (DO) concentration was measured using an O$_2$ sensor probe (Hamilton, OXYFERM FDA 225, Hamilton Company, Reno, Nev.) with sensitivity between 10 ppb to saturation.

During the initial phase of the fermentation, the bioreactor culture converted the glucose in the batch medium to biomass and ethanol. When the glucose was consumed (8-14 hours after the start of fermentation depending on the availability of oxygen in the culture) glucose repression of the galactose transport and transcription machinery was alleviated, and gene expression off GAL promoters was induced by the galactose in the batch medium. The batch culture continued growth until ethanol produced in the fermentative stage was depleted, at which point a DO spike marked the end of the cultivation period.

For the aerobic process, clean dry air was sparged into the medium at a rate of 1 LPM. The stir rate was initially set to 400 rpm, and a DO feedback control loop and stir cascade program were used to maintain the DO concentration at 40% (Table 16).

For the micro-aerobic processes, gas flow was reduced to 0.25 LPM to minimize the dilution of gases that reach the off gas analyzer and to increase the sensitivity of the mass spectrometer. The rate of oxygen delivery was varied by using different gas-flow ratios of air to nitrogen (Table 16).

For the strict anaerobic process, 100% nitrogen gas was sparged into the aqueous medium at 0.25 LPM prior to inoculation, and a constant stir rate of 400 rpm was maintained throughout the cultivation (Table 16).

TABLE 16

Process parameters for fermentations of strain Y283

| Process | Conditions | Controlled Parameters | Gas Flow Composition |
|---|---|---|---|
| Aerobic | 40% DO | starting 400 rpm DO feedback control with cascading stir rate | 100% air (21% O$_2$) |
| Microaerobic | 0% DO | no DO feedback control fixed stir rate at 400 rpm | 100% air, 0% N2<br>90% air, 10% N2<br>80% air, 20% N2<br>65% air, 35% N2<br>50% air, 50% N2<br>50% air, 50% N2<br>35% air, 65% N2<br>20% air, 80% N2 |
| Anaerobic | No air supplied | fixed stir rate at 400 rpm | 0% air, 100% N2 |

Cell densities and ethanol consumption were monitored by sampling twice a day. At each time point, 1 mL broth samples were taken and diluted 1:100 in water, and cell density was measured using a spectrophotometer set at 600 nm wavelength.

Levels of ethanol and farnesene produced were quantified as described in Example 8 except that the methyl oleaste sample was diluted in ethyl acetate to a final 1:400 dilution instead of 1:4000 dilution.

Figure 10A:
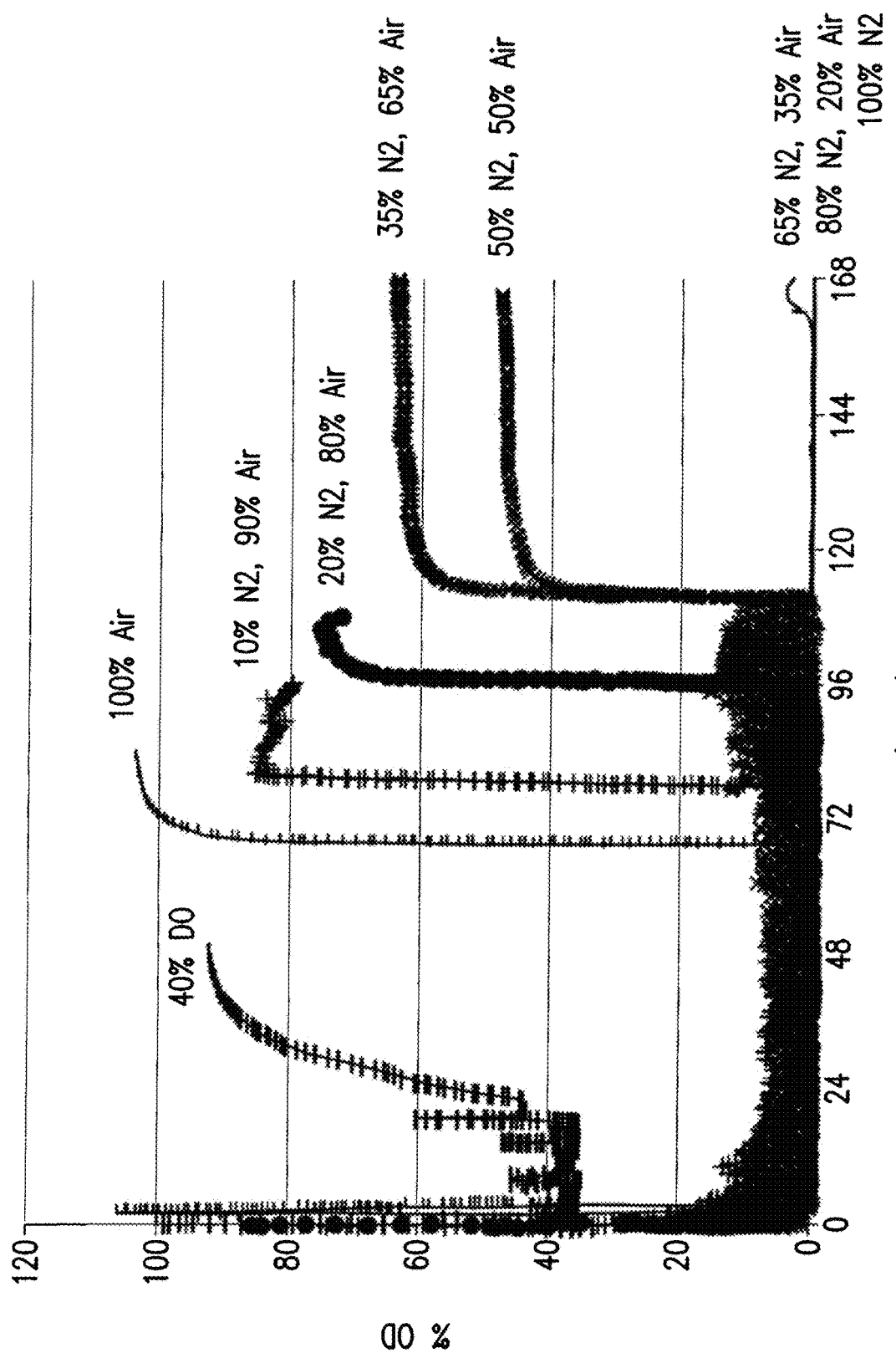
Figure 10B:
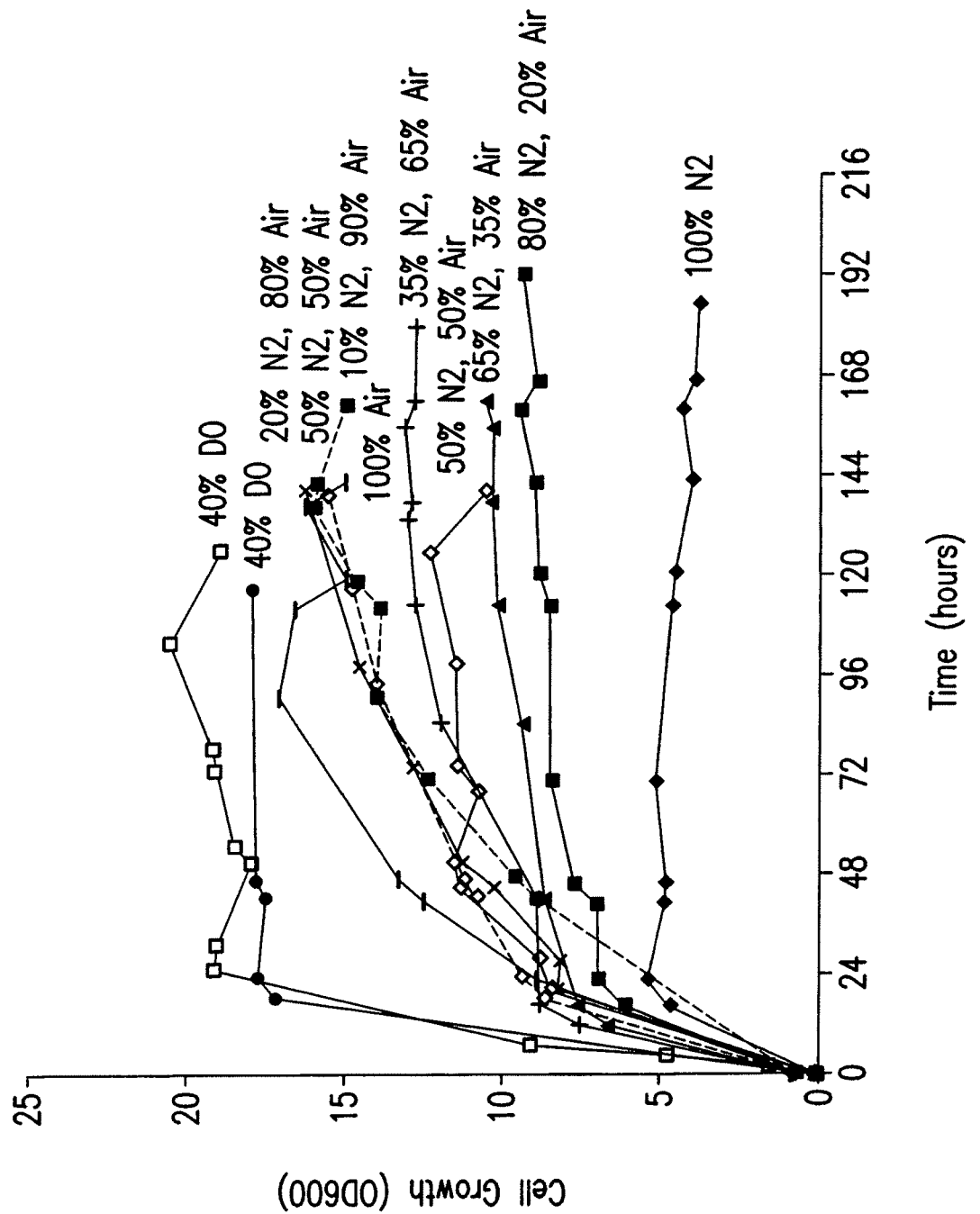
Figure 10D:
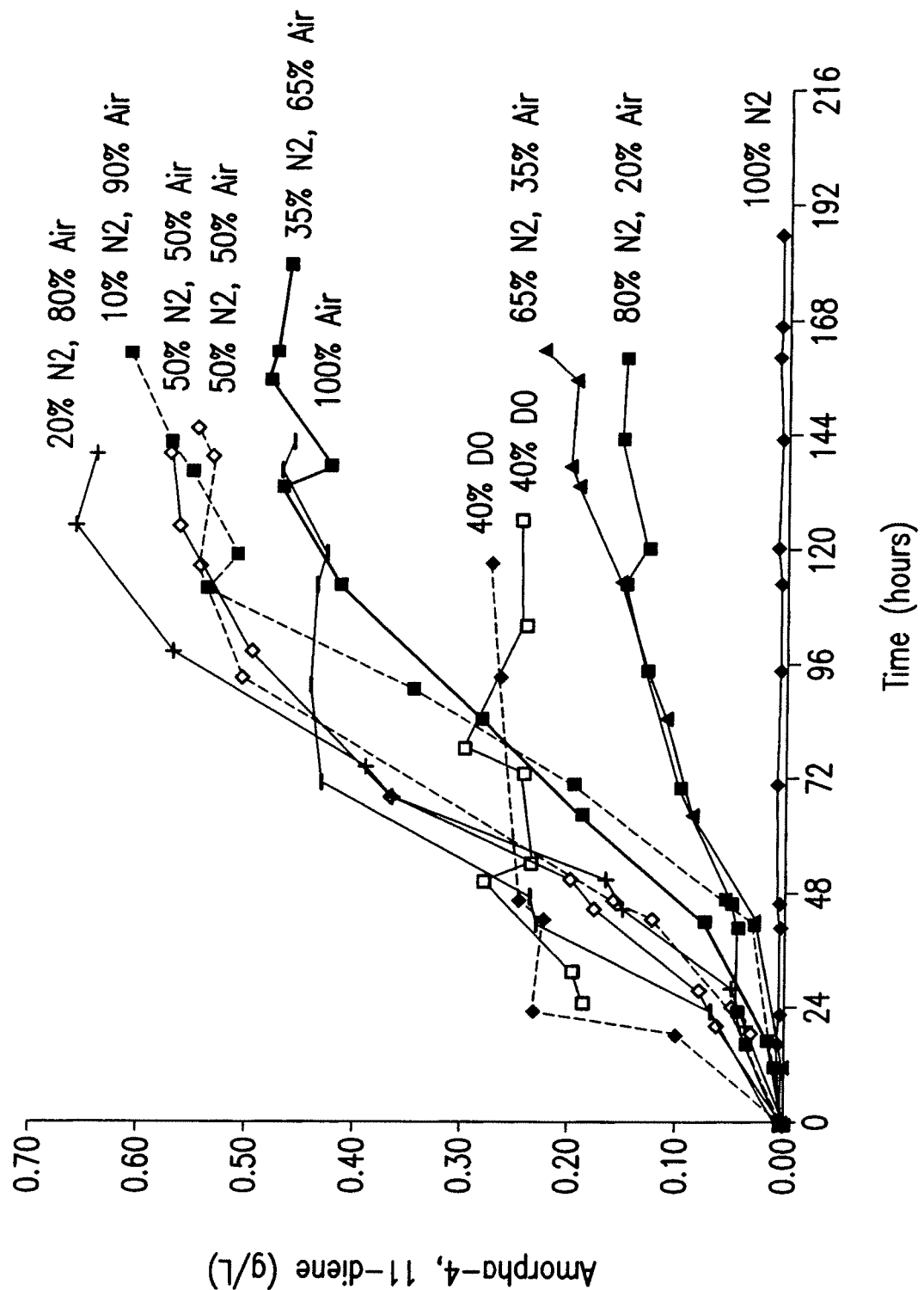

FIG. 10A shows the DO concentrations in the various fermentations of host strain Y283. As shown in FIGS. 10B and 10C, in strain Y283 increased oxygen availability in the culture lead to increased cell growth, increased rate of glucose conversion to ethanol, and increased rate of depletion of ethanol from the medium. Although growth, product formation, and ethanol consumption by strain Y283 were greatest in the fully aerated cultures (DO of 40%), they plateaued after 24 hours. As shown in Table 17, the per cell ethanol consumption rate for all microaerobic processes was between 0.40-0.72 g ethanol/g DCW/day. As shown in FIG. 10D, the best yield of amorpha-4,11-diene relative to carbon input was observed at 80% air and 20% nitrogen.

TABLE 17

Specific ethanol utilization rate (EUR) for microaerobic fermentations

| Gas Ratio | Y283 EUR (g ethanol/g DCW/day) | Y352 EUR (g ethanol/g DCW/day) |
|---|---|---|
| 100% N2 | 0.42 | |
| 80% N2 | 0.40 | |
| 65% N2 | 0.42 | 0.42 |
| 50% N2 | 0.65 | 0.69 |

TABLE 17-continued

Specific ethanol utilization rate (EUR) for microaerobic fermentations

| Gas Ratio | Y283 EUR (g ethanol/g DCW/day) | Y352 EUR (g ethanol/g DCW/day) |
|---|---|---|
| 50% N2 | 0.58 | |
| 35% N2 | 0.54 | |
| 20% N2 | 0.57 | |
| 10% N2 | 0.60 | |
| 0% N2 | 0.72 | 0.88 |

EUR was calculated from peak measured ethanol to lowest measured ethanol for the fermentation.

Figure 10E:
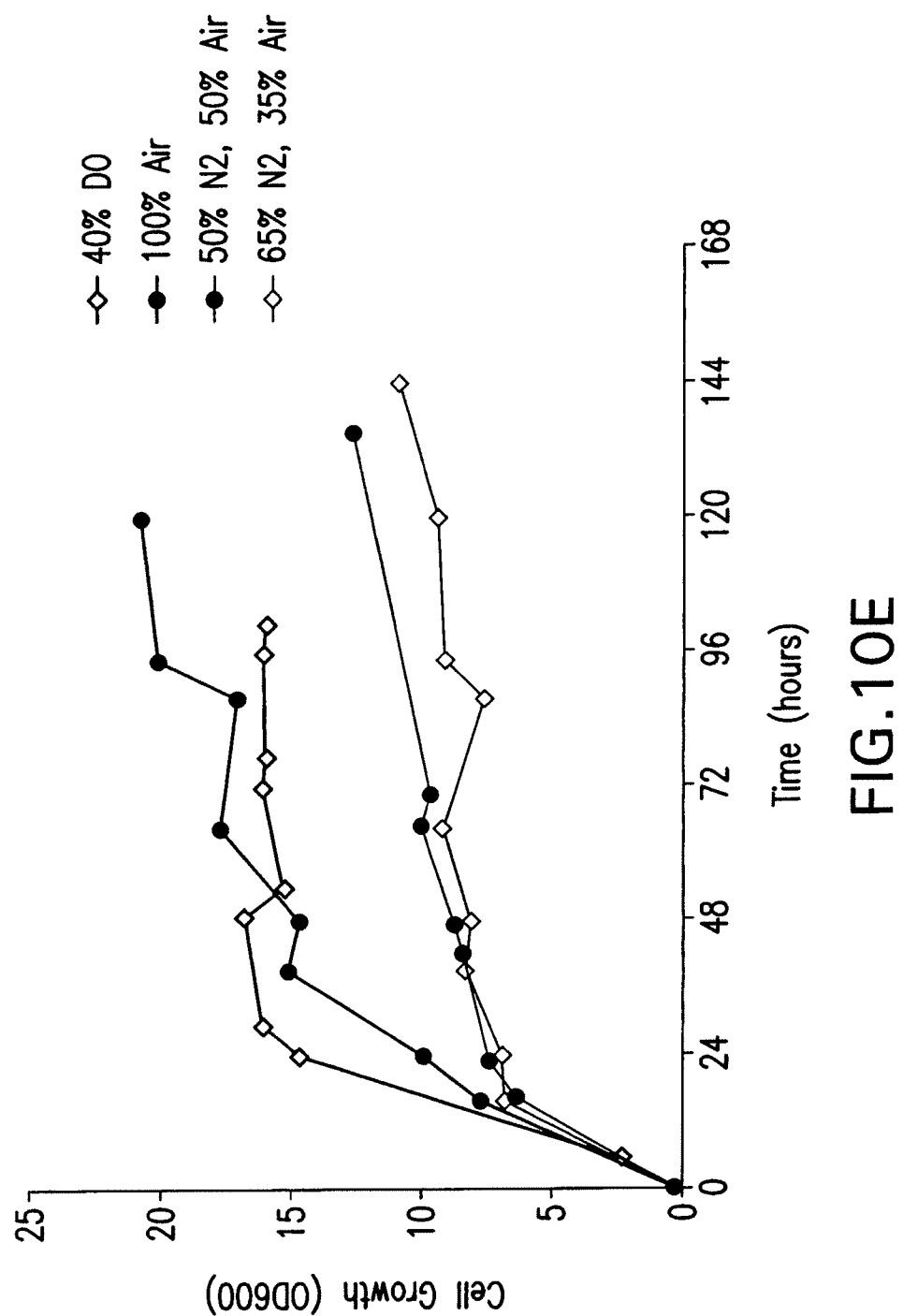
FIGS. 10E through 10G show growth, ethanol production/consumption, and farnesene production by strain Y352 at different degrees of oxygen limitation.
Figure 10F:
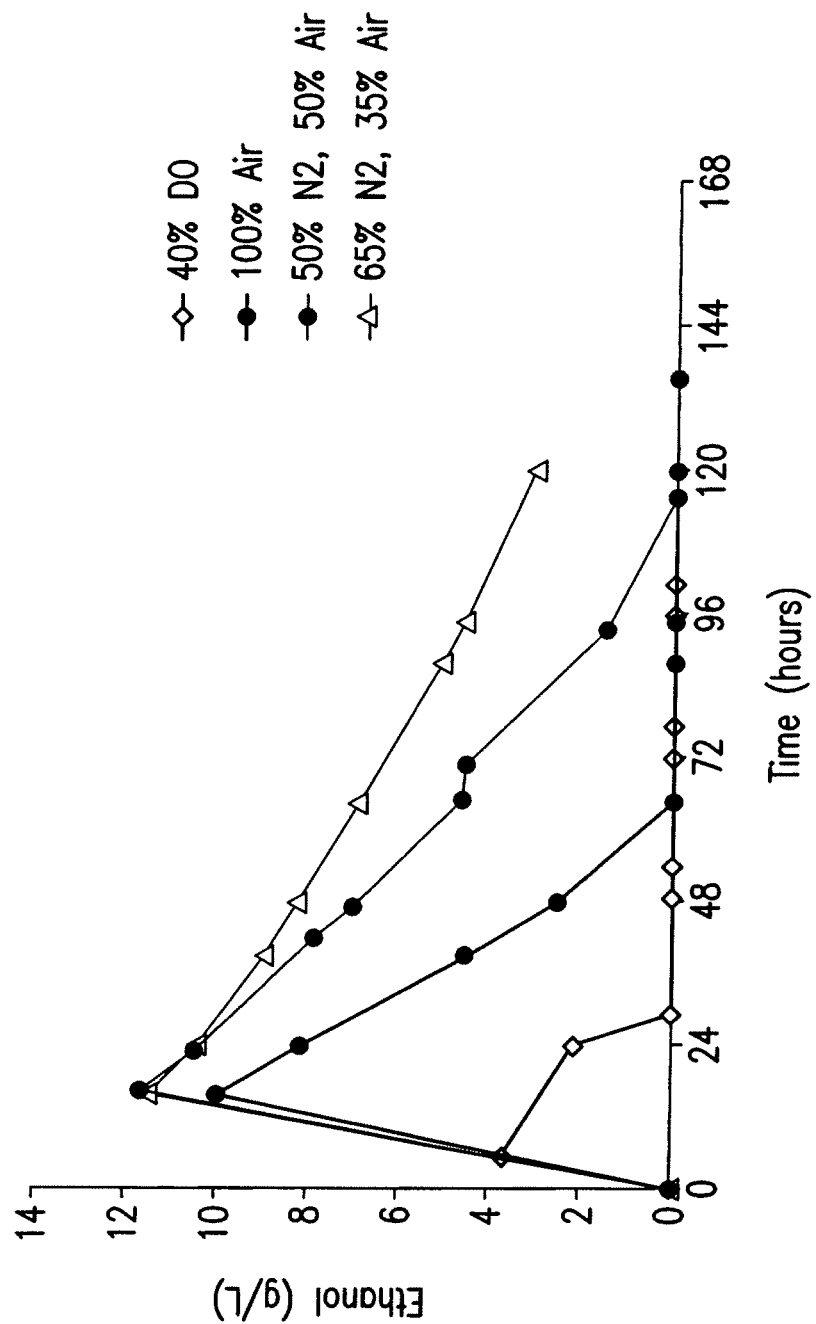
Figure 10G:
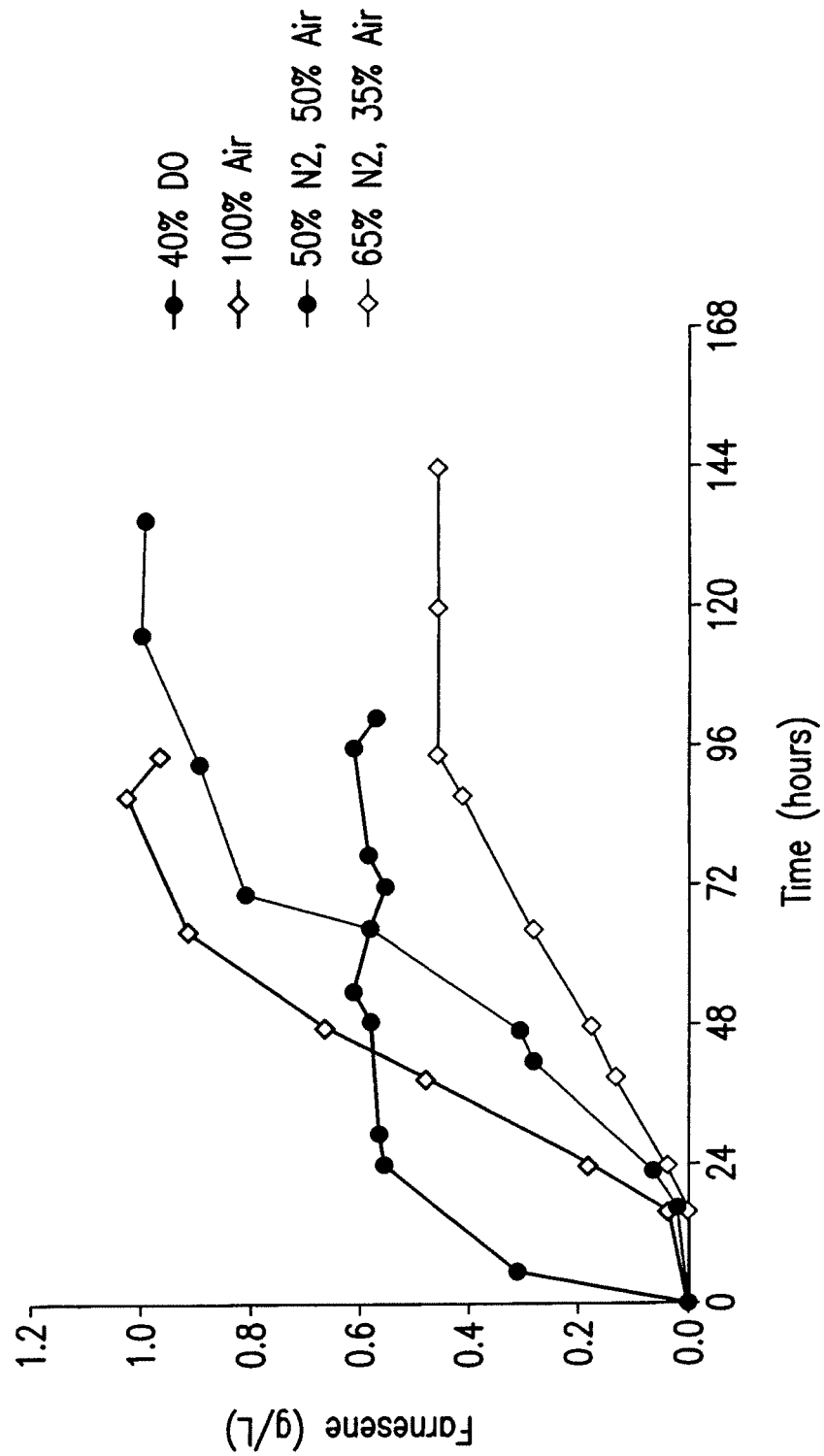

As shown in FIGS. 10E and 10F, in strain Y352 increased oxygen availability in the culture lead to increased cell growth, increased rate of glucose conversion to ethanol, and increased rate of depletion of ethanol from the medium. As shown in Table 17, the per cell ethanol consumption rate for the two microaerobic processes tested was between 0.42-0.88 g ethanol/g DCW/day. As shown in FIG. 10G, although slightly higher yield of farnesene on carbon input was observed at 100% air, production continued over a longer period of time in the microaerobic cultures.

Example 10

This example describes the production of amorpha-4,11-diene by host cells in shake flask cultures with carbon and phosphate restriction.

A stock amyloglucosidase (glucoamylase) enzyme solution was prepared by dissolving solid amyloglucosidase (Sigma A7420-100MG) in 0.5 M succinate buffer (pH 5.0) to a final enzyme concentration of 100 U/mL, and filter sterilizing the solution.

A Y337 seed culture was prepared by inoculating 1 mL frozen Y337 cells into a 250 mL baffled flask containing 50 mL of phosphate-restricted seed medium (Table 18). The seed culture was grown overnight at 30° C. and 200 rpm.

TABLE 18

Phosphate-restricted shake flask culture media

| Component | Seed Medium (mL/L) | Production Medium (mL/L) |
|---|---|---|
| tap water | 350 | 250 |
| 2X batch base[a] | 500 | 500 (no KH$_2$PO$_4$) |
| Yeast vitamin solution (Table 9) | 12 | 12 |
| Yeast trace metals solution (Table 9) | 10 | 10 |
| succinate (0.5 M, pH 5.0) (Table 7) | 100 | 100 |
| glucose-H$_2$O (715 g/L) (Table 7) | 30 | 0 |
| Maltrin M-150 (500 g/L) | 0 | 100 |
| galactose (250 g/L) | 0 | 20 |
| methionine (25 g/L) | 0 | 10 |

[a] 1 g/L KH$_2$PO$_4$, 30 g/L (NH$_4$)$_2$SO$_4$, and 12.3 g/L MgSO$_4$*7H$_2$O (note: no heating while mixing)

The Y337 seed culture was used to inoculate several 250 mL baffled shake flasks to a starting OD$_{600}$ of 0.05. Production flasks contained 40 mL of phosphate-restricted production medium (Table 18). KH$_2$PO$_4$ was added to each flask from a 100 g/L filter-sterilized stock solution to final concentrations of 0.1, 0.25, 0.5, 0.8, 2, and 8 g/L. Prior to inoculation, 80 μL of freshly thawed 100 U/mL amyloglucosidase filter-sterilized stock solution was added to each flask (final concentration of 0.2 U/mL). Production flasks were incubated at 30° C. and 200 rpm for up to 3 days. Over the course of the culture period, glucose was released by glucoamylase at the constant rate of approximately 20 mg/hour.

Amorpha-4,11-diene titers were determined by transferring 2 to 10 μL of the methyl oleate overlay to a clean glass vial containing 500 μL ethyl acetate spiked with beta- or trans-caryophyllene as an internal standard, and analyzing the ethyl acetate samples as described in Example 4.

Figure 11:
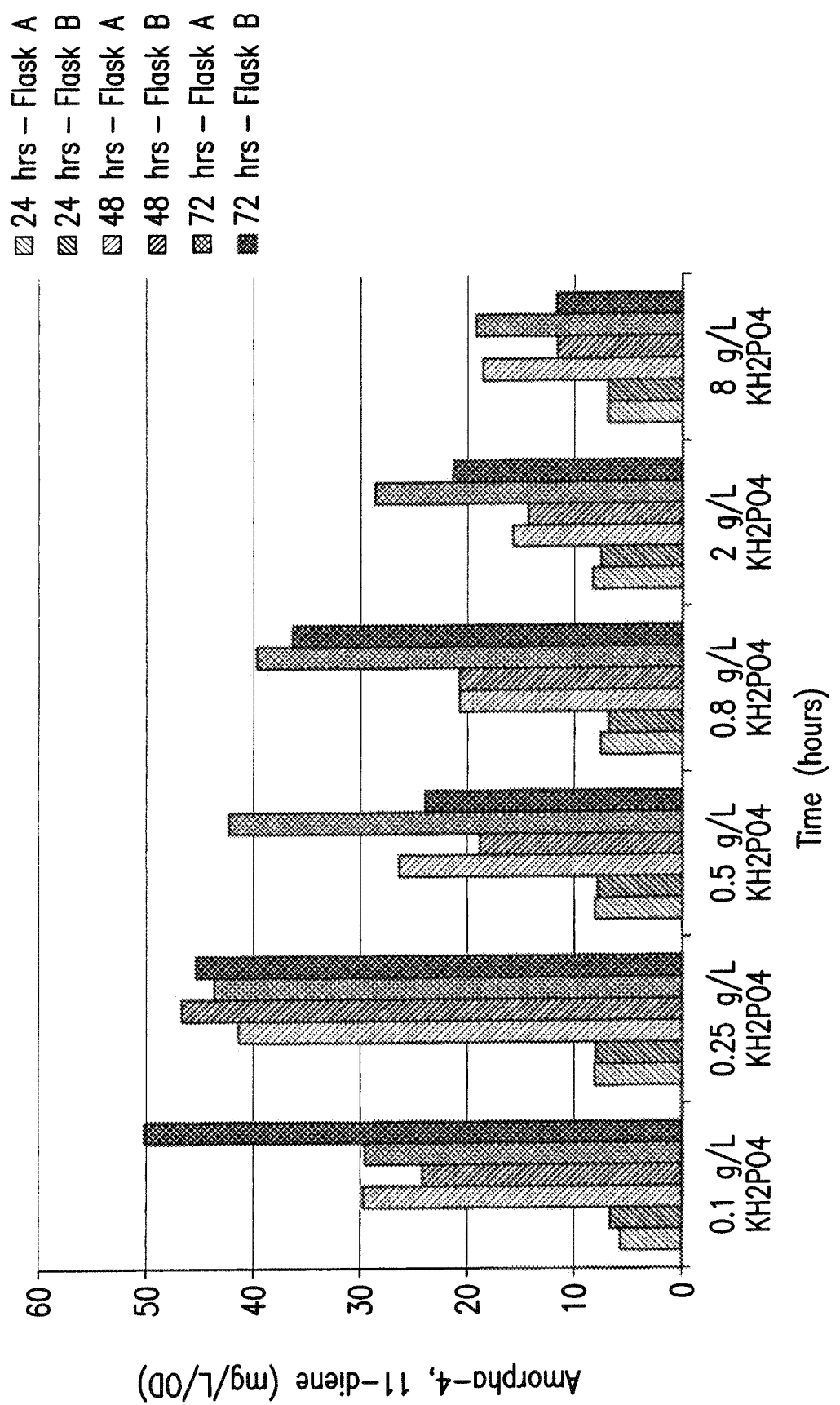
FIG. 11 shows per cell amorpha-4,11-diene productivity by strain Y337 in shake flasks under carbon restriction with varying concentrations of KH2PO4.

As shown in FIG. 11, overall amorpha-4,11-diene titers were comparable at all phosphate concentrations tested except the lowest (0.1 g/L), but cell growth was limited at lower phosphate concentrations, translating into increased per cell production of amorpha-4,11-diene at lower phosphate concentrations.

Example 11

This example describes the production of amorpha-4,11-diene by host cells in fed batch, carbon-restricted fermentation with phosphate restriction and a glucose feed.

Y337 seed cultures were prepared and used to inoculate bioreactors containing phosphate-restricted batch medium (Table 19) as described in Example 3. Fermentations were carried out, and samples were analyzed, essentially as described in Example 4 with the following modifications.

The bioreactor culture was allowed to grow until glucose in the batch medium was depleted, at which point, an exponential feed was initiated for which phosphate-restricted glucose feed medium (Table 19) was pumped into the bioreactors at the rate defined by the following equations:

$$F = V\mu_{set}S_B e^{\mu_{set}(t-t_0)}$$

$$V = V_0 + V_{feed}$$

Figure 12A:
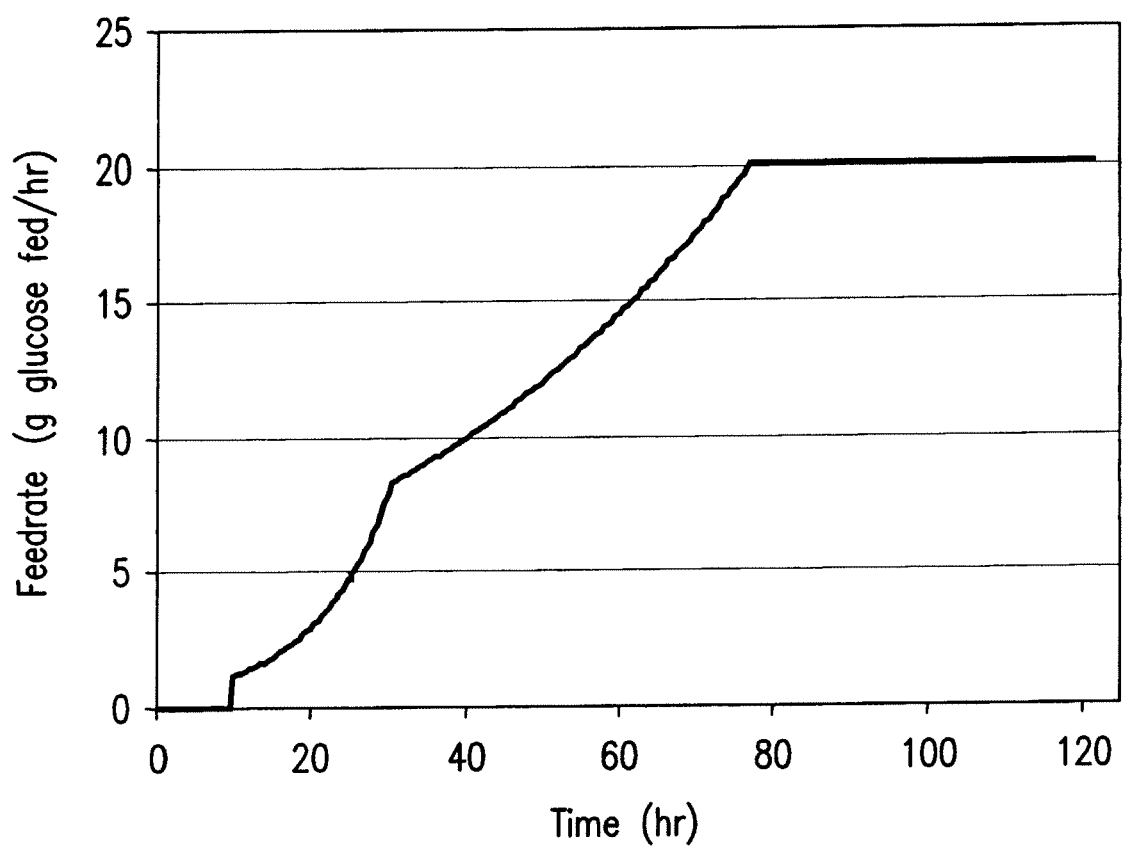
FIG. 12 shows a fed-batch fermentor feed (A), and cell growth (B) and amorpha-4,11-diene production (C) by strain Y337 under carbon- and phosphate-restriction using a glucose feed.

F is the substrate mass flow rate (g/hr), V is the liquid volume in the bioreactor at a given time (L), $S_B$ is the concentration of substrate in the batch medium (19.5 g/L), $\mu_{set}$ is the specific feed rate (0.087 hr$^{-1}$), t is the batch age (hr), $t_0$ is the batch age when the feed was initiated (hr), $V_0$ is the initial volume in the bioreactor, and $V_{feed}$ is the total volume of feed added to the bioreactor at a given time (L). The exponential feed continued until the ratio of F/V reached a preset maximum feed rate (Table 20). After reaching this maximum feed rate, the ratio of F/V was maintained constant for the remainder of the process at a preset stationary feed rate. However, because the volume (V) continued to increase as more feed was added to the bioreactor, the substrate mass flow rate (F) continued to increase until the volume reached the maximum working volume of the bioreactor (approximately 3 times the starting volume). For the rest of the process, the bioreactor volume was held constant by removing cell broth continuously from the reactor, and the substrate mass flow rate (F) was held constant. FIG. 12A shows the glucose feed rate profile of the fermentation.

TABLE 19

Phosphate-restricted bioreactor media

| Component | Seed Medium[a] | Batch Medium[b] | Glucose Feed Medium[c] | Mixed Feed Medium[d] |
|---|---|---|---|---|
| glucose (g/L) | 20 | 19.5 | 578 | 425 |
| (NH$_4$)$_2$SO$_4$ (g/L) | 15 | 15 | 0 | 0 |
| KH$_2$PO$_4$ (g/L) | 1 | See Tables 20 and 21 | See Table 20 | See Table 21 |

TABLE 19-continued

Phosphate-restricted bioreactor media

| Component | Seed Medium[a)] | Batch Medium[b)] | Glucose Feed Medium[c)] | Mixed Feed Medium[d)] |
|---|---|---|---|---|
| MgSO$_4$*7H2O (g/L) | 6.15 | 6.15 | 5.12 | 5.12 |
| K$_2$SO$_4$ (g/L) | 0 | 0 | 3.5 | 3.5 |
| Na$_2$SO$_4$ (g/L) | 0 | 0 | 0.28 | 0.28 |
| Yeast vitamin solution (mL/L) (Table 9) | 12 | 12 | 12 | 12 |
| Yeast trace metals solution (mL/L) (Table 9) | 10 | 10 | 10 | 10 |
| succinate (0.5 M, pH 5.0) (mL/L) (Table 7) | 100 | 0 | 0 | 0 |
| 95% (v/v) ethanol (mL/L) | 0 | 0 | 0 | 237 |

Production of amorpha-4,11-diene was induced at an OD$_{600}$ of approximately 50.

Figure 12B:
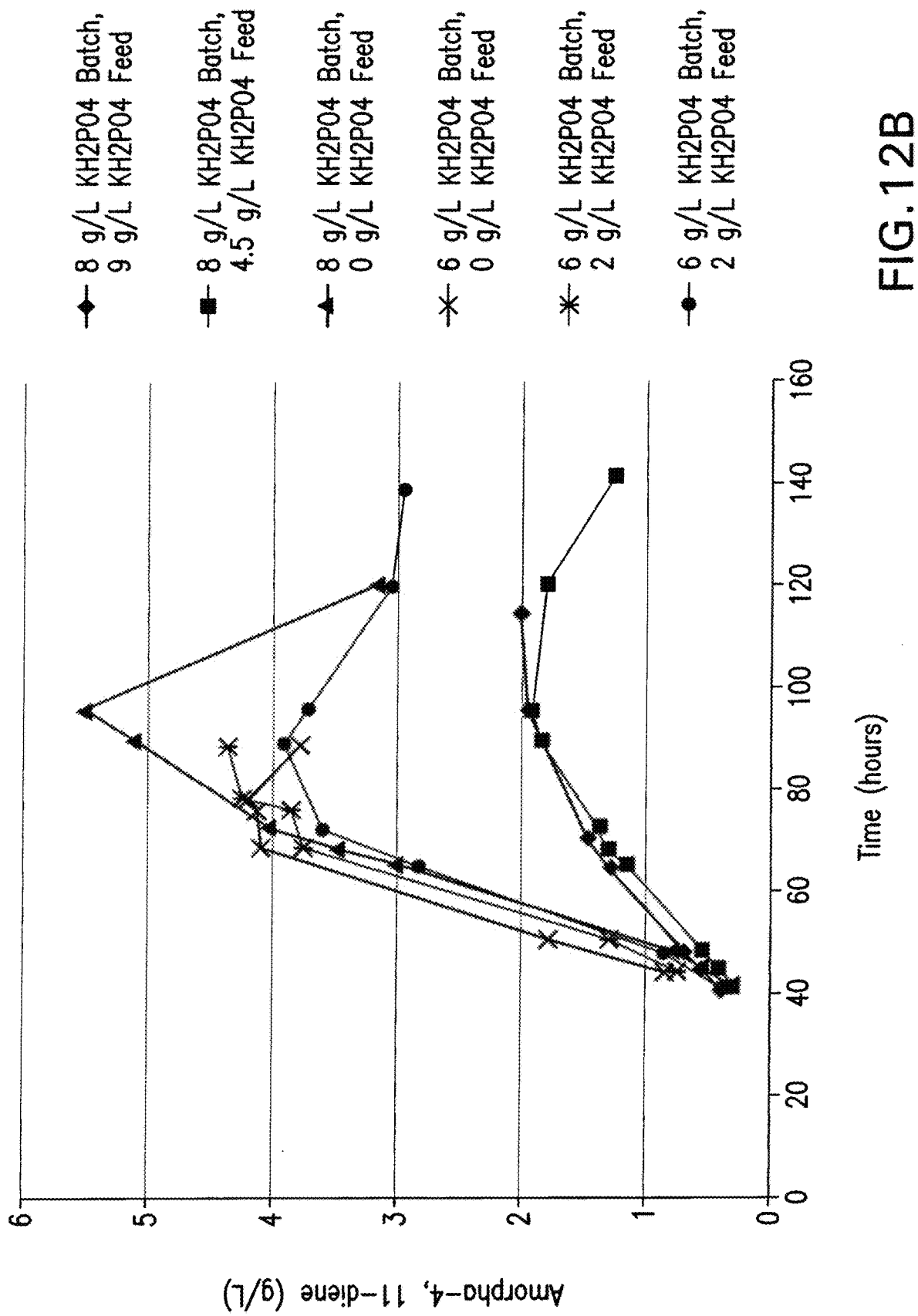
Figure 12C:
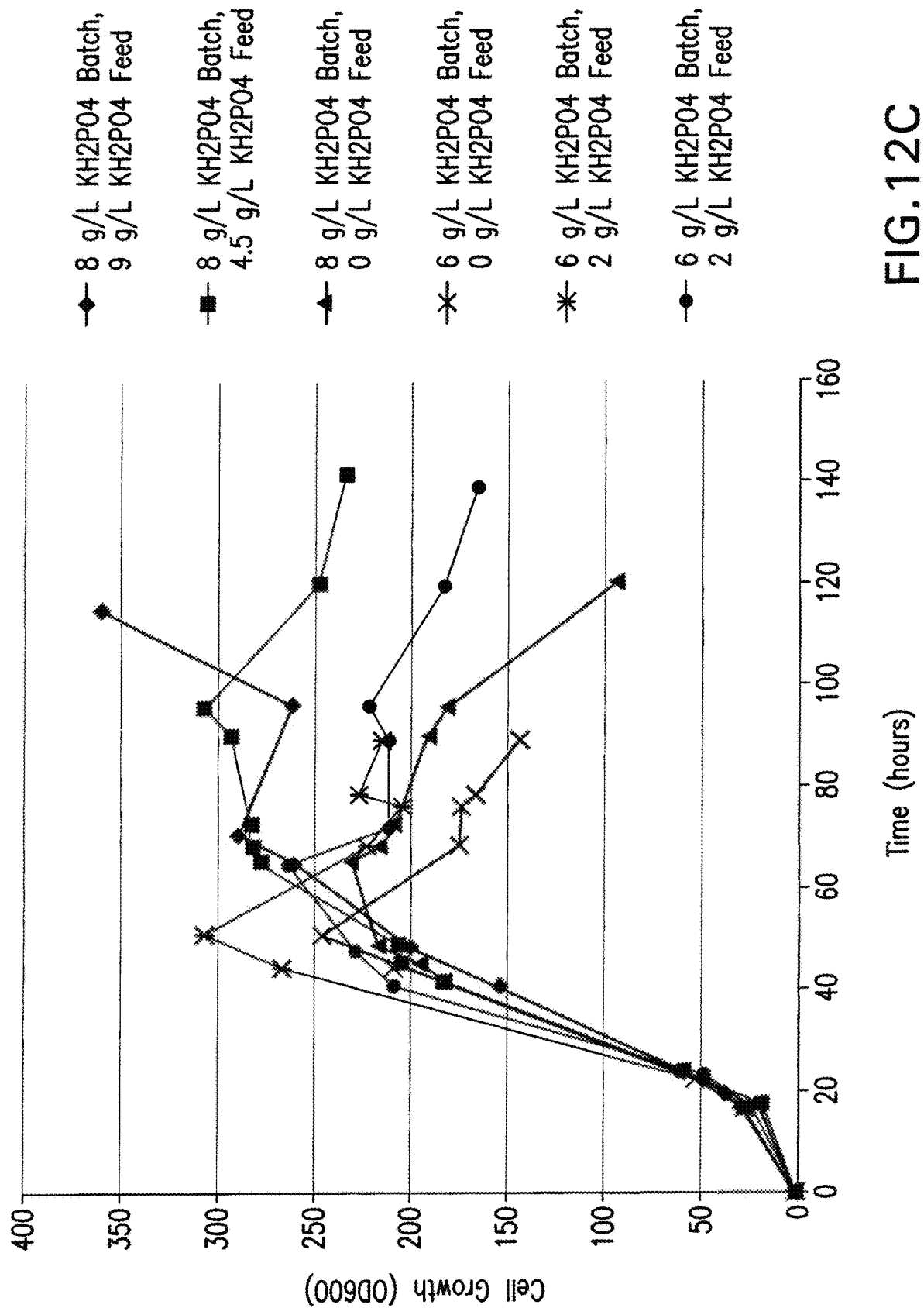

As shown in Table 20 and FIG. 12B, supplying 8 g/L KH$_2$PO$_4$ in the batch medium and no phosphate in the feed medium showed the best amorpha-4,11-diene production at 5.52 g/L. Under these conditions, phosphate in the batch medium was consumed by 40 hours, and cell growth was consequently restricted (i.e., less carbon went to biomass and more carbon went to production of amorpha-4,11-diene) (FIG. 12C).

TABLE 20

Amorpha-4,11-diene production by strain Y337 with glucose feeds and phosphate restriction

| Batch KH$_2$PO$_4$ (g/L) | Feed KH$_2$PO$_4$ (g/L) | Maximum Feed Rate (g/h/L)[a)] | Stationary Feed Rate (g/h/L)[a)] | Time to Max Titer (hr) | Maximum OD | Maximum Titer (g/L) |
|---|---|---|---|---|---|---|
| 8 | 9 | 10 | 10 | 114.86 | 360 | 2 |
| 8 | 4.5 | 10 | 10 | 95.62 | 307 | 1.92 |
| 8 | 0 | 10 | 10 | 95.66 | 231 | 5.52 |
| 6 | 0 | 10 | 10 | 78.30 | 246 | 4.2 |
| 6 | 2 | 10 | 10 | 88.98 | 307 | 4.36 |
| 6 | 2 | 10 | 10 | 89.21 | 263 | 3.91 |
| 6 | 2 | 10 | 5 | 119.73 | 274 | 2.98 |

[a)]g/hr/L is g substrate/hr/L bioreactor volume.

Example 12

This example describes the production of amorpha-4,11-diene by host cells in fed batch, carbon-restricted fermentation with phosphate restriction and a mixed glucose/ethanol feed.

Y337 seed cultures were prepared and used to inoculate bioreactors containing phosphate-restricted batch medium (Table 19) as described in Example 3. Fermentations were carried out, and samples were analyzed, essentially as described in Example 4 with the following modifications.

During the early phase of the fermentation, some of the glucose in the batch medium was converted to ethanol. The bioreactor culture was allowed to grow until the glucose and the ethanol in the batch medium was depleted, at which point, an exponential feed was initiated for which phosphate-restricted mixed feed medium (Table 19) was pumped into the bioreactor at the rate defined by the following equations:

$$F = V \mu_{set} S_B e^{\mu_{set}(t-t_0)}$$

$$V = V_0 + V_{feed}$$

F is the substrate mass flow rate (g/hr), V is the liquid volume in the bioreactor at a given time (L), $S_B$ is the concentration of substrate in the batch media (20 g/L), $\mu_{set}$ is the specific feed rate (0.087 hr$^{-1}$), t is the batch age (hr), $t_0$ is the batch age when the feed was initiated (hr), $V_0$ is the initial volume in the bioreactor, and $V_{feed}$ is the total volume of feed added to the bioreactor at a given time (L). The exponential feed phase continued until the ratio of F/V reached a preset maximum feed rate in units of g substrate/hr/L bioreactor volume (Table 21). After reaching this maximum, the ratio of F/V was maintained constant for the remainder of the process at a preset stationary feed rate (Table 21).

Production of amorpha-4,11-diene was induced at an OD$_{600}$ of approximately 50.

Figure 13A:
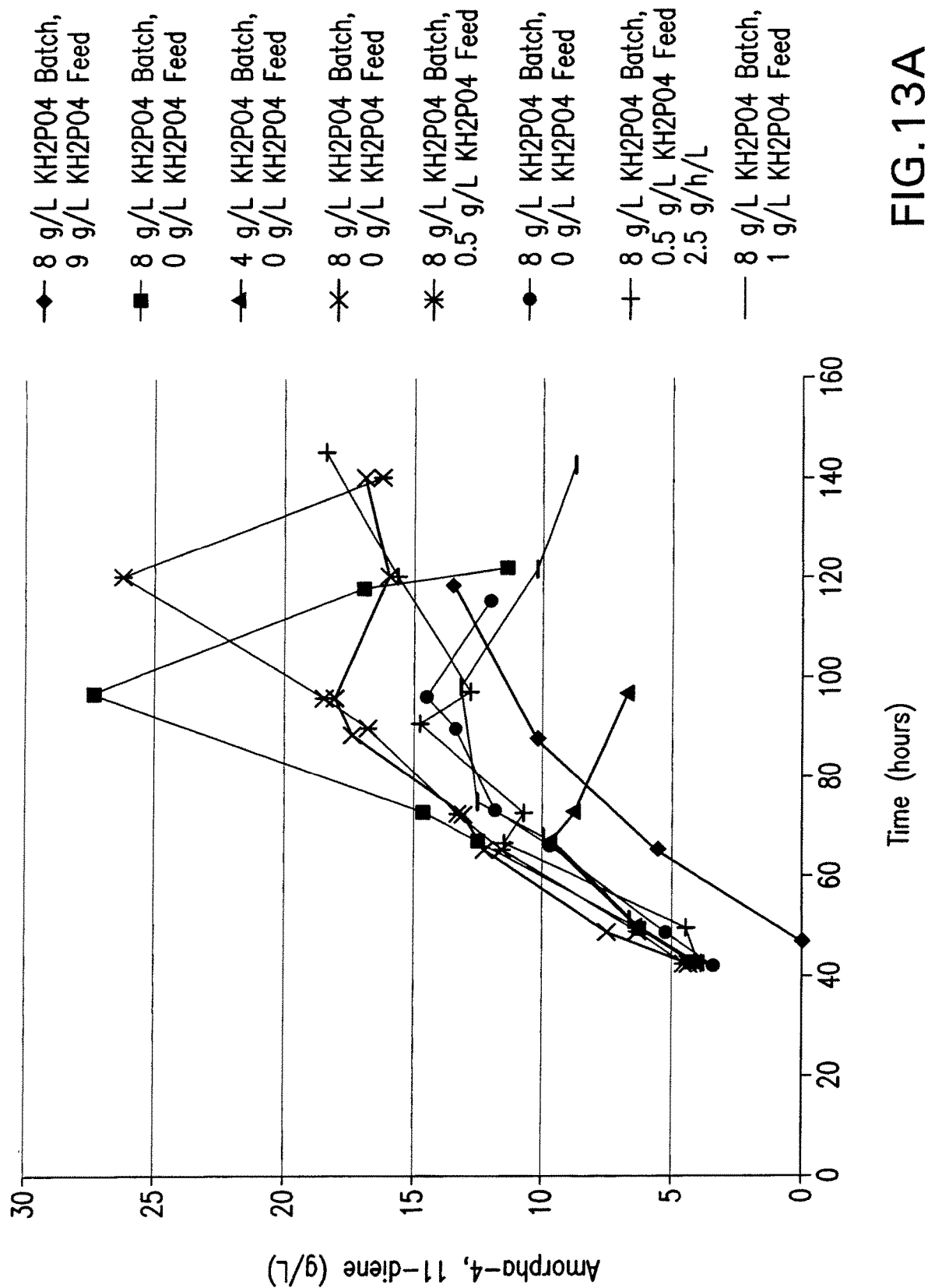
FIG. 13 shows cell growth (A) and amorpha-4,11-diene production (B) by strain Y337 under carbon- and phosphate-restriction using a glucose/ethanol mixed feed.
Figure 13B:
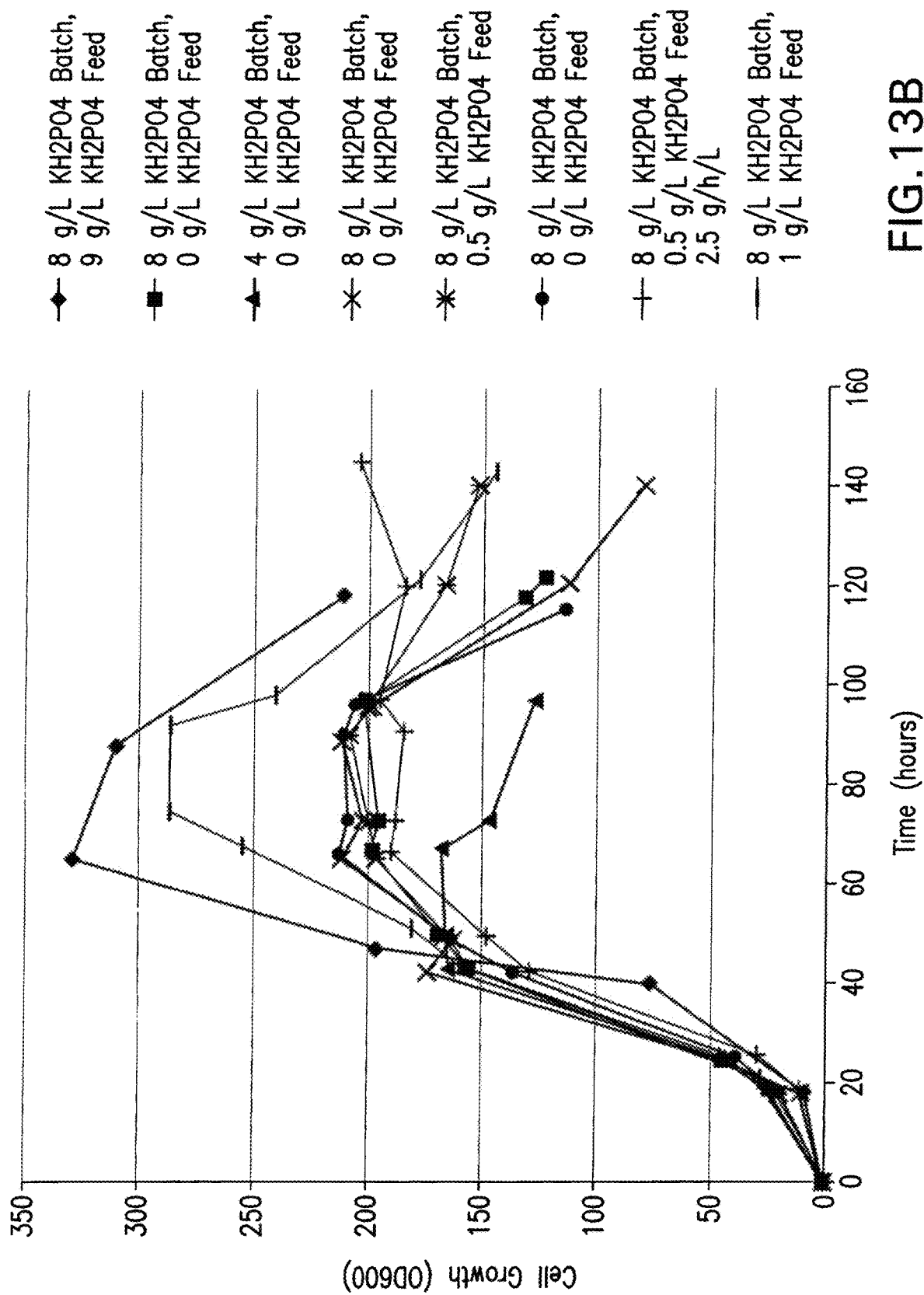

As shown in Table 21 and FIG. 13A, supplying 8 g/L KH$_2$PO$_4$ in the batch medium and 0 to 0.5 g/L KH$_2$PO$_4$ in the feed medium showed the best amorpha-4,11-diene production at over 26 to 27 g/L. Under these conditions, phosphate in the batch medium was consumed by 40 hours, and cell growth was consequently restricted (i.e., less carbon went to biomass and more carbon went to production of amorpha-4,11-diene) (FIG. 13B). Compared to 0 g/L KH$_2$PO$_4$ in the feed medium, 0.5 g/L KH$_2$PO$_4$ in the feed medium allowed cell growth and amorpha-4,11-diene production to continue for an additional 24 hours.

TABLE 21

Amorpha-4,11-diene production by strain Y337 with mixed feeds and phosphate restriction

| Batch KH$_2$PO$_4$ (g/L) | Feed KH$_2$PO$_4$ (g/L) | Maximum Feed Rate (g/h/L)[a)] | Stationary Feed Rate (g/h/L)[a)] | Time to Maximum Titer (hr) | Maximum OD | Maximum Titer (g/L) |
|---|---|---|---|---|---|---|
| 8 | 9 | 8.6 | 8.6 | 118.17 | 329 | 12.69 |
| 8 | 9 | 8.6 | 4.3 | 94.85 | 205 | 10.31 |
| 8 | 0 | 8.6 | 8.6 | 96.83 | 201 | 27.36 |
| 4 | 0 | 8.6 | 8.6 | 67.17 | 168 | 9.68 |

TABLE 21-continued

Amorpha-4,11-diene production by strain Y337 with mixed feeds and phosphate restriction

| Batch KH$_2$PO$_4$ (g/L) | Feed KH$_2$PO$_4$ (g/L) | Maximum Feed Rate (g/h/L)$^{a)}$ | Stationary Feed Rate (g/h/L)$^{a)}$ | Time to Maximum Titer (hr) | Maximum OD | Maximum Titer (g/L) |
|---|---|---|---|---|---|---|
| 8 | 0 | 8.6 | 4.3 | 120.20 | 209 | 16.27 |
| 4 | 0 | 8.6 | 4.3 | 120.20 | 181 | 17.94 |
| 8 | 0 | 8.6 | 8.6 | 95.93 | 212 | 18.07 |
| 8 | 0.5 | 8.6 | 8.6 | 120.33 | 209 | 26.23 |
| 8 | 0 | 10 | 10 | 96.13 | 213 | 14.55 |
| 8 | 0.5 | 10 | 10; dropped to 2.5 at 67 hrs | 145.16 | 204 | 18.38 |
| 8 | 1 | 10 | 10 | 97.69 | 287 | 13.15 |

$^{a)}$g/hr/L is g substrate/hr/L bioreactor volume.

Example 13

This example describes methods for generating *Escherichia coli* host strains that harbor heterologous nucleotide sequences encoding enzymes including enzymes of the MEV pathway and terpene synthases integrated in their genomes.

Figure 14:
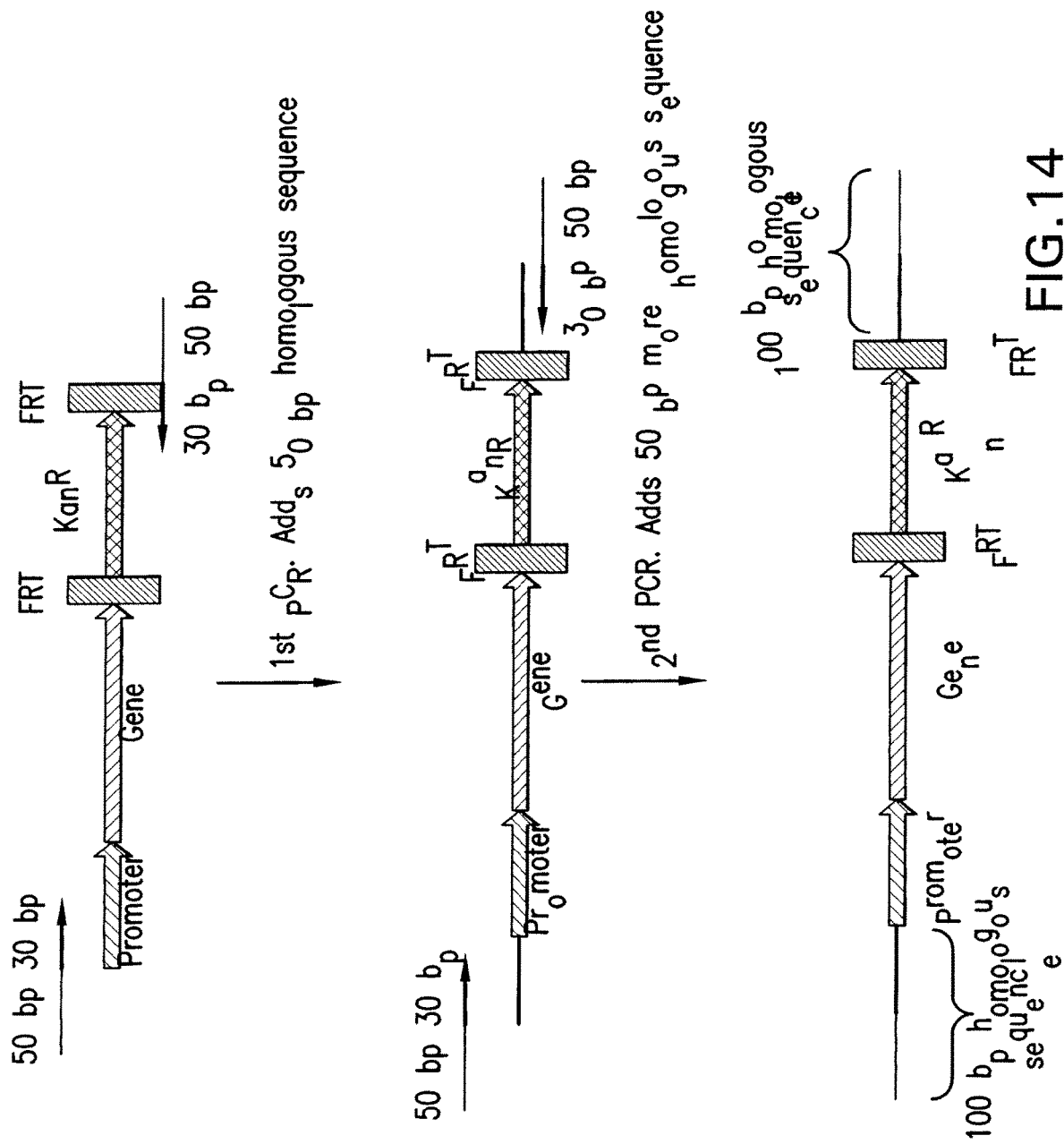
FIG. 14 illustrates the generation of 100 nucleotide long genomic locus-specific sequences flanking promoter-gene-FRT-Kan-FRT cassettes useful in the integration of heterologous nucleotide sequences into the genome of *Escherichia coli*.

Genomic integrations were carried out using a variation of the procedure outlined by Datsenko & Wanner ((2000) *Proc. Natl. Acad. Sci. USA* 97:6640-6645). The method employs plasmids that comprise a T7 promoter-gene of interest-FRT-Kan-FRT cassette. The cassette is flanked on each side by approximately 100 nucleotides that are homologous to the regions flanking the genomic locus targeted for the integration of the cassette. The flanking regions are created by PCR amplifying the cassette using primers that comprise a stretch of approximately 30 nucleotides that is homologous to either the 3' or the 5' end of the cassette, and another stretch of approximately 50 nucleotides that is homologous to the regions flanking the genomic locus (FIG. 14). The resulting PCR product is used as the template in a 2$^{nd}$ PCR reaction that adds another 50 nucleotides of flanking sequence homology on either end of the cassette (FIG. 14). The cassette with its flanking sequences is electroporated into electro-competent *Escherichia coli* cells carrying a plasmid that encodes the Red recombinase protein. Kanamycin ("Kan") resistant colonies are screened by colony PCR. Positive recombinants are treated with P1-phage, and the integration is transferred to a fresh strain via P1-transduction. The resulting strain is transformed with a plasmid that encodes the FLP recombinase, the activity of which causes the Kan gene to be excised from the cassette, leaving behind the T7 promoter-gene of interest at the targeted genomic locus. The final host strain is cured of the FLP recombinase.

Applying the described method, host strain B1060 was generated by integrating a DNA fragment encoding a β-farnesene synthase ("FS") into the Lac operon of *Escherichia coli* strain B1021 (MM294(DE3)(T1R)). To this end, *Escherichia coli* strain MM294 (ATCC33625) was made DE3 using the DE3 lysogenization kit (Novagen, Darmstadt, Germany), and was made resistant to T1 phage by growing the strain in the presence of excess T1 phage, thus yielding strain B1021. A FRT-Kan-FRT cassette was inserted using a modification of the QuikChange methodology (Geiser et al. (2001) *Biotechniques* 31:88-92) into expression plasmid pAM454, which encodes the β-farnesene synthase of *Artemisia annua* (GenBank accession number AY835398), codon-optimized for expression in *Escherichia coli*, under the control of the T7 promoter, thus yielding expression plasmid pAM617. Because the T7-FS-FRT-Kan-FRT cassette in pAM617 is already flanked by sequences from the mhpR and cynX loci (SEQ ID NO: 70), only one round of PCR amplification was necessary to create 100 nucleotide sequences homologous to the mhpR or the cynX sequences that flank the Lac operon. MM294(DE3) host cells harboring expression plasmid pAM88 (encodes the Red recombinase) were grown at 30° C. in LB medium containing 50 ug/mL carbenicillin and 1 mM arabinose to an OD600 of 0.6. The cells were harvested, rendered electro-competent, and transformed with the PCR product. Colonies were obtained after 2 days of growth at 30° C. on LB agar containing 50 ug/mL kanamycin, and the correct integrant was selected by colony PCR. The integration was transferred to a host strain B1021 (MM294(DE3)(T1R)) via P1-transduction, and the resulting strain was made competent and was transformed with expression plasmid pAM89 (encodes the FLP recombinase). Colonies were obtained after 2 days of growth at 30° C. on LB agar containing 50 ug/mL carbenicillin. One colony was isolated and grown at 42° C. in LB media to lose plasmid pAM89, yielding strain B1060 (MM294(DE3)(T1R) lac::T7-FS).

Figure 15:
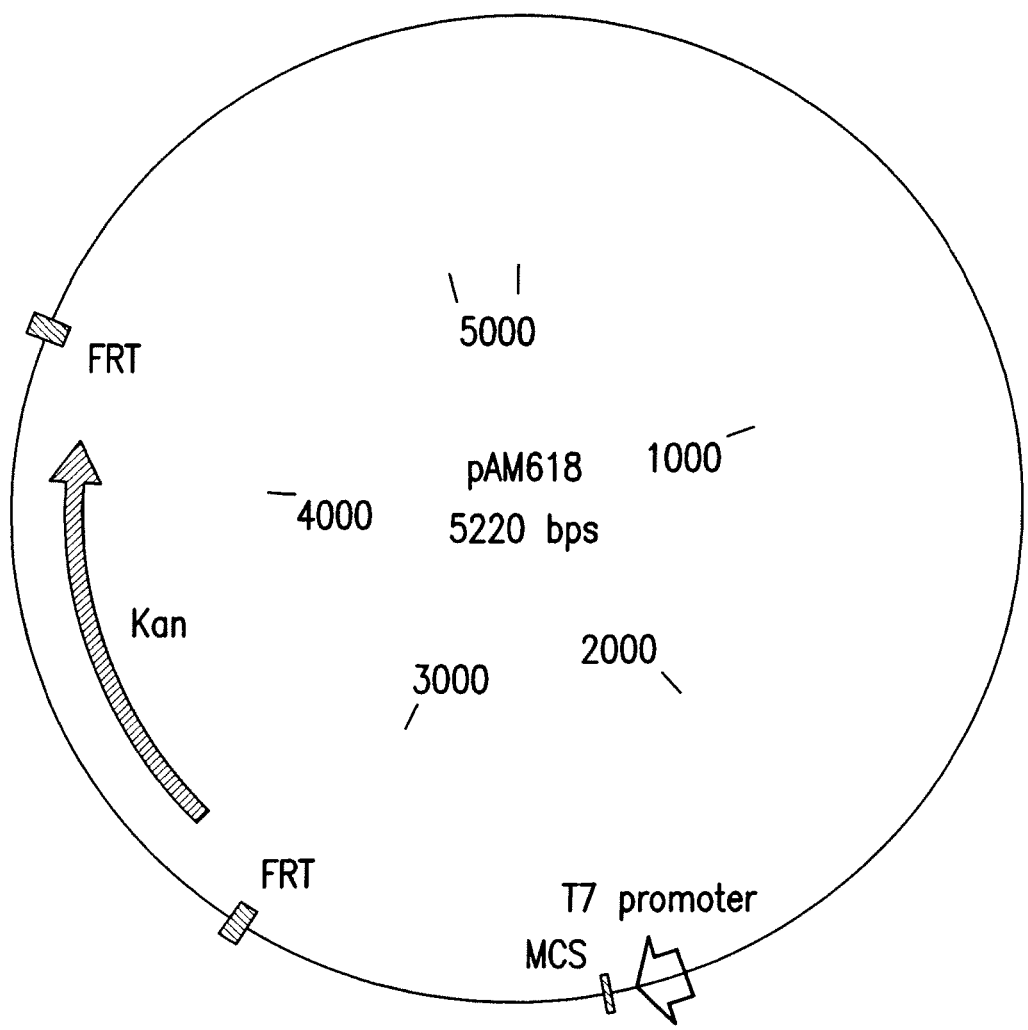
FIG. 15 shows a map of plasmid pAM618.

Host strain B1061 was generated by integrating a DNA fragment encoding a mevalonate kinase ("MK") into the ackpta operon of *Escherichia coli* strain B1021. To this end, a DNA fragment encoding the mevalonate kinase of *Saccharomyces cerevisiae*, codon-optimized for expression in *Escherichia coli* (SEQ ID NO: 71), was inserted into the NdeI BamHI restriction sites of plasmid pAM618. Plasmid pAM618 comprises a T7 promoter followed by a multiple cloning site (MCS) and a FRT-KanR-FRT cassette (SEQ ID NO: 72, FIG. 15). The resulting T7-MK-FRT-Kan-FRT cassette was put through two rounds of PCR amplification as described above to create 100 nucleotide flanking sequences homologous to the ack pta operon. The final PCR product was introduced into *Escherichia coli* strain B1021 as described above, yielding strain B1061 (MM294(DE3) (T1R) ackpta::T7-MK). The integration was also transferred to host strain B1060, yielding strain B1124 (MM294(DE3) (T1R) lac::T7-FS ackpta::T7-MK).

Host strain B1062 was generated by integrating a DNA fragment encoding a phosphomevalonate kinase ("PMK") into the poxB locus of *Escherichia coli* strain B1021. To this end, a DNA fragment encoding the phosphomevalonate kinase of *Saccharomyces cerevisiae*, codon-optimized for expression in *Escherichia coli* (SEQ ID NO: 73), was inserted into the NdeI BamHI restriction sites of plasmid pAM618. The resulting T7-PMK-FRT-Kan-FRT cassette was put through two rounds of PCR amplification as described above to create 100 nucleotide flanking sequences homologous to the poxB locus. The final PCR product was introduced into *Escherichia coli* strain B1021 as described above, yielding strain B1062 (MM294(DE3)(T1R) poxB:: T7-PMK).

Host strain B1273 was generated by integrating a DNA fragment encoding a HMG-CoA reductase ("HMGR") into the ldhA locus of *Escherichia coli* strain B1021. To this end, a DNA fragment encoding the HMGR of *Staphylococcus aureus* (mva; GenBank accession number BA000017, REGION: 2688925 . . . 2687648) was inserted into the EcoRI BamHI restriction sites of plasmid pAM618 after treating the EcoRI restriction site with Klenow fragment. The resulting T7-mvaA-FRT-Kan-FRT cassette was put through two rounds of PCR amplification as described above to create 100 nucleotide flanking sequences homologous to the ldhA locus. The final PCR product was introduced into *Escherichia coli* strain B1021 as described above, yielding strain B1273 (MM294(DE3)(T1R) ldhA::T7-mvaA).

While many specific examples have been provided, the above description is intended to illustrate rather than limit the embodiments provided herein. Many variations of the embodiments will become apparent to those skilled in the art upon review of this specification. The scope of the embodiments should, therefore, be determined not with reference to the above description, but instead should be determined with reference to the appended claims along with their full scope of equivalents.

What is claimed is:

1. A method for producing a heterologous $C_5$-$C_{20}$ isoprenoid compound in a yeast host cell, the method comprising:
   (a) obtaining a plurality of yeast host cells that are capable of making the heterologous $C_5$-$C_{20}$ isoprenoid compound, each said yeast host cell comprising one or more heterologous nucleic acids capable of expressing each enzyme of the MEV pathway or each enzyme of the DX P pathway;
   (b) culturing the yeast host cells in a medium with a glucose feed or a mixed feed comprising glucose and ethanol, wherein the culturing includes a period of time where the host cells are phosphate-limited to yield a fermentation reaction mixture comprising medium, cells, and the heterologous $C_5$-$C_{20}$ isoprenoid compound; and
   (c) recovering the heterologous $C_5$-$C_{20}$ isoprenoid compound from the medium,
   wherein the yeast host cells produce up to 27.36 grams of the heterologous $C_5$-$C_{20}$ isoprenoid compound per liter of fermentation reaction mixture, and
   wherein the heterologous $C_5$-$C_{20}$ isoprenoid compound is amorphadiene.

2. The method of claim 1, wherein the yeast host cells produce between 1.92 and 27.36 grams/liter of amorphadiene.

3. The method of claim 1, wherein the yeast host cells produce between 5.52 and 27.36 grams/liter of amorphadiene.

4. The method of claim 1, wherein the yeast host cells produce between 9.68 and 27.36 grams/liter of amorphadiene.

5. The method of claim 1, wherein the yeast host cells are *S. cerevisiae*.

6. The method of claim 1, wherein each said yeast host cell comprises one or more heterologous nucleic acids capable of expressing an acetyl-CoA acetyltransferase, an HMG-CoA synthase, an HMG-CoA reductase, a mevalonate kinase, a phosphomevalonate kinase and a mevalonate pyrophosphate decarboxylase.

7. The method of claim 1, wherein the medium comprises a batch medium and a feed medium.

8. The method of claim 7, wherein the hatch medium is supplied with 4 to 8 grams/liter phosphate.

9. The method of claim 1, wherein the yeast host cells are maintained under phosphate limited conditions for at least four hours.

10. The method of claim 7, wherein the phosphate in the batch medium is consumed in about 40 hours.

11. The method of claim 7, wherein the feed medium is supplied with no phosphate or 0.5 grams/liter phosphate.

12. The method of claim 7, wherein the feed medium is supplied at a feed rate of 8.6 grams/hour/liter.

13. The method of claim 7, wherein the batch medium comprises glucose at 19.5 grams/liter and the feed medium comprises glucose at 425 gams/liter or 578 grams/liter.

14. The method of claim 13, wherein the feed medium comprises glucose at 425 grams/liter and 237 milliliters/liter 95% ethanol.

15. The method of claim 1, wherein the phosphate is supplied to the medium as potassium dihydrogen phosphate ($KH_2PO_4$).

* * * * *